United States Patent
Bolli et al.

(10) Patent No.: US 12,404,295 B2
(45) Date of Patent: Sep. 2, 2025

(54) (HETERO)ARYL-METHYL-THIO-BETA-D-GALACTOPYRANOSIDE DERIVATIVES

(71) Applicant: Idorsia Pharmaceuticals Ltd, Allschwil (CH)

(72) Inventors: Martin Bolli, Allschwil (CH); Daniel Bur, Therwil (CH); John Gatfield, Allschwil (CH); Corinna Grisostomi, Allschwil (CH); Lubos Remen, Allschwil (CH); Cornelia Zumbrunn, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 831 days.

(21) Appl. No.: 17/633,895

(22) PCT Filed: Aug. 7, 2020

(86) PCT No.: PCT/EP2020/072238
§ 371 (c)(1),
(2) Date: Feb. 8, 2022

(87) PCT Pub. No.: WO2021/028336
PCT Pub. Date: Feb. 18, 2021

(65) Prior Publication Data
US 2022/0315619 A1    Oct. 6, 2022

(30) Foreign Application Priority Data

Aug. 9, 2019    (WO) ................. PCT/EP2019/071416

(51) Int. Cl.
*C07H 19/056*    (2006.01)
(52) U.S. Cl.
CPC ................... *C07H 19/056* (2013.01)
(58) Field of Classification Search
CPC .................................................. C07H 19/056
See application file for complete search history.

(56) References Cited

U.S. PATENT DOCUMENTS

| | | |
|---|---|---|
| 2014/0099319 A1 | 4/2014 | Traber |
| 2023/0295182 A1 | 9/2023 | Bolli et al. |
| 2023/0348442 A1 | 11/2023 | Bolli et al. |
| 2024/0109930 A1 | 4/2024 | Bolli et al. |
| 2024/0124427 A1 | 4/2024 | Bolli et al. |

FOREIGN PATENT DOCUMENTS

| | | |
|---|---|---|
| WO | WO 02/057284 A1 | 7/2002 |
| WO | WO 2005/113568 A1 | 12/2005 |
| WO | WO 2005/113569 A1 | 12/2005 |
| WO | WO 2014/067986 A1 | 5/2014 |
| WO | WO 2014/078655 A1 | 5/2014 |
| WO | WO 2016/120403 A1 | 8/2016 |
| WO | WO 2017/007689 A1 | 1/2017 |
| WO | WO 2018/011094 A1 | 1/2018 |
| WO | WO 2018/209255 A1 | 11/2018 |
| WO | WO 2018/209276 A1 | 11/2018 |
| WO | WO 2019/067702 A1 | 4/2019 |
| WO | WO 2019/067702 A9 | 4/2019 |
| WO | WO 2019/075045 A1 | 4/2019 |
| WO | WO 2019/089080 A1 | 5/2019 |
| WO | WO 2020/078807 A1 | 4/2020 |
| WO | WO 2020/078808 A1 | 4/2020 |
| WO | WO 2020/104335 A1 | 5/2020 |
| WO | WO 2020/210308 A1 | 10/2020 |
| WO | WO 2021/001528 A1 | 1/2021 |
| WO | WO 2021/004940 A1 | 1/2021 |
| WO | WO 2021/028323 A1 | 2/2021 |
| WO | WO 2021/028570 A1 | 2/2021 |

(Continued)

OTHER PUBLICATIONS

Blanchard et al., "Galectin-3 inhibitors: a patent review (2008—present)" Expert Opin Ther Patents vol. 24 No. 10 pp. 1053-1065, DOI:10.1517/13543776.2014.947961 (Year: 2014).*

Rose et al., "Prediction and Prevention of Autoimmune Disease in the 21st Century: A Review and Preview" vol. 183 No. 5 pp. 403-406, DOI: 10.1093/aje/kwv292 (Year: 2016).*

Marcel Verweij, "Preventative Medicine Between Obligation and Aspiration", published by Springer-Science and Business Media, DOI:10.1007/978-94-015-9365-6, pp. 25-48 (Year: 2000).*

Penny et al., "The challenges for cancer chemoprevention" Chem Soc Rev vol. 44, pp. 8836-8847, DOI: 10.1039/c5cs00705d (Year: 2015).*

(Continued)

*Primary Examiner* — Eric Olson
(74) *Attorney, Agent, or Firm* — Hoxie & Associates LLC

(57) ABSTRACT

The present invention relates to compounds of Formula (I)

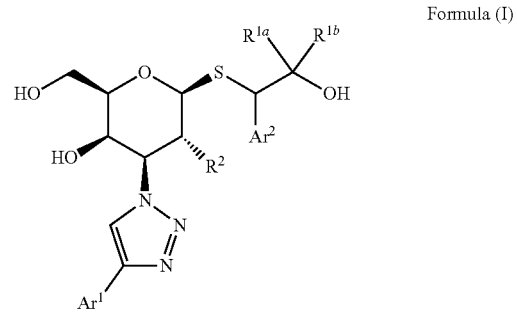

Formula (I)

wherein $Ar^1$, $Ar^2$, $R^{1a}$, $R^{1b}$, and $R^2$ are as described in the description, their preparation, to pharmaceutically acceptable salts thereof, and to their use as pharmaceuticals, to pharmaceutical compositions containing one or more compounds of Formula (I), and especially to their use as Galectin-3 inhibitors.

15 Claims, No Drawings

(56) References Cited

FOREIGN PATENT DOCUMENTS

| WO | WO 2021/038068 A1 | 3/2021 |
|---|---|---|
| WO | WO 2022/073969 A1 | 4/2022 |
| WO | WO 2022/090544 A1 | 5/2022 |
| WO | WO 2022/171594 A1 | 8/2022 |
| WO | WO 2022/184755 A1 | 9/2022 |

OTHER PUBLICATIONS

Li et al., "Functions of Galectin-3 and Its Role in Fibrotic Diseases" The Journal of Pharmacology and Experimental Therapeutics vol. 351, pp. 336-343, DOI:10.1124/jpet.114.218370 (Year: 2014).*

Traber et al., "Therapy of Experimental NASH and Fibrosis with Galectin Inhibitors" PLOS One vol. 8 issue 12 pp. 1-12, DOI:doi:10.1371/journal.pone.0083481 (Year: 2013).*

Ma et al., "Galectin-3 Inhibition Is Associated with Neuropathic Pain Attenuation after Peripheral Nerve Injury" PLOS One vol. 11 No. 2 e0148792, doi:10.1371/journal.pone.0148792 (Year: 2016).*

U.S. Appl. No. 18/248,007, filed Apr. 5, 2023 (371(c) Date), Bolli et al.

U.S. Appl. No. 18/251,273, filed May 1, 2023 (371(c) Date), Bolli et al.

U.S. Appl. No. 18/264,751, filed Aug. 8, 2023 (371(c) Date), Bolli et al.

U.S. Appl. No. 18/548,833, filed Sep. 1, 2023 (371(c) Date), Bolli et al.

U.S. Appl. No. 17/633,941, filed Feb. 8, 2022 (371(c) Date), Bolli et al.

U.S. Appl. No. 17/634,512, filed Feb. 10, 2022 (371(c) Date), Bolli et al.

U.S. Appl. No. 17/638,799, filed Feb. 25, 2022 (371(c) Date), Bolli et al.

Arciniegas, E. et al., "Galectin-1 and Galectin-3 and Their Potential Binding Partners in the Dermal Thickening of Keloid Tissues," The American Journal of Dermatopathology, 2019, 41 (3), 193-204.

Barondes, S. et al., "Galectins: A Family of Animal β-Galactoside-Binding Lectins," Cell, 1994, 76, 597-598.

Burguillos, M. et al., "Macroglia-Secreted Galectin-3 Acts as a Toll-like Receptor 4 Ligand and Contributes to Microglial Activation," Cell Reports, 2015, 10, 1626-1638.

Caldararu, O. et al., "Are crystallographic B-factors suitable for calculating protein conformational entropy?," Physical Chemistry Chemical Physics, 2019, 21, 18149-18160.

Caniglia, J. et al., "A potential role for Galectin-3 inhibitors in the treatment of COVID-19," PeerJ, 2020, 8:e9392, 10 pages, doi:10.7717/peerj.9392.

Chasse, T. et al., "Dendritic encapsulation-roles of cores and branches," Tetrahedron, 2003, 59, 3853-3861.

Chen, W-S. et al., "Galectin-3 Inhibition by a Small-Molecule Inhibitor Reduces Both Pathological Corneal Neovascularization and Fibrosis," Investigative Ophthalmology & Visual Science, 2017, 58 (1), 9-20.

Chen, Y-J. et al., "Galectin-3 Enhances Avian H5N1 Influenza A Virus-Induced Pulmonary Inflammation by Promoting NLRP3 Inflammasome Activation," The American Journal of Pathology, 2018, 188 (4), 1031-1042.

Chiariotti, L. et al., "Galectin genes: Regulation of expression," Glycoconjugate Journal, 2004, 19, 441-449.

Dang, Z. et al., "Tubular Atrophy and Interstitial Fibrosis After Renal Transplantation Is Dependent on Galectin-3," Transplantation, 2012, 93 (5), 477-484.

Deroo, E. et al., "The role of galectin-3 and galectin-3-binding protein in venous thrombosis," Blood, 2015, 125 (11), 1813-1821.

Falcone, C. et al., "Galectin-3 Plasma Levels and Coronary Artery Disease: A New Possible Biomarker of Acute Coronary Syndrome," International Journal of Immunopathology and Pharmacology, 2011, 24 (4), 905-913.

Farhad, M. et al., "The role of Galectin-3 in modulating tumor growth and immunosuppression within the tumor microenvironment," OncoImmunology, 2018, 7(6), e1434467, 8 pages, https://doi.org/10.1080/2162402X.2018.1434467.

Galectin Therapeutics, "Combination Immunotherapy with Galectin-3 Inhibitor GR-MD-02 Enhances Effects in Pre-clinical Models and Early Results of Phase 1 Clinical Trials," Press Release, dated 2017, 3 pages.

Galectin Therapeutics, "Galectin Therapeutics Announces Results from Phase 2b NASH-CX Trial," Bloomberg, Press Release, dated 2017, 5 pages.

Galecto Biotech, "Galecto Biotech's Lead Molecule TD139 is Safe, Well Tolerated, with Direct Target Engagement and Biomarker Effects in a Clinical Phase Ib/IIa trial in IPF Patients," Press Release, dated 2017, 4 pages.

Gallo, R. et al., "Silica-supported $HClO_4$ promotes catalytic solvent- and metal-free O—H insertion reactions with diazo compounds," Green Chemistry, 2018, 20, 4547-4556.

Gao, P. et al., "Galectin-3: its role in asthma and potential as an anti-inflammatory target," Respiratory Research, 2013, 14:136, 9 pages, doi:10.1186/1465-9921-14-136.

Gehlken, C. et al., "Galectin-3 in Heart Failure: An Update of the Last 3 Years," Heart Failure Clinics, 2018, 14, 75-92.

Giguère, D. et al., "Carbohydrate triazoles and isoxazoles as inhibitors of galectins-1 and -3," Chemical Communications, 2006, 2379-2381.

Greene, T. et al., Eds., Protective Groups in Organic Synthesis, Wiley-Interscience, 1999.

Guha, P. et al., "Cod glycopeptide with picomolar affinity to galectin-3 suppresses T-cell apoptosis and prostate cancer metastasis," Proceedings of the National Academy of Sciences, 2013, 110 (13), 5052-5057.

Henderson, N. et al., "Galectin-3 regulates myofibroblast activation and hepatic fibrosis," Proceedings of the National Academy of Sciences, 2006, 103 (13), 5060-5065.

Henderson, N. et al., "Galectin-3 Expression and Secretion Links Macrophages to the Promotion of Renal Fibrosis," The American Journal of Pathology, 2008, 172 (2), 288-298.

Henderson, N. et al., "The regulation of inflammation by galectin-3," Immunological Reviews, 2009, 230, 160-171.

Hsu, D. et al., "Galectin-3 Expression is Induced in Cirrhotic Liver and Hepatocellular Carcinoma," International Journal of Cancer, 1999, 81, 519-526.

Jin, Q-h. et al., "Serum galectin-3: a risk factor for vascular complications in type 2 diabetes mellitus," Chinese Medical Journal, 2013, 126 (11), 2109-2115.

Johannes, L. et al., "Galectins at a glance," Journal of Cell Science, 2018, 131, jcs208884, 9 pages, doi:10.1242/jcs.208884.

Keipour, H. et al., "Copper-Catalyzed Carbenoid Insertion Reactions of α-Diazoesters and α-Diazoketones into Si—H and S—H Bonds," Journal of Organic Chemistry, 2017, 82, 3000-3010.

Kikuchi, Y. et al., "Galectin-3-positive call infiltration in human diabetic nephropathy," Nephrology Dialysis Transplantation, 2004, 19 (3), 602-607.

Kwak, Y. et al., "Effect of Initiator and Ligand Structures on ATRP of Styrene and Methyl Methacrylate Initiated by Alkyl Dithiocarbamate," Macromolecules, 2008, 41, 6627-6635.

Lacina, L. et al., "Glycophenotype of Psoriatic Skin," Folia Biologica (Praha), 2006, 52, 10-15.

Ladouceur, S et al., "One-Pot Click Synthesis of IN-Alkyl-4-aryl-1,2,3-triazoles from Protected Arylalkynes and Alkyl Bromides," Synthesis, 2011, 22, 3604-3611.

Leffler, H. et al., "Introduction to galectins," Glycoconjugate Journal, 2004, 19, 433-440.

Li, P. et al., "Hematopoietic-derived Galectin-3 Causes Cellular and Systemic Insulin Resistance," HHS Public Access, Author manuscript, available in PMC 2017, 22 pages, face of article states: Published in final edited form as: Cell, 2016, 167(4), 973-984, doi: 10.1016/j.cell.2016.10.025.

Liu, F-T. et al., "Galectins in acute and chronic inflammation," Annals of the New York Academy of Sciences, 2012, 1253, 80-91.

Lowary, T. et al., "Recognition of synthetic O-methyl, epimeric, and amino analogues of the acceptor α-L-Fuc p-(1 → 2)-β-D-Gal p-OR by the blood-group A and B gene-specified glycosyltransferases," Carbohydrate Research, 1994, 251, 33-67.

(56) References Cited

OTHER PUBLICATIONS

MacKinnon, A. et al., "Regulation of Transforming Growth Factor-β1-driven Lung Fibrosis by Galectin-3," American Journal of Respiratory and Critical Care Medicine, 2012, 185 (5), 537-546.

Nachtigal, M. et al., "Galectin-3 Expression in Human Atherosclerotic Lesions," American Journal of Pathology, 1998, 152 (5), 1199-1208.

Nakamura, S. et al., "Highly Enantioselective Reaction of α-Lithio 2-Quinolyl Sulfide Using Chiral Bis(oxazoline)s: A New Synthesis of Enantioenriched Thiols," European Journal of Organic Chemistry, 2002, 1690-1695.

Nishi, Y. et al., "Role of Galectin-3 in Human Pulmonary Fibrosis," Allergology International, 2007, 56 (1), 57-65.

Noël, J-C. et al., "Galectin-3 is Overexpressed in Various Forms of Endometriosis," Appllied Immunohistochemistry & Molecular Morphology, 2011, 19 (3), 253-257.

Rao, S. et al., "Regulation of Eosinophil Recruitment and Activation by Galectins in Allergic Asthma," Frontiers in Medicine, 2017, 4:68, 12 pages, doi:10.3389/fmed.2017.00068.

Rebholz, C. et al., "Plasma galectin-3 levels are associated with the risk of incident chronic kidney disease," Kidney International, 2018, 93, 252-259.

Remington, The Science and Practice of Pharmacy, 21st Edition, 2005, Part 5, "Pharmaceutical Manufacturing," published by Lippincott Williams & Wilkins.

Ruvolo, P., "Galectin 3 as a guardian of the tumor microenvironment," Biochimica et Biophysica Acta, 2016, 1863, 427-437.

Saegusa J. et al., "Galectin-3 Is Critical for the Development of the Allergic Inflammatory Response in a Mouse Model of Atopic Dermatitis," The American Journal of Pathology, 2009, 174 (3), 922-931.

Sano, H. et al, "Human Galectin-3 Is a Novel Chemoattractant for Monocytes and Macrophages," The Journal of Immunology, 2000, 165 (4), 2156-2164.

Sciacchitano, S. et al., "Galectin-3: One Molecule for an Alphabet of Diseases, from A to Z," International Journal of Molecular Sciences, 2018, 19, 379, 59 pages, doi:10.3390/ijms9020379.

Sharma, U. et al., "Novel anti-inflammatory mechanisms of N-Acetyl-Ser-Asp-Lys-Pro in hypertension-induced target organ damage," HHS Public Access, Author manuscript, available in PMC 2019, 17 pages, face of article states: Published in final edited form as: *Am J Physiol Heart Circ Physiol.*, 2008, 294(3): H1226-H1232, doi:10.1152/ajpheart.00305.2007.

Stahl, P. et al., Eds., Handbook of Pharmaceutical Salts, Properties, Selection, and Use, Wiley-VCH, 2008.

Sundblad, V. et al., "Regulated expression of galectin-3, a multifunctional glycan-binding protein, in haematopoietic and non-haematopoietic tissues," Histology and Histopathology, 2011, 26, 247-265.

Taniguchi, T. et al., "Serum Levels of Galectin-3: Possible Association with Fibrosis, Aberrant Angiogenesis, and Immune Activation in Patients with Systemic Sclerosis," Journal of Rheumatology, 2012, 39 (3), 539-544.

Thandavarayan, R. et al., "14-3-3 protein regulates Ask1 signaling and protects against diabetic cardiomyopathy," Biochemical Pharmacology, 2008, 75, 1797-1806.

Verteramo, M. et al., "Interplay between Conformational Entropy and Solvation Entropy in Protein-Ligand Binding," Journal of the American Chemical Society, 2019, 141, 2012-2026.

Vuong, L. et al., "An Orally Active Galectin-3 Antagonist Inhibits Lung Adenocarcinoma Growth and Augments Response to PD-L1 Blockade," Cancer Research, 2019, 79 (7), 1480-1492.

Watanabe, H. et al., "Bulky Thiols and Their Coordination Compounds. An Improvement of the Removal Method of Tetrahydropyranyl Group from Thiols and Its Application for Ligand Syntheses," Chemistry Letters, 1996, 999-1000.

Witczak, Z. et al., Eds., Click Chemistry in Glycoscience: New Developments and Strategies, 2013, John Wiley & Sons, Inc., Hoboken, New Jersey.

Wouters, J. et al., Eds., Pharmaceutical Salts and Co-crystals, RSC Publishing, 2012.

Zhang, J. et al., "A Novel Thiol Protecting Group: A 2-Thioquinoline Sulfide as a Masked Sulfhydryl Moiety," Tetrahedron Letters, 1999, 40, 1467-1470.

Zhong, X. et al., "The role of galectin-3 in heart failure and cardiovascular disease," Clinical and Experimental Pharmacology and Physiology, 2019, 46, 197-203.

De Oliveira, F. et al., "Galectin-3 in autoimmunity and autoimmune diseases," Experimental Biology and Medicine, 2015, 240, 1019-1028.

Ho, J. et al., "Galectin-3 Is Associated with Restrictive Lung Disease and Interstitial Lung Abnormalities," American Journal of Respiratory and Critical Care Medicine, 2016, 194 (1), 77-83.

Park, A-M. et al., "Galectin-3 Plays an Important Role in Innate Immunity to Gastric Infection by *Helicobacter pylori*," Infection and Immunity, 2016, 84 (4), 1184-1193.

Suárez-Fuentetaja, N. et al., "Circulating Galectin-3 Following Heart Transplant: Long-term Dynamics and Prognostic Value," Revista Española de Cardiología, 2019, 72 (11), 899-906.

Tao, C-C. et al., "Galectin-3 promotes Aβ oligomerization and Aβ toxicity in a mouse model of Alzheimer's disease," Cell Death & Differentiation, 2020, 27, 192-209.

\* cited by examiner

(HETERO)ARYL-METHYL-THIO-BETA-D-GALACTOPYRANOSIDE DERIVATIVES

CROSS REFERENCE TO RELATED APPLICATIONS

This application is the National Stage Entry under 35 U.S.C. § 371 of International Application No. PCT/EP2020/072238 filed Aug. 7, 2020, which claims priority to International Application No. PCT/EP2019/071416 filed Aug. 9, 2019, the contents of each of which are hereby incorporated by reference in their entireties.

The present invention relates to compounds of formula (I) which are galectin-3 inhibitors and their use in the prevention/prophylaxis or treatment of diseases and disorders that are related to galectin-3 binding to natural ligands. The invention also concerns related aspects including processes for the preparation of the compounds, pharmaceutical compositions containing one or more compounds of formula (I), and their medical use as Galectin-3 inhibitors. The compounds of formula (I)) may especially be used as single agents or in combination with one or more therapeutic agents.

Galectins are defined as a protein family based on conserved β-galactoside-binding sites found within their characteristic ~130 amino acid (aa) carbohydrate recognition domains (CRDs) (Barondes S H et al., Cell 1994; 76, 597-598). Human, mouse and rat genome sequences reveal the existence of at least 16 conserved galectins and galectin-like proteins in one mammalian genome (Leffler H. et al., Glycoconj. J. 2002, 19, 433-440). So far, three galectin subclasses were identified, the prototypical galectins containing one carbohydrate-recognition domain (CRD); the chimaera galectin consisting of unusual tandem repeats of proline- and glycine-rich short stretches fused onto the CRD; and the tandem-repeat-type galectins, containing two distinct CRDs in tandem connected by a linker (Zhong X., Clin Exp Pharmacol Physiol. 2019; 46:197-203). As galectins can bind either bivalently or multivalently, they can e.g. cross-link cell surface glycoconjugates to trigger cellular signaling events. Through this mechanism, galectins modulate a wide variety of biological processes (Sundblad V. et al., Histol Histopathol 2011; 26: 247-265).

Galectin-3 (Gal-3), the only chimaera type in the galectin family, has a molecular weight of 32-35 kDa and consists of 250 amino acid residues in humans, a highly conserved CRD and an atypical N-terminal domain (ND). Galectin-3 is monomeric up to high concentrations (100 μM), but can aggregate with ligands at much lower concentrations, which is promoted by its N-terminal non-CRD region via an oligomerisation mechanism that is not yet completely understood (Johannes, L. et al., Journal of Cell Science 2018; 131, jcs208884).

Gal-3 is widely distributed in the body, but the expression level varies among different organs. Depending on its extracellular or intracellular localization, it can display a broad diversity of biological functions, including immunomodulation, host-pathogen interactions, angiogenesis, cell migration, wound healing and apoptosis (Sundblad V. et al., Histol Histopathol 2011; 26: 247-265). Gal-3 is highly expressed in many human tumours and cell types, such as myeloid cells, inflammatory cells (macrophages, mast cells, neutrophils, T cells, eosinophils, etc.), fibroblasts and cardiomyocytes (Zhong X. et al., Clin Exp Pharmacol Physiol. 2019; 46:197-203), indicating that Gal-3 is involved in the regulation of inflammatory and fibrotic processes (Henderson N C. Et al., Immunological Reviews 2009; 230: 160-171; Sano H. et al., J Immunol. 2000; 165(4):2156-64). Furthermore, Gal-3 protein expression levels are up-regulated under certain pathological conditions, such as neoplasms and inflammation (Chiariotti L. et al., Glycoconjugate Journal 2004 19, 441-449; Farhad M. et al., OncoImmunology 2018, 7:6, e1434467).

There are multiple lines of evidence supporting functional involvement of Gal-3 in the development of inflammatory/autoimmune diseases, such as asthma (Gao P. et al. Respir Res. 2013, 14:136; Rao S P et al. Front Med (Lausanne) 2017; 4:68), rheumatoid arthritis, multiple sclerosis, diabetes, plaque psoriasis (Lacina L. et al. Folia Biol (Praha) 2006; 52(1-2):10-5) atopic dermatitis (Saegusa J. et al. Am J Pathol. 2009, 174(3):922-31), endometriosis (Noel J C et al. Appl Immunohistochem Mol Morphol. 2011 19(3):253-7), or viral encephalitis (Liu F T et al., Ann N Y Acad Sci. 2012; 1253:80-91; Henderson N C, et al., Immunol Rev. 2009; 230(1):160-71; Li P et al., Cell 2016; 167:973-984). Recently Gal-3 has emerged as a key player of chronic inflammation and organ fibrogenesis development e.g. liver (Henderson N C et al., PNAS 2006; 103: 5060-5065; Hsu D K et al. Int J Cancer. 1999, 81(4):519-26), kidney (Henderson N C et al., Am. J. Pathol. 2008; 172:288-298; Dang Z. et al. Transplantation. 2012, 93(5):477-84), lung (Mackinnon A C et al., Am. J. Respir. Crit. Care Med 2012, 185: 537-546; Nishi Y. et al. Allergol Int. 2007, 56(1):57-65), heart (Thandavarayan R A et al. Biochem Pharmacol. 2008, 75(9):1797-806; Sharma U. et al. Am J Physiol Heart Circ Physiol. 2008; 294(3):H1226-32), as well as the nervous system (Burguillos M A et al. Cell Rep. 2015, 10(9):1626-1638), and in corneal neovascularization (Chen W S. Et al., Investigative Ophthalmology & Visual Science 2017, Vol. 58, 9-20). Additionally, Gal-3 was found to be associated with dermal thickening of keloid tissues (Arciniegas E. et al., The American Journal of dermatopathology 2019; 41(3): 193-204) and systemic sclerosis (SSc) especially with skin fibrosis and proliferative vasculopathy observed in such condition (Taniguchi T. et al. J Rheumatol. 2012, 39(3):539-44). Gal-3 was found to be up-regulated in patient suffering chronic kidney disease (CKD) associated-kidney failure, and especially in those affected by diabetes. Interestingly, data obtained from this patient population showed correlation between Gal-3 upregulation in glomeruli and the observed urinary protein excretion (Kikuchi Y. et al. Nephrol Dial Transplant. 2004, 19(3):602-7). Additionally, a recent prospective study from 2018 demonstrated that higher Gal-3 plasma levels are associated with an elevated risk of developing incident CKD, particularly among hypertension-suffering population (Rebholz C M. et al. Kidney Int. 2018 January; 93(1): 252-259). Gal-3 is highly elevated in cardiovascular diseases (Zhong X. et al. Clin Exp Pharmacol Physiol. 2019, 46(3):197-203), such as atherosclerosis (Nachtigal M. et al. Am J Pathol. 1998; 152(5):1199-208), coronary artery disease (Falcone C. et al. Int J Immunopathol Pharmacol 2011, 24(4):905-13), heart failure and thrombosis (Nachtigal M. et al., Am J Pathol. 1998; 152(5):

1199-208; Gehlken C. et al., Heart Fail Clin. 2018, 14(1): 75-92; DeRoo E P. et al., Blood. 2015, 125(11):1813-21). Gal-3 blood concentration is elevated in obese and diabetic patients and is associated with a higher risk for micro- and macro-vascular complication (such as heart failure, nephropathy/retinopathy, peripheral arterial disease, cerebrovascular event, or myocardial infarction) (Qi-hui-Jin et al. Chin Med J (Engl). 2013,126(11):2109-15). Gal-3 influences oncogenesis, cancer progression, and metastasis (Vuong L. et al., Cancer Res 2019 (79) (7) 1480-1492), and was shown to exert a role as a pro-tumor factor by acting within the micro tumor environment to suppress immune surveillance (Ruvolo P P. et al. Biochim Biophys Acta. 2016 March, 1863(3):427-437; Farhad M. et al. Oncoimmunology 2018 Feb. 20; 7(6):e1434467). Among the cancers that express high level of Gal-3 are found those affecting the thyroid gland, the central nervous system, the tongue, the breast, the gastric cancer, the head and neck squamous cell, the pancreas, the bladder, the kidney, the liver, the parathyroid, the salivary glands, but also lymphoma, carcinoma, non-small cell lung cancer, melanoma and neuroblastoma (Sciacchitano S. et al. Int J Mol Sci 2018 Jan. 26, 19(2):379).

Also, Gal-3 inhibition has been proposed to be beneficial in the treatment of COVID-19 (Caniglia J L et al. Peer J 2020, 8:e9392) and influenza H5N1 (Chen Y J et al. Am. J. Pathol. 2018, 188(4), 1031-1042) possibly due to anti-inflammatory effects.

Recently, Gal-3 inhibitors have shown to have positive effects when used in combination immunotherapy (Galectin Therapeutics. Press Release, Feb. 7, 2017) and idiopathic pulmonary fibrosis (Galecto Biotech. Press Release, Mar. 10, 2017) and in NASH cirrhosis (Dec. 5, 2017). WO20180209276, WO2018209255 and WO20190890080 disclose compounds having binding affinity with galectin proteins for the treatment of systemic insulin resistance disorders. Thus, Gal-3 inhibitors, alone or in combination with other therapies, may be useful for the prevention or treatment of diseases or disorders such as fibrosis of organs, cardiovascular diseases and disorders, acute kidney injury and chronic kidney disease, liver diseases and disorders, interstitial lung diseases and disorders, ocular diseases and disorders, cell proliferative diseases and cancers, inflammatory and autoimmune diseases and disorders, gastrointestinal tract diseases and disorders, pancreatic diseases and disorders, abnormal angiogenesis-associated diseases and disorders, brain-associated diseases and disorders, neuropathic pain and peripheral neuropathy, and/or transplant rejection.

Several publications and patent applications describe synthetic inhibitors of Gal-3 that are being explored as antifibrotic agents (see for example WO2005113568, WO2005113569, WO2014067986, WO2016120403, US20140099319, WO2019067702, WO2019075045, WO2014078655, WO2020078807 and WO2020078808).

Verteramo et al. (J. Am. Chem. Soc. 2019, 141, 5, 2012) discloses a comparative analysis of ligand binding to galectin-3C using two diastereomeric β-D-galactopyranoside ligands, which however are different from the present compounds by at least the absence of present mandatory substituent $Ar^2$. The same ligand was used by Caldararu et al. (Phys. Chem. Chem. Phys. 2019, 21, 18149) to study whether it is possible to obtain reliable entropies from crystallographic B-factors.

The present invention provides novel compounds of formula (I) which are Galectin-3 inhibitors. The present compounds may, thus, be useful for the prevention/prophylaxis or treatment of diseases and disorders where modulation of Gal-3 binding to its natural carbohydrate ligands is indicated.

1) In a first embodiment, the invention relates to a compound of the Formula (I),

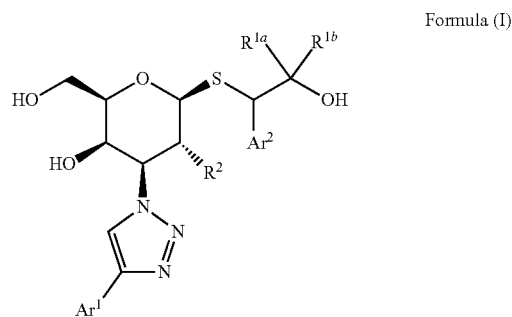

Formula (I)

wherein $Ar^1$ represents aryl (especially phenyl) which is mono-, di-, tri-, tetra-, or penta-substituted (especially mono, di- or tri-substituted), wherein the substituents are independently selected from halogen, methyl, cyano, and methoxy; [wherein in particular at least one of said substituents is attached in a meta- or in para-position of said phenyl; wherein, if present, such substituent in para-position is preferably selected from halogen, methyl, cyano, and methoxy; and, if present, such substituent in meta-position is preferably halogen]; or 5- or 6-membered heteroaryl (especially pyridinyl), wherein said 5- or 6-membered heteroaryl independently is unsubstituted, mono- or di-substituted, wherein the substituents are independently selected from halogen, methyl, cyano, and methoxy;

$Ar^2$ represents phenyl or 5- or 6-membered heteroaryl (especially thiophenyl, thiazolyl, oxazolyl, isoxazolyl, pyridinyl, or pyrazinyl; or, in addition, pyrazolyl, triazolyl, or pyridazinyl), wherein said phenyl or 5- or 6-membered heteroaryl independently is unsubstituted, mono-, di-, or tri-substituted wherein the substituents independently are $C_{1-6}$-alkyl, $C_{3-6}$-cycloalkyl (especially cyclopropyl), $C_{1-3}$-fluoroalkyl (especially trifluoromethyl), $C_{1-3}$-fluoroalkoxy, halogen, hydroxy-$C_{1-3}$-alkyl (especially 2-hydroxyethyl), or phenyl [notably, in case $Ar^2$ represents phenyl, one of said substituents is attached in ortho-position with regard to the point of attachment of $Ar^2$ to the rest of the molecule and the other substituent(s), if present, is/are attached in meta- or para-position with regard to the point of attachment of the rest of the molecule]; or naphthyl;

R$^{1a}$ represents hydrogen; and R$^{1b}$ represents
- —C$_{2-4}$-alkyl (especially ethyl); or
- —C$_{0-1}$-alkylene-Ar$^{1b}$, wherein Ar$^{1b}$ represents phenyl or 5- or 6-membered heteroaryl, wherein said phenyl or 5- or 6-membered heteroaryl independently is unsubstituted, mono- or di-substituted with methyl;

or R$^{1a}$ and R$^{1b}$ both represent hydrogen, methyl, ethyl, or n-propyl;

or R$^{1a}$ and R$^{1b}$ together with the carbon atom to which they are attached form a 3- to 6-membered ring selected from
- C$_{3-6}$-cycloalkylene, wherein said C$_{3-6}$-cycloalkylene independently is unsubstituted, mono-, or di-substituted, wherein the substituents independently are methyl or fluoro;
- tetrahydro-2H-pyran-4,4-diyl, which is unsubstituted, di-, or tetra-substituted with methyl;
- tetrahydro-2H-thiopyran-1,1-dioxide-4,4-diyl; or
- piperidine-4,4-diyl, pyrrolidine-3,3-diyl, or azetidine-3,3-diyl wherein the nitrogen of said piperidine, pyrrolidine or azetidine independently is unsubstituted, or substituted with —C$_{1-3}$-alkyl, —C$_{0-2}$-alkylene-C$_{3-6}$-cycloalkyl, or -L-R$^{N1}$ wherein
  -L- represents —CO—, —SO$_2$—, *—CO—NH—, *—CO—O—, or *—SO$_2$—NH—, and
  R$^{N1}$ represents —C$_{1-3}$-alkyl or —C$_{0-2}$-alkylene-C$_{3-6}$-cycloalkyl;
  (especially said piperidine is unsubstituted or substituted with methyl, —CO-methyl, —CO—O-methyl, —CO—NH-cyclopropyl, —SO$_2$-methyl, —SO$_2$-cyclopropyl, or —SO$_2$—NH-methyl; and said azetidine is substituted with —SO$_2$-methyl, —CO—O-methyl, or —CO—NH-cyclopropyl);
  wherein in the above groups the asterisks indicate the bond which is connected to the rest of the molecule; or R$^{1a}$ and R$^{1b}$ together with the carbon atom to which they are attached form a spiro-bicyclic ring system of the structure (S$^{1AB}$)

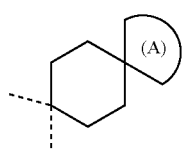

(S$^{1AB}$)

wherein ring (A) represents a 3- to 6-membered non-aromatic carbocyclic ring, wherein said 3- to 6-membered non-aromatic carbocyclic ring optionally contains one ring oxygen atom and wherein said 3- to 6-membered non-aromatic carbocyclic ring is unsubstituted or di-substituted with fluoro; and R$^2$ represents hydroxy or C$_{1-3}$-alkoxy (especially methoxy).

The compounds of Formula (I) contain five stereogenic or asymmetric centers, which are situated on the tetrahydropyran moiety and which are in the absolute configuration as drawn for Formula (I). In addition, the compounds of Formula (I) contain at least one, and possibly more, further stereogenic or asymmetric centers, such as one or more additional asymmetric carbon atoms. The compounds of Formula (I) may thus be present as mixtures of stereoisomers or preferably as pure stereoisomers. Mixtures of stereoisomers may be separated in a manner known to a person skilled in the art.

In case a particular compound (or generic structure) is designated as being in a certain absolute configuration, e.g. as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center.

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The present invention also includes isotopically labelled, especially $^2$H (deuterium) labelled compounds of Formula (I) according to embodiments 1) to 25), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of Formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of formula (I) are not isotopically labelled at all. Isotopically labelled compounds of Formula (I) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

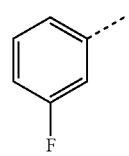

is a 3-fluorophenyl group.

Where the plural form is used for compounds, salts, pharmaceutical compositions, diseases and the like, this is intended to mean also a single compound, salt, or the like.

Any reference to compounds of Formula (I) according to embodiments 1) to 25) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of Formula (I), as defined in any one of embodiments 1) to 18), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

In this patent application, the compounds are named using IUPAC nomenclature, but can also be named using carbohydrate nomenclature. Thus, the moiety:

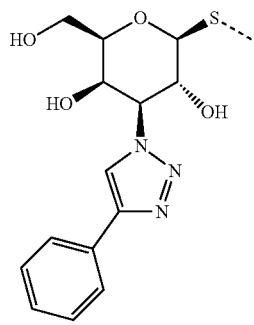

can be named (2S,3R,4S,5R,6R)-3,5-dihydroxy-6-(hydroxymethyl)-4-(4-phenyl-1H-1,2,3-triazol-1-yl)tetrahydro-2H-pyran-2-thiyl or, alternatively, 1,3-di-deoxy-3-[4-phenyl-1H-1,2,3-triazol-1-yl]-β-D-galactopyranoside-1-thiyl, wherein the absolute configuration of carbon atom carrying sulphur atom which is the point of attachment to the rest of the molecule is in (2S)—, respectively, beta-configuration. For example, compound (2S,3R,4S,5R,6R)-2-(((R)-(4-hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol is to be understood as also referring to: 1,3-di-deoxy-1-((1-methyl-4-hydroxy-piperidin-4-yl)-(3,5,6-trimethylpyrazin-2-yl)methyl-(R)-thio)-3-[4-(3,4,5-trifluorophenyl)-1H-1,2,3-triazol-1-yl]-β-D-galactopyranoside.

Whenever a substituent is denoted as optional, it is understood that such substituent may be absent (i.e. the respective residue is unsubstituted with regard to such optional substituent), in which case all positions having a free valency (to which such optional substituent could have been attached to; such as for example in an aromatic ring the ring carbon atoms and/or the ring nitrogen atoms having a free valency) are substituted with hydrogen where appropriate. Likewise, in case the term "optionally" is used in the context of (ring) heteroatom(s), the term means that either the respective optional heteroatom(s), or the like, are absent (i.e. a certain moiety does not contain heteroatom(s)/is a carbocycle/or the like), or the respective optional heteroatom(s), or the like, are present as explicitly defined. If not explicitly defined otherwise in the respective embodiment or claim, groups defined herein are unsubstituted.

The term "halogen" means fluorine, chlorine, or bromine, preferably fluorine or chlorine.

The term "alkyl", used alone or in combination, refers to a saturated straight or branched chain hydrocarbon group containing one to six carbon atoms. The term "$C_{x-y}$-alkyl" (x and y each being an integer), refers to an alkyl group as defined before, containing x to y carbon atoms. For example, a $C_{1-6}$-alkyl group contains from one to six carbon atoms. Representative examples of alkyl groups are methyl, ethyl, propyl, isopropyl, butyl, isobutyl, tert.-butyl, pentyl, 3-methyl-butyl, 2,2-dimethyl-propyl and 3,3-dimethyl-butyl. For avoidance of any doubt, in case a group is referred to as e.g. propyl or butyl, it is meant to be n-propyl, respectively n-butyl. Preferred is methyl.

The term "—$C_{x-y}$-alkylene-", used alone or in combination, refers to bivalently bound alkyl group as defined before containing x to y carbon atoms. The term "—$C_{0-y}$-alkylene-" refers to a direct bond, or to a —($C_{1-y}$)alkylene- as defined before. Preferably, the points of attachment of a —$C_{1-y}$-alkylene group are in 1,1-diyl, or in 1,2-diyl, or in 1,3-diyl arrangement. Preferably, the points of attachment of a —$C_{2-y}$-alkylene group are in 1,2-diyl or in 1,3-diyl arrangement. In case a $C_{0-y}$-alkylene group is used in combination with another substituent, the term means that either said substituent is linked through a $C_{1-y}$-alkylene group to the rest of the molecule, or it is directly attached to the rest of the molecule (i.e. a $C_0$-alkylene group represents a direct bond linking said substituent to the rest of the molecule). The alkylene group —$C_2H_4$— refers to —$CH_2$—$CH_2$— if not explicitly indicated otherwise.

The term "alkenyl", used alone or in combination, refers to a straight or branched hydrocarbon chain containing two to five carbon atoms and one carbon-carbon double bond. The term "$C_{x-y}$-alkenyl" (x and y each being an integer), refers to an alkenyl group as defined before containing x to y carbon atoms. For example, a $C_{2-5}$-alkenyl group contains from two to five carbon atoms.

The term "fluoroalkyl", used alone or in combination, refers to an alkyl group as defined before containing one to three carbon atoms in which one or more (and possibly all) hydrogen atoms have been replaced with fluorine. The term "$C_{x-y}$-fluoroalkyl" (x and y each being an integer) refers to a fluoroalkyl group as defined before containing x to y carbon atoms. For example, a $C_{1-3}$-fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $C_1$-fluoroalkyl groups such as trifluoromethyl.

The term "fluoroalkoxy", used alone or in combination, refers to an alkoxy group as defined before containing one to three carbon atoms in which one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example, a $C_{1-3}$-fluoroalkoxy group contains from one to three carbon atoms in which one to seven hydrogen atoms have been replaced with fluorine.

Representative examples of fluoroalkoxy groups include trifluoromethoxy, difluoromethoxy, 2-fluoroethoxy, 2,2-difluoroethoxy and 2,2,2-trifluoroethoxy.

The term "cycloalkyl", used alone or in combination, refers especially to a saturated monocyclic, or to a fused-, bridged-, or spiro-bicyclic hydrocarbon ring containing three to eight carbon atoms. The term "$C_{x-y}$-cycloalkyl" (x and y each being an integer), refers to a cycloalkyl group as defined before containing x to y carbon atoms. For example, a $C_{3-6}$-cycloalkyl group contains from three to six carbon atoms. Examples of cycloalkyl groups are cyclopropyl, cyclobutyl, cyclopentyl, cyclohexyl, and cycloheptyl.

The term "—$C_{x-y}$-cycloalkylene-", used alone or in combination, refers to bivalently bound cycloalkyl group as defined before containing x to y carbon atoms. Preferably, the points of attachment of any bivalently bound cycloalkyl group are in 1,1-diyl arrangement. Examples are cyclopropan-1,1-diyl, cyclobutan-1,1-diyl, cyclopentan-1,1-diyl; and cyclohexan-1,1-diyl, preferred is cyclohexan-1,1-diyl. In case "$R^{1a}$ and $R^{1b}$ together with the carbon atom to which they are attached form a $C_{3-6}$-cycloalkylene, wherein said $C_{3-6}$-cycloalkylene independently is unsubstituted, mono-, or di-substituted", the term especially refers to the above-listed groups which are unsubstituted or substituted as explicitly defined; particular examples are cyclobutane-1,1-diyl, cyclopentane-1,1-diyl, cyclohexane-1,1-diyl, 3-methylcyclobutane-1,1-diyl, 2,3-dimethylcyclobutane-1,1-diyl, 3,3-dimethylcyclobutane-1,1-diyl, 3,3-difluorocyclobutane-1,1-diyl, or 4,4-difluorocyclohexane-1,1-diyl; especially 4,4-difluorocyclohexane-1,1-diyl.

The term "alkoxy", used alone or in combination, refers to an alkyl-O— group wherein the alkyl group is as defined before. The term "$C_{x-y}$-alkoxy" (x and y each being an integer) refers to an alkoxy group as defined before containing x to y carbon atoms. Preferred are ethoxy and especially methoxy. In case $R^2$ represents "$C_{1-3}$-alkoxy", the term preferably means methoxy or ethoxy, especially methoxy.

The term "heterocyclyl", used alone or in combination, and if not explicitly defined in a broader or more narrow way, refers to a saturated or unsaturated non-aromatic monocyclic hydrocarbon ring containing one or two ring heteroatoms independently selected from nitrogen, sulfur, and oxygen (especially one oxygen atom, one sulfur atom, one nitrogen atom, two nitrogen atoms, two oxygen atoms, one nitrogen atom and one oxygen atom). The term "$C_{x-y}$-heterocyclyl" refers to such a heterocycle containing x to y ring atoms. Heterocyclyl groups are unsubstituted or substituted as explicitly defined.

The term "aryl", used alone or in combination, means phenyl or naphthyl, preferably phenyl, wherein said aryl group is unsubstituted or substituted as explicitly defined.

The term "heteroaryl", used alone or in combination, and if not explicitly defined in a broader or more narrow way, means a 5- to 10-membered monocyclic or bicyclic aromatic ring containing one to a maximum of four heteroatoms, each independently selected from oxygen, nitrogen and sulfur. Representative examples of such heteroaryl groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; 6-membered heteroaryl groups such as pyridinyl, pyrimidinyl, pyridazinyl, pyrazinyl; and 8- to 10-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, thienopyridinyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined. For the group $Ar^2$ representing "5- or 6-membered heteroaryl", the term especially means thiophenyl, thiazolyl, oxazolyl, isoxazolyl, pyridinyl, or pyrazinyl; or in addition pyrazolyl, triazolyl, pyridazinyl; in particular thiophen-3-yl, thiazol-4-yl, oxazol-4-yl, isoxazol-3-yl, isoxazol-4-yl, pyridin-2-yl, pyridin-3-yl, or pyrazin-2-yl; or in addition 1H-pyrazol-5-yl, 1H-1,2,3-triazol-5-yl, or pyridazin-3-yl. The term "one substituent is attached in ortho-position with regard to the point of attachment of $Ar^2$ to the rest of the molecule" in the context of a heteroaryl group such as $Ar^2$ means that the respective substituents are attached in a relative 1,2-arrangement.

In case $Ar^1$ represents "5- or 6-membered heteroaryl", the term means the above-listed groups, especially pyridinyl; in particular pyridin-3-yl; wherein said 5- or 6-membered heteroaryl group is unsubstituted or substituted as explicitly defined.

In case $R^{1a}$ and $R^{1b}$ together with the carbon atom to which they are attached form a "spiro-bicyclic ring system of the structure ($S^{1AB}$)", such structure ($S^{1AB}$) especially refers to 3-oxaspiro[5.5]undecane-9,9-diyl.

The term "cyano" refers to a group —CN.

The term "oxo" refers to a group =O which is preferably attached to a chain or ring carbon or sulfur atom as for example in a carbonyl group —(CO)—, or a sulfonyl group —(SO$_2$)—.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

Further embodiments of the invention are presented hereinafter:

2) A second embodiment relates to the compounds of Formula (I) according to embodiment 1) which are also compounds of Formula ($I_R$), Formula (I$_R$)

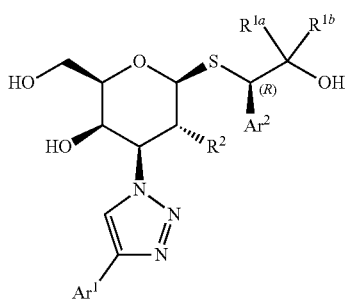

wherein the carbon atom to which the group Ar$^2$ is attached is in the absolute configuration as drawn in Formula (I$_R$) [i.e. it is in absolute (R)-configuration]; wherein R$^{1a}$, R$^{1b}$, R$^2$, Ar$^1$, and Ar$^2$ are as defined in embodiment 1).

3) Another embodiment relates to compounds according to embodiments 1) or 2), wherein Ar$^1$ represents phenyl which is mono-, di- or tri-substituted, wherein the substituents are independently selected from halogen, methyl, cyano, and methoxy;
wherein at least one of said substituents is attached in a meta- or in para-position of said phenyl,
wherein, if present, the substituent in para-position is preferably selected from halogen, methyl, cyano, and methoxy; and
wherein, if present, the substituent in meta-position is preferably halogen.

4) Another embodiment relates to compounds according to embodiments 1) or 2), wherein Ar$^1$ represents phenyl which is mono-, di- or tri-substituted, wherein
one of said substituents is attached in meta-position of said phenyl, wherein said substituent is halogen; and the remaining substituent(s), if present, is/are halogen (especially fluoro); or
one of said substituents is attached in para-position of said phenyl, wherein said substituent is independently selected from methyl, cyano, and methoxy; and
the remaining substituent(s), if present, is/are halogen (especially fluoro).

5) Another embodiment relates to compounds according to embodiments 1) or 2), wherein Ar$^1$ represents a phenyl group of the structure

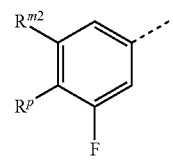

(Ar-I)

wherein
R$^{m2}$ represents hydrogen or fluoro; and
R$^p$ represents independently halogen (especially fluoro or chloro), methyl, cyano, or methoxy (notably R$^p$ represents fluoro, chloro, or methyl); or
R$^{m2}$ represents hydrogen or fluoro; and
R$^p$ represents hydrogen.

6) Another embodiment relates to compounds according to embodiments 1) or 2), wherein Ar$^1$ represents a phenyl group of the structure (Ar-I)

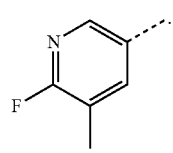

wherein
R$^{m2}$ represents halogen (especially fluoro); and
R$^p$ represents hydrogen, halogen (especially fluoro or chloro), methyl, cyano, or methoxy (notably R$^p$ represents fluoro, chloro, or methyl).

7) Another embodiment relates to compounds according to embodiments 1) or 2), wherein Ar$^1$ represents:

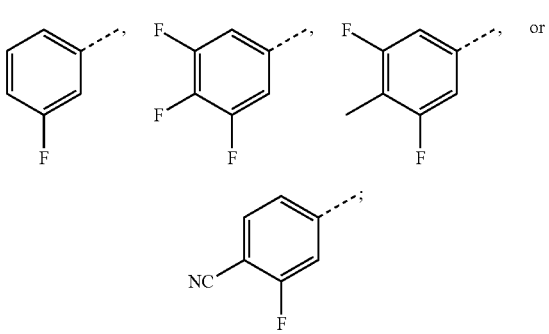

or, in addition, Ar$^1$ represents:

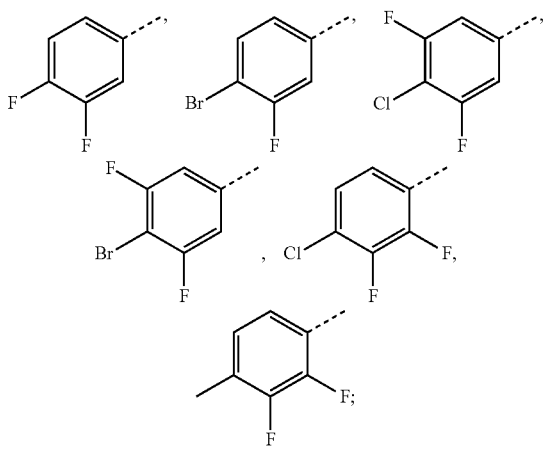

or, in addition, Ar$^1$ represents:

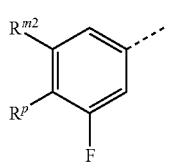

In a sub-embodiment Ar¹ especially represents

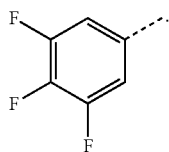

8) Another embodiment relates to compounds according to any one of embodiments 1) to 7), wherein Ar² represents phenyl which is mono-, di-, or tri-substituted (especially mono-, or di-substituted); wherein
 one substituent is attached in ortho-position with regard to the point of attachment of Ar² to the rest of the molecule; wherein said substituent is $C_{1-6}$-alkyl, $C_{3-6}$-cycloalkyl (especially cyclopropyl), $C_{1-3}$-fluoroalkyl (especially trifluoromethyl), $C_{1-3}$-fluoroalkoxy, halogen, hydroxy-$C_{1-3}$-alkyl (especially 2-hydroxyethyl), or phenyl;
 and the other substituent(s), if present, is/are attached in meta- and/or para-position with regard to the point of attachment of Ar² to the rest of the molecule; wherein the substituent(s) independently are $C_{1-6}$-alkyl, $C_{3-6}$-cycloalkyl (especially cyclopropyl), $C_{1-3}$-fluoroalkyl (especially trifluoromethyl), or halogen; or
 5- or 6-membered heteroaryl (especially thiophenyl, thiazolyl, oxazolyl, isoxazolyl, pyridinyl, or pyrazinyl; or, in addition, pyrazolyl, triazolyl, or pyridazinyl), wherein said 5- or 6-membered heteroaryl independently is mono-, di-, or tri-substituted; wherein
 one substituent is attached in ortho-position with regard to the point of attachment of Ar² to the rest of the molecule; wherein said substituent is $C_{1-6}$-alkyl (especially methyl), $C_{3-6}$-cycloalkyl (especially cyclopropyl), or $C_{1-3}$-fluoroalkyl (especially trifluoromethyl) [especially such ortho-substituent is methyl or trifluoromethyl];
 and the other substituent(s), if present, is/are independently $C_{1-6}$-alkyl, $C_{3-6}$-cycloalkyl (especially cyclopropyl), $C_{1-3}$-fluoroalkyl (especially trifluoromethyl), or halogen.

9) Another embodiment relates to compounds according to any one of embodiments 1) to 7), wherein Ar² represents phenyl which is mono-, or di-substituted; wherein
 one substituent is attached in ortho-position with regard to the point of attachment of Ar² to the rest of the molecule; wherein said substituent is $C_{1-6}$-alkyl, cyclopropyl, trifluoromethyl, halogen, 2-hydroxyethyl, or phenyl;
 and the other substituent, if present, is attached in meta-position with regard to the point of attachment of Ar² to the rest of the molecule; wherein the substituent independently is $C_{1-3}$-alkyl, cyclopropyl, trifluoromethyl, or halogen; or
 5- or 6-membered heteroaryl selected from thiophenyl, thiazolyl, oxazolyl, isoxazolyl, pyridinyl, and pyrazinyl; or, in addition, pyrazolyl, triazolyl, or pyridazinyl (especially isoxazolyl, pyridinyl, and pyrazinyl), wherein said 5- or 6-membered heteroaryl independently is mono-, di-, or tri-substituted; wherein
 one substituent is attached in ortho-position with regard to the point of attachment of Ar² to the rest of the molecule; wherein said substituent is $C_{1-6}$-alkyl (especially methyl), cyclopropyl, or trifluoromethyl;
 and the other substituent(s), if present, independently is/are methyl.

10) Another embodiment relates to compounds according to any one of embodiments 1) to 7), wherein Ar² represents a 5- or 6-membered heteroaryl (especially thiophenyl, thiazolyl, oxazolyl, isoxazolyl, pyridinyl, or pyrazinyl; or, in addition, pyrazolyl, triazolyl, or pyridazinyl), wherein said 5- or 6-membered heteroaryl independently is unsubstituted, mono-, di-, or tri-substituted wherein the substituents independently are $C_{1-6}$-alkyl, $C_{3-6}$-cycloalkyl (especially cyclopropyl), $C_{1-3}$-fluoroalkyl (especially trifluoromethyl), $C_{1-3}$-fluoroalkoxy, or halogen.

In a sub-embodiment, said 5- or 6-membered heteroaryl is selected from isoxazolyl, pyridinyl, and pyrazinyl, wherein said 5- or 6-membered heteroaryl independently is mono-, di-, or tri-substituted; wherein
 one substituent is attached in ortho-position with regard to the point of attachment of Ar² to the rest of the molecule; wherein said substituent is $C_{1-6}$-alkyl (especially methyl), cyclopropyl, or trifluoromethyl;
 and the other substituent(s), if present, independently is/are methyl.

11) Another embodiment relates to compounds according to any one of embodiments 1) to 7), wherein Ar² represents:

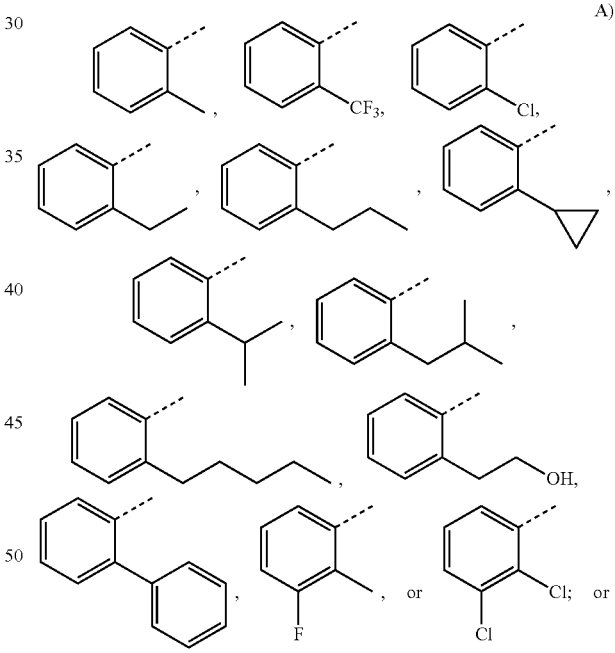

A)

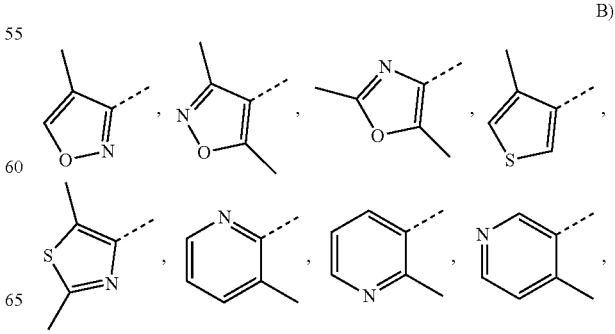

B)

-continued
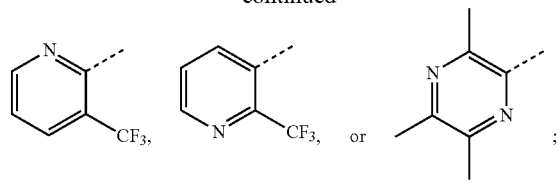
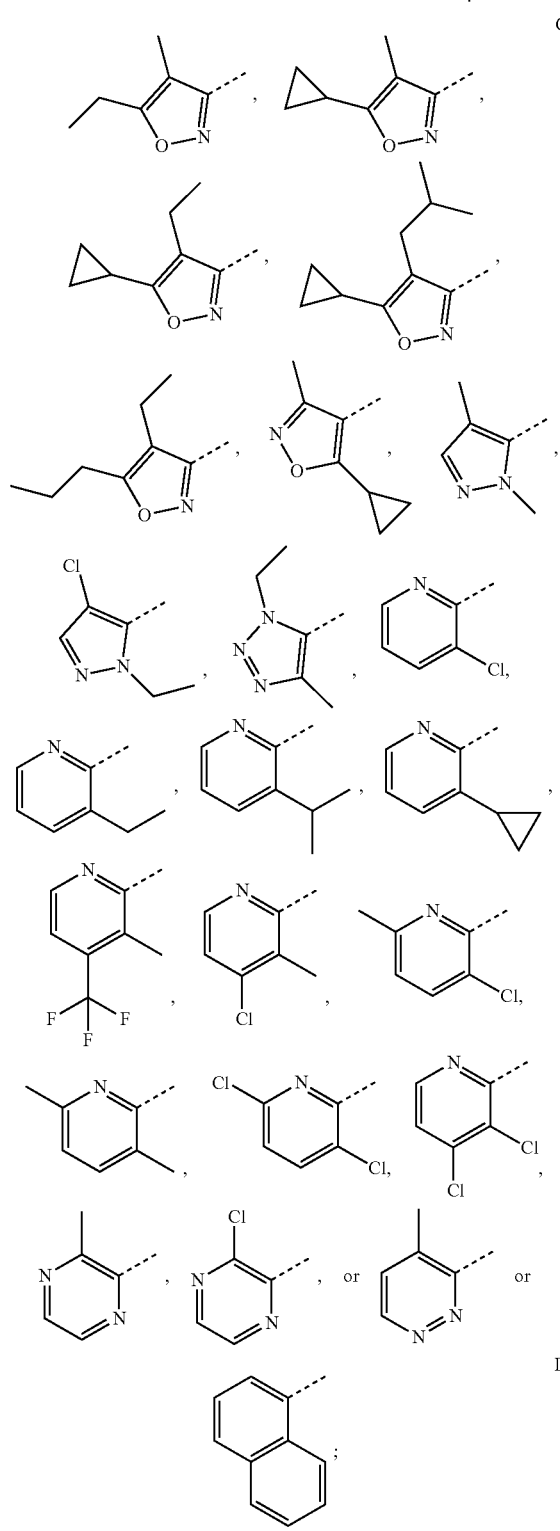
wherein each of the groups A) to D) form a particular sub-embodiment; and wherein another sub-embodiment refers to groups A), B) and/or D).
12) Another embodiment relates to compounds according to any one of embodiments 1) to 7), wherein $Ar^2$ represents:
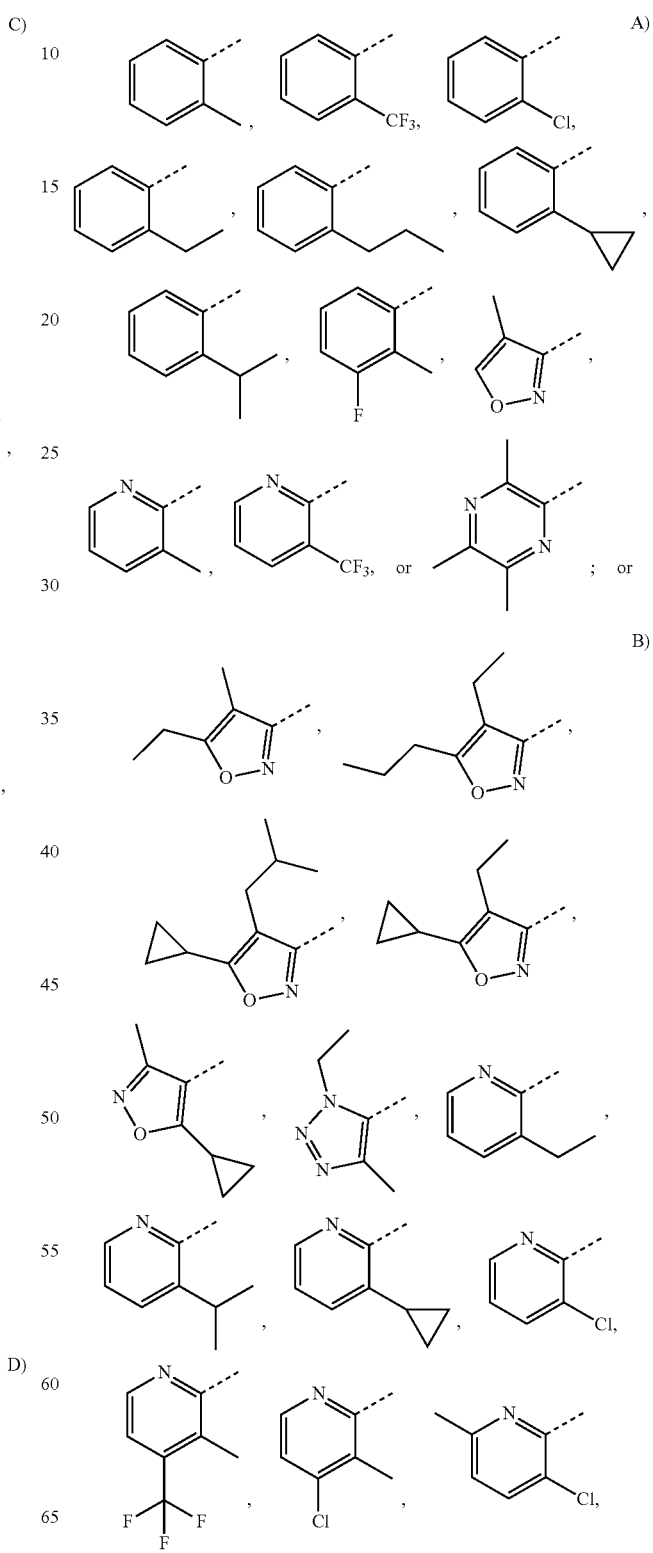

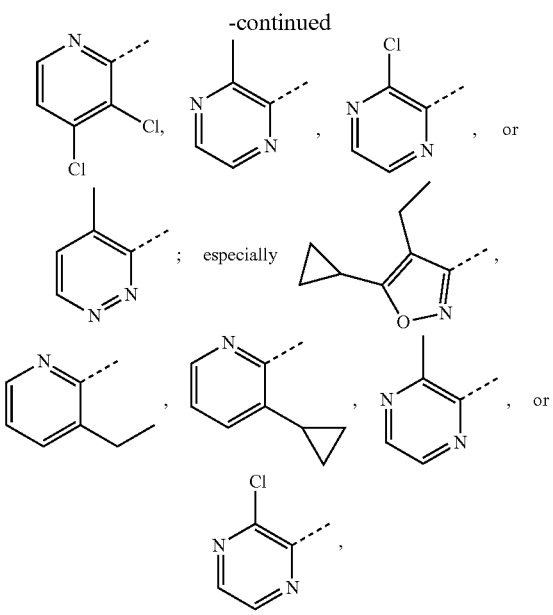

wherein each of the groups A) and B) form a particular sub-embodiment.

13) Another embodiment relates to compounds according to any one of embodiments 1) to 12), wherein
$R^{1a}$ represents hydrogen; and $R^{1b}$ represents
—$C_{2-4}$-alkyl (especially ethyl);
phenyl which is unsubstituted, mono- or di-substituted with methyl; or
or $R^{1a}$ and $R^{1b}$ both represent methyl, ethyl, or n-propyl;
or $R^{1a}$ and $R^{1b}$ together with the carbon atom to which they are attached form a 3- to 6-membered ring selected from
$C_{4-6}$-cycloalkylene, wherein said cycloalkyl independently is unsubstituted, mono-, or di-substituted, wherein the substituents independently are methyl or fluoro (especially cyclobutane-1,1-diyl, cyclopentane-1,1-diyl, cyclohexane-1,1-diyl, 3-methylcyclobutane-1,1-diyl, 2,3-dimethylcyclobutane-1,1-diyl, 3,3-dimethylcyclobutane-1,1-diyl, 3,3-difluorocyclobutane-1,1-diyl, or 4,4-difluorocyclohexane-1,1-diyl);
tetrahydro-2H-pyran-4,4-diyl; 2,2-dimethyltetrahydro-2H-pyran-4,4-diyl, or 2,2,6,6-tetramethyltetrahydro-2H-pyran-4,4-diyl;
tetrahydro-2H-thiopyran-1,1-dioxide-4,4-diyl;
piperidine-4,4-diyl, wherein the nitrogen of said piperidine is unsubstituted, or substituted with —$C_{1-3}$-alkyl, —CO—$C_{1-3}$-alkyl, —CO—O—$C_{1-3}$-alkyl, —CO—NH-cyclopropyl, —$SO_2$—$C_{1-3}$-alkyl, —$SO_2$-cyclopropyl, or —$SO_2$—NH—$C_{1-3}$-alkyl (especially said piperidine is unsubstituted or substituted with methyl, —CO-methyl, —CO-methoxy, —CO—NH-cyclopropyl, —$SO_2$-methyl, —$SO_2$-cyclopropyl, or —$SO_2$—NH-methyl); or
azetidine-3,3-diyl, wherein the nitrogen of said azetidine is unsubstituted, or substituted with —$SO_2$—$C_{1-3}$-alkyl, —CO—O—$C_{1-3}$-alkyl, or —CO—NH-cyclopropyl; or
$R^{1a}$ and $R^{1b}$ together with the carbon atom to which they are attached form a spiro-bicyclic ring system of the structure:

14) Another embodiment relates to compounds according to any one of embodiments 1) to 12), wherein $R^{1a}$ represents hydrogen; and $R^{1b}$ represents
—$C_{2-4}$-alkyl (especially ethyl), or
phenyl which is unsubstituted, mono- or di-substituted with methyl.

15) Another embodiment relates to compounds according to any one of embodiments 1) to 12), wherein $R^{1a}$ and $R^{1b}$ both represent a methyl, ethyl, or n-propyl (especially methyl).

16) Another embodiment relates to compounds according to any one of embodiments 1) to 12), wherein $R^{1a}$ and $R^{1b}$ together with the carbon atom to which they are attached form a 4- to 6-membered ring selected from
$C_{4-6}$-cycloalkylene, wherein said cycloalkyl independently is unsubstituted, mono-, or di-substituted, wherein the substituents independently are methyl or fluoro (especially cyclobutane-1,1-diyl, cyclopentane-1,1-diyl, cyclohexane-1,1-diyl, 3-methylcyclobutane-1,1-diyl, 2,3-dimethylcyclobutane-1,1-diyl, 3,3-dimethylcyclobutane-1,1-diyl, 3,3-difluorocyclobutane-1,1-diyl, or 4,4-difluorocyclohexane-1,1-diyl);
tetrahydro-2H-pyran-4,4-diyl, 2,2-dimethyltetrahydro-2H-pyran-4,4-diyl, or 2,2,6,6-tetramethyltetrahydro-2H-pyran-4,4-diyl; or
piperidine-4,4-diyl, wherein the nitrogen of said piperidine is unsubstituted or substituted with —$C_{1-3}$-alkyl, —CO—$C_{1-3}$-alkyl, —CO—O—$C_{1-3}$-alkyl, —CO—NH-cyclopropyl, —$SO_2$—$C_{1-3}$-alkyl, —$SO_2$-cyclopropyl, or —$SO_2$—NH—$C_{1-3}$-alkyl (especially said piperidine is unsubstituted or substituted with methyl, —CO-methyl, —CO-methoxy, —CO—NH-cyclopropyl, —$SO_2$-methyl, —$SO_2$-cyclopropyl, or —$SO_2$—NH-methyl).

17) Another embodiment relates to compounds according to any one of embodiments 1) to 16), wherein $R^2$ represents methoxy.

18) Another embodiment relates to compounds according to any one of embodiments 1) to 16), wherein $R^2$ represents hydroxy.

19) The invention, thus, relates to compounds of the Formula (I) as defined in embodiment 1), or to such compounds further limited by the characteristics of any one of embodiments 2) to 18), under consideration of their respective dependencies; to pharmaceutically acceptable salts thereof; and to the use of such compounds as further described herein below. For avoidance of any doubt, especially the following embodiments relating to the compounds of Formula (I) are thus possible and intended and herewith specifically disclosed in individualized form:
1, 2+1, 3+1, 3+2+1, 4+1, 4+2+1, 5+1, 5+2+1, 6+1, 6+2+1, 7+1, 7+2+1, 8+1, 8+2+1, 8+3+1, 8+3+2+1, 8+4+1, 8+4+2+1, 8+5+1, 8+5+2+1, 8+6+1, 8+6+2+1, 8+7+1, 8+7+2+1, 9+1, 9+2+1, 9+3+1, 9+3+2+1, 9+4+1, 9+4+2+1, 9+5+1, 9+5+2+1, 9+6+1, 9+6+2+1, 9+7+1, 9+7+2+1, 10+1, 10+2+1, 10+3+1, 10+3+2+1, 10+4+1, 10+4+2+1, 10+5+1, 10+5+2+1, 10+6+1, 10+6+2+1, 10+7+1, 10+7+2+1, 11+1, 11+2+1, 11+3+1, 11+3+2+1, 11+4+1, 11+4+2+1, 11+5+1, 11+5+

2+1, 11+6+1, 11+6+2+1, 11+7+1, 11+7+2+1, 12+1, 12+2+1, 12+3+1, 12+3+2+1, 12+4+1, 12+4+2+1, 12+5+1, 12+5+2+1, 12+6+1, 12+6+2+1, 12+7+1, 12+7+2+1, 13+1, 13+2+1, 13+3+1, 13+3+2+1, 13+4+1, 13+4+2+1, 13+5+1, 13+5+2+1, 13+6+1, 13+6+2+1, 13+7+1, 13+7+2+1, 13+8+1, 13+8+2+1, 13+8+3+1, 13+8+3+2+1, 13+8+4+1, 13+8+4+2+1, 13+8+5+1, 13+8+5+2+1, 13+8+6+1, 13+8+6+2+1, 13+8+7+1, 13+8+7+2+1, 13+9+1, 13+9+2+1, 13+9+3+1, 13+9+3+2+1, 13+9+4+1, 13+9+4+2+1, 13+9+5+1, 13+9+5+2+1, 13+9+6+1, 13+9+6+2+1, 13+9+7+1, 13+9+7+2+1, 13+10+1, 13+10+2+1, 13+10+3+1, 13+10+3+2+1, 13+10+4+1, 13+10+4+2+1, 13+10+5+1, 13+10+5+2+1, 13+10+6+1, 13+10+6+2+1, 13+10+7+1, 13+10+7+2+1, 13+11+1, 13+11+2+1, 13+11+3+1, 13+11+3+2+1, 13+11+4+1, 13+11+4+2+1, 13+11+5+1, 13+11+5+2+1, 13+11+6+1, 13+11+6+2+1, 13+11+7+1, 13+11+7+2+1, 13+12+1, 13+12+2+1, 13+12+3+1, 13+12+3+2+1, 13+12+4+1, 13+12+4+2+1, 13+12+5+1, 13+12+5+2+1, 13+12+6+1, 13+12+6+2+1, 13+12+7+1, 13+12+7+2+1, 14+1, 14+2+1, 14+3+1, 14+3+2+1, 14+4+1, 14+4+2+1, 14+5+1, 14+5+2+1, 14+6+1, 14+6+2+1, 14+7+1, 14+7+2+1, 14+8+1, 14+8+2+1, 14+8+3+1, 14+8+3+2+1, 14+8+4+1, 14+8+4+2+1, 14+8+5+1, 14+8+5+2+1, 14+8+6+1, 14+8+6+2+1, 14+8+7+1, 14+8+7+2+1, 14+9+1, 14+9+2+1, 14+9+3+1, 14+9+3+2+1, 14+9+4+1, 14+9+4+2+1, 14+9+5+1, 14+9+5+2+1, 14+9+6+1, 14+9+6+2+1, 14+9+7+1, 14+9+7+2+1, 14+10+1, 14+10+2+1, 14+10+3+1, 14+10+3+2+1, 14+10+4+1, 14+10+4+2+1, 14+10+5+1, 14+10+5+2+1, 14+10+6+1, 14+10+6+2+1, 14+10+7+1, 14+10+7+2+1, 14+11+1, 14+11+2+1, 14+11+3+1, 14+11+3+2+1, 14+11+4+1, 14+11+4+2+1, 14+11+5+1, 14+11+5+2+1, 14+11+6+1, 14+11+6+2+1, 14+11+7+1, 14+11+7+2+1, 14+12+1, 14+12+2+1, 14+12+3+1, 14+12+3+2+1, 14+12+4+1, 14+12+4+2+1, 14+12+5+1, 14+12+5+2+1, 14+12+6+1, 14+12+6+2+1, 14+12+7+1, 14+12+7+2+1, 15+1, 15+2+1, 15+3+1, 15+3+2+1, 15+4+1, 15+4+2+1, 15+5+1, 15+5+2+1, 15+6+1, 15+6+2+1, 15+7+1, 15+7+2+1, 15+8+1, 15+8+2+1, 15+8+3+1, 15+8+3+2+1, 15+8+4+1, 15+8+4+2+1, 15+8+5+1, 15+8+5+2+1, 15+8+6+1, 15+8+6+2+1, 15+8+7+1, 15+8+7+2+1, 15+9+1, 15+9+2+1, 15+9+3+1, 15+9+3+2+1, 15+9+4+1, 15+9+4+2+1, 15+9+5+1, 15+9+5+2+1, 15+9+6+1, 15+9+6+2+1, 15+9+7+1, 15+9+7+2+1, 15+10+1, 15+10+2+1, 15+10+3+1, 15+10+3+2+1, 15+10+4+1, 15+10+4+2+1, 15+10+5+1, 15+10+5+2+1, 15+10+6+1, 15+10+6+2+1, 15+10+7+1, 15+10+7+2+1, 15+11+1, 15+11+2+1, 15+11+3+1, 15+11+3+2+1, 15+11+4+1, 15+11+4+2+1, 15+11+5+1, 15+11+5+2+1, 15+11+6+1, 15+11+6+2+1, 15+11+7+1, 15+11+7+2+1, 15+12+1, 15+12+2+1, 15+12+3+1, 15+12+3+2+1, 15+12+4+1, 15+12+4+2+1, 15+12+5+1, 15+12+5+2+1, 15+12+6+1, 15+12+6+2+1, 15+12+7+1, 15+12+7+2+1, 16+1, 16+2+1, 16+3+1, 16+3+2+1, 16+4+1, 16+4+2+1, 16+5+1, 16+5+2+1, 16+6+1, 16+6+2+1, 16+7+1, 16+7+2+1, 16+8+1, 16+8+2+1, 16+8+3+1, 16+8+3+2+1, 16+8+4+1, 16+8+4+2+1, 16+8+5+1, 16+8+5+2+1, 16+8+6+1, 16+8+6+2+1, 16+8+7+1, 16+8+7+2+1, 16+9+1, 16+9+2+1, 16+9+3+1, 16+9+3+2+1, 16+9+4+1, 16+9+4+2+1, 16+9+5+1, 16+9+5+2+1, 16+9+6+1, 16+9+6+2+1, 16+9+7+1, 16+9+7+2+1, 16+10+1, 16+10+2+1, 16+10+3+1, 16+10+3+2+1, 16+10+4+1, 16+10+4+2+1, 16+10+5+1, 16+10+5+2+1, 16+10+6+1, 16+10+6+2+1, 16+10+7+1, 16+10+7+2+1, 16+11+1, 16+11+2+1, 16+11+3+1, 16+11+3+2+1, 16+11+4+1, 16+11+4+2+1, 16+11+5+1, 16+11+5+2+1, 16+11+6+1, 16+11+6+2+1, 16+11+7+1, 16+11+7+2+1, 16+12+1, 16+12+2+1, 16+12+3+1, 16+12+3+2+1, 16+12+4+1, 16+12+4+2+1, 16+12+5+1, 16+12+5+2+1, 16+12+6+1, 16+12+6+2+1, 16+12+7+1, 16+12+7+2+1, 17+1, 17+2+1, 17+3+1, 17+3+2+1, 17+4+1, 17+4+2+1, 17+5+1, 17+5+2+1, 17+6+1, 17+6+2+1, 17+7+1, 17+7+2+1, 17+8+1, 17+8+2+1, 17+8+3+1, 17+8+3+2+1, 17+8+4+1, 17+8+4+2+1, 17+8+5+1, 17+8+5+2+1, 17+8+6+1, 17+8+6+2+1, 17+8+7+1, 17+8+7+2+1, 17+9+1, 17+9+2+1, 17+9+3+1, 17+9+3+2+1, 17+9+4+1, 17+9+4+2+1, 17+9+5+1, 17+9+5+2+1, 17+9+6+1, 17+9+6+2+1, 17+9+7+1, 17+9+7+2+1, 17+10+1, 17+10+2+1, 17+10+3+1, 17+10+3+2+1, 17+10+4+1, 17+10+4+2+1, 17+10+5+1, 17+10+5+2+1, 17+10+6+1, 17+10+6+2+1, 17+10+7+1, 17+10+7+2+1, 17+11+1, 17+11+2+1, 17+11+3+1, 17+11+3+2+1, 17+11+4+1, 17+11+4+2+1, 17+11+5+1, 17+11+5+2+1, 17+11+6+1, 17+11+6+2+1, 17+11+7+1, 17+11+7+2+1, 17+12+1, 17+12+2+1, 17+12+3+1, 17+12+3+2+1, 17+12+4+1, 17+12+4+2+1, 17+12+5+1, 17+12+5+2+1, 17+12+6+1, 17+12+6+2+1, 17+12+7+1, 17+12+7+2+1, 17+13+1, 17+13+2+1, 17+13+3+1, 17+13+3+2+1, 17+13+4+1, 17+13+4+2+1, 17+13+5+1, 17+13+5+2+1, 17+13+6+1, 17+13+6+2+1, 17+13+7+1, 17+13+7+2+1, 17+13+8+1, 17+13+8+2+1, 17+13+8+3+1, 17+13+8+3+2+1, 17+13+8+4+1, 17+13+8+4+2+1, 17+13+8+5+1, 17+13+8+5+2+1, 17+13+8+6+1, 17+13+8+6+2+1, 17+13+8+7+1, 17+13+8+7+2+1, 17+13+9+1, 17+13+9+2+1, 17+13+9+3+1, 17+13+9+3+2+1, 17+13+9+4+1, 17+13+9+4+2+1, 17+13+9+5+1, 17+13+9+5+2+1, 17+13+9+6+1, 17+13+9+6+2+1, 17+13+9+7+1, 17+13+9+7+2+1, 17+13+10+1, 17+13+10+2+1, 17+13+10+3+1, 17+13+10+3+2+1, 17+13+10+4+1, 17+13+10+4+2+1, 17+13+10+5+1, 17+13+10+5+2+1, 17+13+10+6+1, 17+13+10+6+2+1, 17+13+10+7+1, 17+13+10+7+2+1, 17+13+11+1, 17+13+11+2+1, 17+13+11+3+1, 17+13+11+3+2+1, 17+13+11+4+1, 17+13+11+4+2+1, 17+13+11+5+1, 17+13+11+5+2+1, 17+13+11+6+1, 17+13+11+6+2+1, 17+13+11+7+1, 17+13+11+7+2+1, 17+13+12+1, 17+13+12+2+1, 17+13+12+3+1, 17+13+12+3+2+1, 17+13+12+4+1, 17+13+12+4+2+1, 17+13+12+5+1, 17+13+12+5+2+1, 17+13+12+6+1, 17+13+12+6+2+1, 17+13+12+7+1, 17+13+12+7+2+1, 17+14+1, 17+14+2+1, 17+14+3+1, 17+14+3+2+1, 17+14+4+1, 17+14+4+2+1, 17+14+5+1, 17+14+5+2+1, 17+14+6+1, 17+14+6+2+1, 17+14+7+1, 17+14+7+2+1, 17+14+8+1, 17+14+8+2+1, 17+14+8+3+1, 17+14+8+3+2+1, 17+14+8+4+1, 17+14+8+4+2+1, 17+14+8+5+1, 17+14+8+5+2+1, 17+14+8+6+1, 17+14+8+6+2+1, 17+14+8+7+1, 17+14+8+7+2+1, 17+14+9+1, 17+14+9+2+1, 17+14+9+3+1, 17+14+9+3+2+1, 17+14+9+4+1, 17+14+9+4+2+1, 17+14+9+5+1, 17+14+9+5+2+1, 17+14+9+6+1, 17+14+9+6+2+1, 17+14+9+7+1, 17+14+9+7+2+1, 17+14+10+1, 17+14+10+2+1, 17+14+10+3+1, 17+14+10+3+2+1, 17+14+10+4+1, 17+14+10+4+2+1, 17+14+10+5+1, 17+14+10+5+2+1, 17+14+10+6+1, 17+14+10+6+2+1, 17+14+10+7+1, 17+14+10+7+2+1, 17+14+11+1, 17+14+11+2+1, 17+14+11+3+1, 17+14+11+3+2+1, 17+14+11+4+1, 17+14+11+4+2+1, 17+14+11+5+1, 17+14+11+5+2+1, 17+14+11+6+1, 17+14+11+6+2+1, 17+14+11+7+1, 17+14+11+7+2+1, 17+14+12+1, 17+14+12+2+1, 17+14+12+3+1, 17+14+12+3+2+1, 17+14+12+4+1, 17+14+12+4+2+1, 17+14+12+5+1, 17+14+12+5+2+1, 17+14+12+6+1, 17+14+12+6+2+1, 17+14+12+7+1, 17+14+12+7+2+1, 17+15+1, 17+15+2+1, 17+15+3+1, 17+15+3+2+1, 17+15+4+1, 17+15+4+2+1, 17+15+5+1, 17+15+5+2+1, 17+15+6+1, 17+15+6+2+1, 17+15+7+1, 17+15+7+2+1, 17+15+8+1, 17+15+8+2+1, 17+15+8+3+1, 17+15+8+3+2+1, 17+15+8+4+1, 17+15+8+4+2+1, 17+15+8+5+1, 17+15+8+5+2+1, 17+15+8+6+1, 17+15+8+6+2+1, 17+15+8+7+1, 17+15+8+7+2+1, 17+15+9+1, 17+15+9+2+1, 17+15+9+3+1, 17+15+9+3+2+1, 17+15+9+4+1, 17+15+9+4+2+1, 17+15+9+5+1, 17+15+9+5+2+1, 17+15+9+6+1, 17+15+9+6+2+1, 17+15+9+7+1, 17+15+9+7+2+1, 17+15+

10+1, 17+15+10+2+1, 17+15+10+3+1, 17+15+10+3+2+1, 17+15+10+4+1, 17+15+10+4+2+1, 17+15+10+5+1, 17+15+10+5+2+1, 17+15+10+6+1, 17+15+10+6+2+1, 17+15+10+7+1, 17+15+10+7+2+1, 17+15+11+1, 17+15+11+2+1, 17+15+11+3+1, 17+15+11+3+2+1, 17+15+11+4+1, 17+15+11+4+2+1, 17+15+11+5+1, 17+15+11+5+2+1, 17+15+11+6+1, 17+15+11+6+2+1, 17+15+11+7+1, 17+15+11+7+2+1, 17+15+12+1, 17+15+12+2+1, 17+15+12+3+1, 17+15+12+3+2+1, 17+15+12+4+1, 17+15+12+4+2+1, 17+15+12+5+1, 17+15+12+5+2+1, 17+15+12+6+1, 17+15+12+6+2+1, 17+15+12+7+1, 17+15+12+7+2+1, 17+16+1, 17+16+2+1, 17+16+3+1, 17+16+3+2+1, 17+16+4+1, 17+16+4+2+1, 17+16+5+1, 17+16+5+2+1, 17+16+6+1, 17+16+6+2+1, 17+16+7+1, 17+16+7+2+1, 17+16+8+1, 17+16+8+2+1, 17+16+8+3+1, 17+16+8+3+2+1, 17+16+8+4+1, 17+16+8+4+2+1, 17+16+8+5+1, 17+16+8+5+2+1, 17+16+8+6+1, 17+16+8+6+2+1, 17+16+8+7+1, 17+16+8+7+2+1, 17+16+9+1, 17+16+9+2+1, 17+16+9+3+1, 17+16+9+3+2+1, 17+16+9+4+1, 17+16+9+4+2+1, 17+16+9+5+1, 17+16+9+5+2+1, 17+16+9+6+1, 17+16+9+6+2+1, 17+16+9+7+1, 17+16+9+7+2+1, 17+16+10+1, 17+16+10+2+1, 17+16+10+3+1, 17+16+10+3+2+1, 17+16+10+4+1, 17+16+10+4+2+1, 17+16+10+5+1, 17+16+10+5+2+1, 17+16+10+6+1, 17+16+10+6+2+1, 17+16+10+7+1, 17+16+10+7+2+1, 17+16+11+1, 17+16+11+2+1, 17+16+11+3+1, 17+16+11+3+2+1, 17+16+11+4+1, 17+16+11+4+2+1, 17+16+11+5+1, 17+16+11+5+2+1, 17+16+11+6+1, 17+16+11+6+2+1, 17+16+11+7+1, 17+16+11+7+2+1, 17+16+12+1, 17+16+12+2+1, 17+16+12+3+1, 17+16+12+3+2+1, 17+16+12+4+1, 17+16+12+4+2+1, 17+16+12+5+1, 17+16+12+5+2+1, 17+16+12+6+1, 17+16+12+6+2+1, 17+16+12+7+1, 17+16+12+7+2+1.

In the list above the numbers refer to the embodiments according to their numbering provided hereinabove whereas "+" indicates the dependency from another embodiment. The different individualized embodiments are separated by commas. In other words, "13+11+5+1" for example refers to embodiment 13) depending on embodiment 11), depending on embodiment 5), depending on embodiment 1), i.e. embodiment "13+11+5+1" corresponds to the compounds of formula (I) according to embodiment 1) further limited by all the features of the embodiments 5), 11), and 13).

20) Another embodiment relates to compounds of Formula (I) according to embodiment 1), which are selected from the following compounds:

(2S,3R,4S,5R,6R)-2-(((R)-2-Hydroxy-2-methyl-1-(o-tolyl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-((1-(2-Ethylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-((2-Hydroxy-2-methyl-1-(2-propylphenyl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-((2-Hydroxy-1-(2-isopropylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-((1-(2-Cyclopropylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-1-(2-isobutylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-([1,1'-Biphenyl]-2-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-(trifluoromethyl)phenyl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(3-Fluoro-2-methylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(naphthalen-1-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-((2-Hydroxy-2-methyl-1-(2-methylpyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(3,5,6-trimethylpyrazin-2-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2,5-Dimethylthiazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-((2-Hydroxy-1-(2-(trifluoromethyl)phenyl)butyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3,3-Difluoro-1-hydroxycyclobutyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclopentyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((4-Hydroxy-1-methylpiperidin-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxytetrahydro-2H-pyran-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-2,2,6,6-tetramethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)—((R)-4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3,3-Difluoro-1-hydroxycy-clobutyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(2-isopropylphenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(2-Chlorophenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxytetrahydro-2H-pyran-4-yl)(3-(trifluoromethyl)pyridin-2-yl)methyl)thio)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxytetrahydro-2H-pyran-4-yl)(3,5,6-trimethylpyrazin-2-yl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclopentyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol;

4-(((((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxy-N-methylpiperidine-1-sulfonamide;

(2S,3R,4S,5R,6R)-2-(((R)-(4-Hydroxy-1-(methylsulfonyl)piperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

1-(4-(((((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidin-1-yl)ethan-1-one;

N-cyclopropyl-4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxamide;

Methyl 4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxylate; and (2S,3R,4S,5R,6R)-4-(4-(3,5-Difluoro-4-methylphenyl)-1H-1,2,3-triazol-1-yl)-2-(((R)-2-hydroxy-2-methyl-1-(2-(trifluoromethyl)phenyl)propyl)thio)-6-(hydroxymethyl)tetrahydro-2H-pyran-3,5-diol.

21) Another embodiment relates to compounds of Formula (I) according to embodiment 1), which are selected from the following compounds:

(2S,3R,4S,5R,6R)-2-(((R)-2-Hydroxy-1-phenylethyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2-Bromophenyl)-2-hydroxyethyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-1-(2-isopropylphenyl)ethyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(o-tolyl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2-Ethylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-propylphenyl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-1-(2-isobutylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-pentylphenyl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-([1,1'-Biphenyl]-2-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2-Chlorophenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-(trifluoromethyl)phenyl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2,3-Dichlorophenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(3-Fluoro-2-methylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(naphthalen-1-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-methylpyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(4-methylpyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(3,5,6-trimethylpyrazin-2-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(4-methylisoxazol-3-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(3,5-Dimethylisoxazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2,5-Dimethylthiazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(4-methylthiophen-3-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Ethyl-2-hydroxy-1-(3-methylisoxazol-4-yl)butyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2R)-2-Hydroxy-1-(2-(trifluoromethyl)phenyl)butyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2S)-2-Hydroxy-1-(2-(trifluoromethyl)phenyl)butyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3,3-Difluoro-1-hydroxycyclobutyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(3R,4R,5R,6R)-2-((R)-2-(1-Hydroxycyclobutyl)-2-(o-tolyl)ethyl)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxy-3,3-dimethylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-(1-Hydroxy-3-methylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-((2R,3R)-1-Hydroxy-2,3-dimethylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-((2R,3S)-1-Hydroxy-2,3-dimethylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-((2S,3R)-1-Hydroxy-2,3-dimethylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-((2S,3S)-1-Hydroxy-2,3-dimethylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclopentyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxytetrahydro-2H-pyran-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-2,2,6,6-tetramethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)—(R)-4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)—(S)-4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3,3-Difluoro-1-hydroxycyclobutyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(2-isopropylphenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(2-Chlorophenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxytetrahydro-2H-pyran-4-yl)(3-(trifluoromethyl)pyridin-2-yl)methyl)thio)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxytetrahydro-2H-pyran-4-yl)(3,5,6-trimethylpyrazin-2-yl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclopentyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol;

4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxy-N-methylpiperidine-1-sulfonamide;

(2S,3R,4S,5R,6R)-2-(((R)-(4-Hydroxy-1-(methylsulfonyl)piperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

1-(4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidin-1-yl)ethan-1-one;

N-Cyclopropyl-4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxamide;

Methyl 4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxylate;

(2S,3R,4S,5R,6R)-4-(4-(3,5-Difluoro-4-methylphenyl)-1H-1,2,3-triazol-1-yl)-2-(((R)-2-hydroxy-2-methyl-1-(2-(trifluoromethyl)phenyl)propyl)thio)-6-(hydroxymethyl)tetrahydro-2H-pyran-3,5-diol;

(2S,3R,4S,5R,6R)-2-(((R)-2-Hydroxy-2-methyl-1-(2-(trifluoromethyl)phenyl)propyl)thio)-6-(hydroxymethyl)-4-(4-(naphthalen-2-yl)-1H-1,2,3-triazol-1-yl)tetrahydro-2H-pyran-3,5-diol; and 4-(1-((2S,3R,4S,5R,6R)-3,5-Dihydroxy-2-(((R)-2-hydroxy-2-methyl-1-(2-(trifluoromethyl)phenyl)propyl)thio)-6-(hydroxymethyl)tetrahydro-2H-pyran-4-yl)-1H-1,2,3-triazol-4-yl)-2-fluorobenzonitrile.

22) In addition to the compounds listed in embodiment 20), further compounds according to embodiment 1) are selected from the following compounds:

(2R,3R,4S,5R,6S)-2-(Hydroxymethyl)-6-(((R)-4-hydroxytetrahydro-2H-pyran-4-yl)(o-tolyl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-1-(2-isopropylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2-Cyclopropylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-1-(2-(2-hydroxyethyl)phenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol; and (2S,3R,4S,5R,6R)-2-(((R)-2-Hydroxy-2-methyl-1-(2-(trifluoromethyl)pyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol.

23) In addition to the compounds listed in embodiment 21), further compounds according to embodiment 1) are selected from the following compounds:

(2R,3R,4S,5R,6S)-2-(Hydroxymethyl)-6-(((R)-4-hydroxytetrahydro-2H-pyran-4-yl)(o-tolyl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-1-(2-isopropylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2-Cyclopropylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-1-(2-(2-hydroxyethyl)phenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-(trifluoromethyl)pyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2,5-Dimethyloxazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2R)-2-Hydroxy-2-phenyl-1-(2-(trifluoromethyl)phenyl)ethyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2S)-2-Hydroxy-2-phenyl-1-(2-(trifluoromethyl)phenyl)ethyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2R)-2-Hydroxy-2-(o-tolyl)-1-(2-(trifluoromethyl)phenyl)propyl)thio)-6-(hydroxymethyl)-4-(4-(3,4,5-trifluorophenyl)-1H-1,2,3-triazol-1-yl)tetrahydro-2H-pyran-3,5-diol; and (2S,3R,4S,5R,6R)-2-(((1R,2S)-2-Hydroxy-2-(o-tolyl)-1-(2-(trifluoromethyl)phenyl)propyl)thio)-6-(hydroxymethyl)-4-(4-(3,4,5-trifluorophenyl)-1H-1,2,3-triazol-1-yl)tetrahydro-2H-pyran-3,5-diol.

24) In addition to the compounds listed in embodiment 20) and 22), further compounds according to embodiment 1) are selected from the following compounds:

(2S,3R,4S,5R,6R)-2-(((R)-(5-Cyclopropyl-3-methylisoxazol-4-yl)(1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)—((R)-4-Hydroxy-2,2-dimethyltetrahydro-2H-pyran-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(2-Cyclopropylphenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-methylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(5-Cyclopropyl-4-ethylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(5-Cyclopropyl-4-isobutylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-isopropylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3-Chloropyrazin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3-Cyclopropylpyridin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(4-methylpyridazin-3-yl)methyl)thio)-6-(hydroxymethyl)-4-(4-(3,4,5-trifluorophenyl)-1H-1,2,3-triazol-1-yl)tetrahydro-2H-pyran-3,5-diol;

4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(4-methylisoxazol-3-yl)methyl)-4-hydroxytetrahydro-2H-thiopyran 11-dioxide;

4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(3-methylpyridin-2-yl)methyl)-4-hydroxytetrahydro-2H-thiopyran 1,1-dioxide;

(2R,3R,4S,5R,6S)-2-(Hydroxymethyl)-6-(((R)-(4-hydroxytetrahydro-2H-pyran-4-yl)(3-methylpyridin-2-yl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3-Hydroxy-1-(methylsulfonyl)azetidin-3-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

N-Cyclopropyl-3-((((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-3-hydroxyazetidine-1-carboxamide;

(2R,3R,4S,5R,6S)-6-(((R)-(4,4-Difluoro-1-hydroxycyclohexyl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-(trifluoromethyl)pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(1-Hydroxycyclohexyl)(3-(trifluoromethyl)pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

2R,3R,4S,5R,6S)-6-(((R)-(3-Chloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)—((S)-4-Hydroxy-2,2-dimethyltetrahydro-2H-pyran-4-yl)(2-(trifluoromethyl)phenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

4-Hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(3-methylpyridin-2-yl)methyl)tetrahydro-2H-thiopyran 1,1-dioxide;

(2R,3R,4S,5R,6S)-2-(Hydroxymethyl)-6-(((R)-(4-hydroxytetrahydro-2H-pyran-4-yl)(3-methylpyridin-2-yl)methyl)thio)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)—((S)-4-Hydroxy-2,2-dimethyltetrahydro-2H-pyran-4-yl)(o-tolyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-isopropylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(3-Cyclopropylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(4-methylpyridazin-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-methylpyrazin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(1-Hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(2-Cyclopropylphenyl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(1,4-dimethyl-1H-pyrazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(1-ethyl-4-methyl-1H-1,2,3-triazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(5-ethyl-4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-2-(Hydroxymethyl)-6-(((R)-(4-hydroxytetrahydro-2H-pyran-4-yl)(4-methylisoxazol-3-yl)methyl)thio)-5-methoxy-4-(4-(3,4,5-trifluorophenyl)-1H-1,2,3-triazol-1-yl)tetrahydro-2H-pyran-3-ol;

4-Hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(4-methylisoxazol-3-yl)methyl)tetrahydro-2H-thiopyran 1,1-dioxide;

(2R,3R,4S,5R,6S)-6-(((R)-(5-Cyclopropyl-3-methylisoxazol-4-yl)(1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(5-Cyclopropyl-4-ethylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(5-Cyclopropyl-4-isobutylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(3-Chloropyrazin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4-Chloro-3-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-ethylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(3,4-Dichloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((3,6-Dichloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2S,3R,4S,5R,6R)-2-(((R)—((S)-4-Hydroxy-2,2-dimethyltetrahydro-2H-pyran-4-yl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-6-(((R)-(5-Cyclopropyl-4-methylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((4,4-Difluoro-1-hydroxycyclohexyl)(4-ethyl-5-propylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-methyl-4-(trifluoromethyl)pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

2R,3R,4S,5R,6S)-6-(((R)-(3-Chloro-6-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3,5,6-trimethylpyrazin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

9-((((2S,3R,4S,5R,6R)-5-Hydroxy-6-(hydroxymethyl)-3-methoxy-4-(4-(3,4,5-trifluorophenyl)-1H-1,2,3-triazol-1-yl)tetrahydro-2H-pyran-2-yl)thio)(3-methylpyridin-2-yl)methyl)-3-oxaspiro[5.5]undecan-9-ol;

(2R,3R,4S,5R,6S)-6-(((R)-(4,4-Difluoro-1-hydroxycyclohexyl)(3-methylpyridin-2-yl)methyl)thio)-5-ethoxy-2-(hydroxymethyl)-4-(4-(3,4,5-trifluorophenyl)-1H-1,2,3-triazol-1-yl)tetrahydro-2H-pyran-3-ol;

1-(Cyclopropylsulfonyl)-4-((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidin-4-ol;

1-(4-Hydroxy-4-((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidin-1-yl)ethan-1-one;

(N-Cyclopropyl-4-hydroxy-4-((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidine-1-carboxamide;

(2R,3R,4S,5R,6S)-6-(((R)-(4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol;

(2R,3R,4S,5R,6S)-6-(((4,4-Difluoro-1-hydroxycyclohexyl)(3-methylpyridin-2-yl)methyl)thio)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6S)-4-(4-(4-Chloro-2,3-difluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol;

(2R,3R,4S,5R,6S)-6-(((4,4-Difluoro-1-hydroxycyclohexyl)(3-methylpyridin-2-yl)methyl)thio)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6S)-4-(4-(4-Bromo-3,5-difluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol;

(2R,3R,4S,5R,6S)-4-(4-(3,4-Dichloro-5-fluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol;

(2R,3R,4S,5R,6S)-4-(4-(4-Bromo-3-fluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol;

(2R,3R,4S,5R,6S)-4-(4-(4-Chloro-3,5-difluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol; and (2R,3R,4S,5R,6S)-6-(((R)-(4,4-Difluoro-1-hydroxycyclohexyl)(3-methylpyridin-2-yl)methyl)thio)-4-(4-(3,5-difluoro-4-methylphenyl)-1H-1,2,3-triazol-1-yl)-2-(hydroxymethyl)-5-methoxytetrahydro-2H-pyran-3-ol.

25) In addition to the compounds listed in embodiment 21) and 23), further compounds according to embodiment 1) are selected from the following compounds:

(2S,3R,4S,5R,6R)-2-(((R)-(5-Cyclopropyl-3-methylisoxazol-4-yl)(1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)—(R)-4-Hydroxy-2,2-dimethyltetrahydro-2H-pyran-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)—(S)-4-Hydroxy-2,2-dimethyltetrahydro-2H-pyran-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(2,3-Dichlorophenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(2-Cyclopropylphenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-methylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(5-Cyclopropyl-4-ethylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(5-Cyclopropyl-4-isobutylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-isopropylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3-Chloropyrazin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3-Cyclopropylpyridin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(4-methylpyridazin-3-yl)methyl)thio)-6-(hydroxymethyl)-4-(4-(3,4,5-trifluorophenyl)-1H-1,2,3-triazol-1-yl)tetrahydro-2H-pyran-3,5-diol;

4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(4-methylisoxazol-3-yl)methyl)-4-hydroxytetrahydro-2H-thiopyran 1,1-dioxide;

4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(3-methylpyridin-2-yl)methyl)-4-hydroxytetrahydro-2H-thiopyran 1,1-dioxide;

(2R,3R,4S,5R,6S)-2-(Hydroxymethyl)-6-(((R)-(4-hydroxytetrahydro-2H-pyran-4-yl)(3-methylpyridin-2-yl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3-Hydroxy-1-(methylsulfonyl)azetidin-3-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

Methyl 3-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-3-hydroxyazetidine-1-carboxylate;

N-Cyclopropyl-3-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-3-hydroxyazetidine-1-carboxamide;

(2R,3R,4S,5R,6S)-6-(((R)-(4,4-Difluoro-1-hydroxycyclohexyl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-(trifluoromethyl)pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(1-Hydroxycyclohexyl)(3-(trifluoromethyl)pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

2R,3R,4S,5R,6S)-6-(((R)-(3-Chloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)—(R)-4-Hydroxy-2,2-dimethyltetrahydro-2H-pyran-4-yl)(2-(trifluoromethyl)phenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)—(S)-4-Hydroxy-2,2-dimethyltetrahydro-2H-pyran-4-yl)(2-(trifluoromethyl)phenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

4-Hydroxy-4-((R)-(((2S,3R,4S,5R,6R)-5-hydroxy-6-(hydroxymethyl)-3-methoxy-4-(4-(3,4,5-trifluorophenyl)-

1H-1,2,3-triazol-1-yl)tetrahydro-2H-pyran-2-yl)thio)(3-methylpyridin-2-yl)methyl)tetrahydro-2H-thiopyran 1,1-dioxide;

(2R,3R,4S,5R,6S)-2-(Hydroxymethyl)-6-(((R)-(4-hydroxytetrahydro-2H-pyran-4-yl)(3-methylpyridin-2-yl)methyl)thio)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)—((R)-4-Hydroxy-2,2-dimethyl-tetrahydro-2H-pyran-4-yl)(o-tolyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)—((S)-4-Hydroxy-2,2-dimethyl-tetrahydro-2H-pyran-4-yl)(o-tolyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-isopropylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(3-Cyclopropylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(4-methylpyridazin-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-methylpyrazin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(1-Hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(2-isopropylphenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(2-Cyclopropylphenyl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(1,4-dimethyl-1H-pyrazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(1-ethyl-4-methyl-1H-1,2,3-triazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4-Chloro-1-ethyl-1H-pyrazol-5-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(5-ethyl-4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-2-(Hydroxymethyl)-6-(((R)-(4-hydroxytetrahydro-2H-pyran-4-yl)(4-methylisoxazol-3-yl)methyl)thio)-5-methoxy-4-(4-(3,4,5-trifluorophenyl)-1H-1,2,3-triazol-1-yl)tetrahydro-2H-pyran-3-ol;

4-Hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(4-methylisoxazol-3-yl)methyl)tetrahydro-2H-thiopyran 1,1-dioxide;

(2R,3R,4S,5R,6S)-6-(((R)-(5-Cyclopropyl-3-methylisoxazol-4-yl)(1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(5-Cyclopropyl-4-ethylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(5-Cyclopropyl-4-isobutylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(3-Chloropyrazin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4-Chloro-3-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-ethylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(3,4-Dichloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2S,3R,4S,5R,6R)-2-(((R)-(3,6-Dichloropyridin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)—((R)-4-Hydroxy-2,2-dimethyl-tetrahydro-2H-pyran-4-yl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)—((S)-4-Hydroxy-2,2-dimethyl-tetrahydro-2H-pyran-4-yl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-6-(((R)-(5-Cyclopropyl-4-methylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-((((R)-4,4-Difluoro-1-hydroxycyclohexyl)(4-ethyl-5-propylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-methyl-4-(trifluoromethyl)pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

2R,3R,4S,5R,6S)-6-(((R)-(3-Chloro-6-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3,5,6-trimethylpyrazin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3,6-dimethylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

9-((R)-(((2S,3R,4S,5R,6R)-5-Hydroxy-6-(hydroxymethyl)-3-methoxy-4-(4-(3,4,5-trifluorophenyl)-1H-1,2,3-triazol-1-yl)tetrahydro-2H-pyran-2-yl)thio)(3-methylpyridin-2-yl)methyl)-3-oxaspiro[5.5]undecan-9-ol;

(2R,3R,4S,5R,6S)-6-(((R)-(4,4-Difluoro-1-hydroxycyclohexyl)(3-methylpyridin-2-yl)methyl)thio)-5-ethoxy-2-(hydroxymethyl)-4-(4-(3,4,5-trifluorophenyl)-1H-1,2,3-triazol-1-yl)tetrahydro-2H-pyran-3-ol;

1-(Cyclopropylsulfonyl)-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidin-4-ol;

1-(4-Hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidin-1-yl)ethan-1-one;

N-Cyclopropyl-4-hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidine-1-carboxamide;

(2R,3R,4S,5R,6S)-6-(((R)-(4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol;

(2R,3R,4S,5R,6S)-6-(((R)-(4,4-Difluoro-1-hydroxycyclohexyl)(3-methylpyridin-2-yl)methyl)thio)-2-(hydroxymethyl)-5-methoxy-4-(4-(2,3,4-trifluorophenyl)-1H-1,2,3-triazol-1-yl)tetrahydro-2H-pyran-3-ol;

((2R,3R,4S,5R,6S)-4-(4-(4-Chloro-2,3-difluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;

(2R,3R,4S,5R,6S)-6-(((R)-(4,4-Difluoro-1-hydroxycyclohexyl)(3-methylpyridin-2-yl)methyl)thio)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6S)-4-(4-(4-Bromo-3,5-difluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;

(2R,3R,4S,5R,6S)-4-(4-(3,4-Dichloro-5-fluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;

(2R,3R,4S,5R,6S)-4-(4-(4-Bromo-3-fluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;

(2R,3R,4S,5R,6S)-4-(4-(4-Chloro-3,5-difluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;

(2R,3R,4S,5R,6S)-6-(((R)-(4,4-Difluoro-1-hydroxycyclohexyl)(3-methylpyridin-2-yl)methyl)thio)-4-(4-(3,5-difluoro-4-methylphenyl)-1H-1,2,3-triazol-1-yl)-2-(hydroxymethyl)-5-methoxytetrahydro-2H-pyran-3-ol; and (2R,3R,4S,5R,6S)-6-(((R)-(4,4-Difluoro-1-hydroxycyclohexyl)(3-methylpyridin-2-yl)methyl)thio)-4-(4-(6-fluoro-5-methylpyridin-3-yl)-1H-1,2,3-triazol-1-yl)-2-(hydroxymethyl)-5-methoxytetrahydro-2H-pyran-3-ol.

The compounds of Formula (I) according to embodiments 1) to 25) and their pharmaceutically acceptable salts can be used as medicaments, e.g. in the form of pharmaceutical compositions for enteral (such especially oral e.g. in form of a tablet or a capsule) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention/prophylaxis or treatment of a disease or disorder mentioned herein comprising administering to a subject a pharmaceutically active amount of a compound of Formula (I) according to embodiments 1) to 25). In a sub-embodiment of the invention, the administered amount is comprised between 1 mg and 1000 mg per day.

For avoidance of any doubt, if compounds are described as useful for the prevention/prophylaxis or treatment of certain diseases, such compounds are likewise suitable for use in the preparation of a medicament for the prevention/prophylaxis or treatment of said diseases. Likewise, such compounds are also suitable in a method for the prevention/prophylaxis or treatment of such diseases, comprising administering to a subject (mammal, especially human) in need thereof, an effective amount of such compound.

26) Another embodiment relates to the compounds of formula (I) as defined in any one of embodiments 1) to 25) which are useful for the prevention/prophylaxis or treatment of diseases and disorders that are related to galectin-3 binding to natural ligands.

Such diseases and disorders that are related to Gal-3 binding to natural ligands are especially diseases and disorders in which inhibition of the physiological activity of Gal-3 is useful, such as diseases in which a Gal-3 receptor participates, is involved in the etiology or pathology of the disease, or is otherwise associated with at least one symptom of the disease.

Diseases or disorders that are related to galectin-3 binding to natural ligands may in particular be defined as including:
fibrosis of organs comprising:
all forms of lung/pulmonary fibrosis including all forms of fibrosing interstitial lung diseases, especially idiopathic pulmonary fibrosis (alternatively named cryptogenic fibrosing alveolitis); pulmonary fibrosis secondary to systemic inflammatory disease such as rheumatoid arthritis, scleroderma (systemic sclerosis, SSc), lupus (systemic lupus erythematosus, SLE), polymyositis, or mixed connective tissue disease (MCTD); pulmonary fibrosis secondary to sarcoidosis; iatrogenic pulmonary fibrosis including radiation-induced fibrosis; silicosis-induced pulmonary fibrosis; asbestos-induced pulmonary fibrosis; and pleural fibrosis;

renal/kidney fibrosis, including renal fibrosis caused by/associated with chronic kidney disease (CKD), (acute or chronic) renal failure, tubulointerstitial nephritis, and/or chronic nephropathies such as (primary) glomerulonephritis and glomerulonephritis secondary to systemic inflammatory diseases such as SLE or SSc, diabetes, focal segmental glomerular sclerosis, IgA nephropathy, hypertension, renal allograft, and Alport syndrome;

all forms of liver/hepatic fibrosis (associated or not with portal hypertension) including cirrhosis, alcohol-induced liver fibrosis, nonalcoholic steatohepatitis, biliary duct injury, primary biliary cirrhosis (also known as primary biliary cholangitis), infection- or viral-induced liver fibrosis (e.g. chronic HCV infection), and autoimmune hepatitis;

all forms of heart/cardiac fibrosis, including heart/cardiac fibrosis associated with cardiovascular diseases, heart failure, Fabry disease, CKD; diabetes, hypertension, or hypercholesterolemia;

gut fibrosis, including gut fibrosis secondary to SSc, and radiation-induced gut fibrosis;

skin fibrosis, including SSc and skin scarring;

head and neck fibrosis, including radiation-induced head and neck fibrosis;

eye/corneal fibrosis, including scarring (e.g. sequelae of laser-assisted in situ keratomileusis, or trabeculectomy);

hypertrophic scarring and keloids, including burn-induced or surgical hypertrophic scarring and keloids;

fibrosis sequelae of organ transplant (including corneal transplant);

and other fibrotic diseases including endometriosis, spinal cord fibrosis, myelofibrosis, perivascular and aterial fibrosis; as well as formation of scar tissue, Peyronie's disease, abdominal or bowel adhesions, bladder fibrosis, fibrosis of the nasal passages, and fibrosis mediated by fibroblasts;

(acute or chronic) liver diseases and disorders including acute and chronic viral hepatitis; cirrhosis caused by/associated with arthritis and vasculitis; metabolic liver diseases caused by/associated with arthritis, myocarditis, diabetes, or neurologic symptoms; cholestatic diseases caused by/associated with hyperlipidaemia, inflammatory bowel disease (IBD), or ulcerative colitis; liver tumors; autoimmune hepatitis and cirrhosis caused by/associated with celiac disease, autoimmune haemolytic anaemia, IBD, autoimmune thyroiditis, ulcerative colitis, diabetes, glomerulonephritis, pericarditis, autoimmune thyroiditis, hyperthyroidism, polymyositis, Sjörgen syndrome, panniculitis, alveolitis or alcoholic steatosis; cirrhosis associated with dementia; cirrhosis associated with peripheral neuropathy; cirrhosis caused by/associated with oral or oesophageal cancer; non-alcoholic fatty liver disease (especially non-alcoholic steatohepatitis) caused by/associated with obesity, metabolic syndrome or type 2 diabetes; hepatic blood vessel disorders (including Budd-Chiari syndrome, portal vein thrombosis, sinusoidal obstruction syndrome); acute and chronic liver failure (associated or not with portal hypertension); liver hypofunction;

acute kidney injury and chronic kidney disease (CKD) [especially CKD of stages 1 to 5 as defined by the Kidney Disease Improving Global Outcomes (KDIGO) Guidelines], in particular CKD (notably of these stages) caused by/associated with cardiac diseases (also referred to as cardio-renal syndrome type 1 and type 2), or caused by/associated with hypertension, or caused by/associated with diabetes (also referred to as diabetic kidney disease (DKD), including DKD associated with hypertension), wherein such diabetes especially is type 1 or type 2 diabetes), or caused by/associated with inflammatory diseases and disorders (such as glomerulonephritis and glomerulonephritis secondary to systemic inflammatory diseases such as SLE or SSc, tubulo-interstitial nephritis, vasculitis, sepsis, urinary tract infection), or caused by/associated with polycystic kidney disease, or caused by/associated with obstructive nephropathy (including calculi, benign prostatic hyperplasia, prostate cancer, retroperitoneal pelvic tumor), or caused by/associated with symptoms associated with neuropathic bladder disease); as well as acute and chronic renal failure;

cardiovascular diseases and disorders (including atherosclerosis caused by/associated with hypertension, hypercholesterolemia, diabetes, inflammation, obesity, elderly/age; peripheral arterial disease caused by/associated with hypertension, hypercholesterolemia, diabetes, elderly/age; deep venous thrombosis; pulmonary embolism caused by/associated with obesity or cancer; aortic aneurysm and dissection caused by/associated with elderly/age, hypertension, Marfan syndrome, congenital heart disorders, inflammatory or infectious disorders; cerebrovascular disease caused by/associated with hypertension, atrial fibrillation, hypercholesterolemia, diabetes, elderly/age; coronary heart disease caused by/associated with hypertension, hypercholesterolemia, diabetes, elderly/age, or CKD (especially CKD of stages 1 to 5 as defined by the Kidney Disease Improving Global Outcomes (KDIGO) Guidelines); rheumatic heart disease caused by/associated with bacterial infection; heart and vascular tumors; cardiomyopathy and arrythmias; valvular heart disease (including valvular calcification and degenerative aortic stenosis); inflammatory heart disease caused by/associated with infection, carditis, glomerulonephritis, cancer; heart failure (HF) defined as including especially congestive HF, including in particular systolic HF/HF with reduced ejection fraction (HFrEF), and diastolic HF/HF with preserved ejection fraction (HFpEF);

interstitial lung diseases and disorders (including smoking-related interstitial lung disease; interstitial lung disease associated with/caused by chronic obstructive pulmonary disease; interstitial pneumonia associated with collagen vascular disease (including usual interstitial pneumonia), or pneumonia);

cell proliferative diseases and cancers (including solid tumors, solid tumor metastasis, carcinoma, sarcoma, myeloma (and multiple myeloma), leukemia, lymphoma, mixed types of cancers, vascular fibroma, Kaposi's sarcoma, chronic lymphocytic leukemia (CLL), spinal cord tumors and invasive metastasis of cancer cells);

inflammatory and autoimmune diseases and disorders including chronic and acute inflammatory and autoimmune diseases and disorders (in particular including sepsis, Q-fever, asthma, rheumatoid arthritis, multiple sclerosis, SLE, SSc, polymyositis, plaque psoriasis (including psoriasis caused by/associated with NASH), atopic dermatitis, inflammatory renal/kidney diseases such as nephropathy (including diabetic nephropathy, glomerulonephritis, tubulointerstitial nephritis), inflammatory cardiac/heart diseases, inflammatory lung/lung related diseases; inflammatory liver/liver related diseases; diabetes (type 1 or type 2) and diabetes related diseases such as diabetic vasculopathy, diabetic nephropathy, diabetic retinopathy, diabetic peripheral neuropathy or skin related condition; viral encephalitis; and COVID-19 and sequelae thereof);

gastrointestinal tract diseases and disorders (including irritable bowel syndrome (IBS), inflammatory bowel disease (IBD), gastritis, and abnormal pancreatic secretion);

pancreatic diseases and disorders (including pancreatitis, e.g. associated with cystic fibrosis);

abnormal angiogenesis-associated diseases and disorders (including arterial obstruction);

brain-associated diseases and disorders (including stroke and cerebral haemorrhage);

neuropathic pain and peripheral neuropathy;

ocular diseases and disorders (including dry eye disease (dry eye syndrome), macular degeneration (AMD associated with age, diabetes related disease (diabetic retinopathy), proliferative vitreoretinopathy (PVR), cicatricial pemphigoid, and glaucoma (including glaucoma associated with elevated intraocular pressure, and ocular scarring after glaucoma filtration surgery), and corneal angiogenesis/neovascularization); and transplant rejection comprising rejection of transplanted organs such as kidney, liver, heart, lung, pancreas, cornea, and skin; graft-versus-host diseases brought about by hematopoietic stem cell transplantation; chronic allograft rejection and chronic allograft vasculopathy; and sequelae of such transplant rejection.

27) A further embodiment relates to the compounds of formula (I) for use according to embodiment 26) wherein said compounds are for use in the prevention/prophylaxis or treatment of fibrosis of organs including liver/hepatic fibrosis, renal/kidney fibrosis, lung/pulmonary fibrosis, heart/cardiac fibrosis, eye/corneal fibrosis, and skin fibrosis; as well as gut fibrosis, head and neck fibrosis, hypertrophic scarring and keloids; and fibrosis sequelae of organ transplant.

28) A further embodiment relates to the compounds of formula (I) for use according to embodiment 26) wherein said compounds are for use in the prevention/prophylaxis or treatment of cardiovascular diseases and disorders.

29) A further embodiment relates to the compounds of formula (I) for use according to embodiment 26) wherein said compounds are for use in the prevention/prophylaxis or treatment of acute kidney injury and chronic kidney disease (CKD).

30) A further embodiment relates to the compounds of formula (I) for use according to embodiment 26) wherein said compounds are for use in the prevention/prophylaxis or treatment of (acute or chronic) liver diseases and disorders.

31) A further embodiment relates to the compounds of formula (I) for use according to embodiment 26) wherein said compounds are for use in the prevention/prophylaxis or treatment of interstitial lung diseases and disorders.

32) A further embodiment relates to the compounds of formula (I) for use according to embodiment 26) wherein said compounds are for use in the prevention/prophylaxis or treatment of ocular diseases and disorders.

33) A further embodiment relates to the compounds of formula (I) for use according to embodiment 26) wherein said compounds are for use in the prevention/prophylaxis or treatment of cell proliferative diseases and cancers.

34) A further embodiment relates to the compounds of formula (I) for use according to embodiment 26) wherein said compounds are for use in the prevention/prophylaxis or treatment of chronic or acute inflammatory and autoimmune diseases and disorders.

35) A further embodiment relates to the compounds of formula (I) for use according to embodiment 26) wherein said compounds are for use in the prevention/prophylaxis or treatment of gastrointestinal tract diseases and disorders.

36) A further embodiment relates to the compounds of formula (I) for use according to embodiment 26) wherein said compounds are for use in the prevention/prophylaxis or treatment of pancreatic diseases and disorders.

37) A further embodiment relates to the compounds of formula (I) for use according to embodiment 26) wherein said compounds are for use in the prevention/prophylaxis or treatment of abnormal angiogenesis-associated diseases and disorders.

38) A further embodiment relates to the compounds of formula (I) for use according to embodiment 26) wherein said compounds are for use in the prevention/prophylaxis or treatment of brain-associated diseases and disorders.

39) A further embodiment relates to the compounds of formula (I) for use according to embodiment 26) wherein said compounds are for use in the prevention/prophylaxis or treatment of neuropathic pain and peripheral neuropathy.

40) A further embodiment relates to the compounds of formula (I) for use according to embodiment 26) wherein said compounds are for use in the treatment of transplant rejection.

Preparation of Compounds of Formula (I):

The compounds of Formula (I) can be prepared by well-known literature methods, by the methods given below, by the methods given in the experimental part below or by analogous methods. Optimum reaction conditions may vary with the particular reactants or solvents used, but such conditions can be determined by a person skilled in the art by routine optimisation procedures. In some cases the order of carrying out the following reaction schemes, and/or reaction steps, may be varied to facilitate the reaction or to avoid unwanted reaction products. In the general sequence of reactions outlined below, the generic groups R, $R^{1a}$, $R^{1b}$, $R^2$, $Ar^1$, and $Ar^2$ are as defined for Formula (I). Other abbreviations used herein are explicitly defined, or are as defined in the experimental section. In some instances, the generic groups R, $R^{1a}$, $R^{1b}$, $R^2$, $Ar^1$, and $Ar^2$ might be incompatible with the assembly illustrated in the schemes below and so will require the use of protecting groups (Pg). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, hydrolysis and transition-metal catalysed cross-coupling reactions which are commonly known to those skilled in the art. The compounds obtained may also be converted into salts, especially pharmaceutically acceptable salts, in a manner known per se.

Compounds of the Formula (I) of the present invention can be prepared according to the general sequence of reactions outlined below. Only a few of the synthetic possibilities leading to compounds of Formula (I) are described.

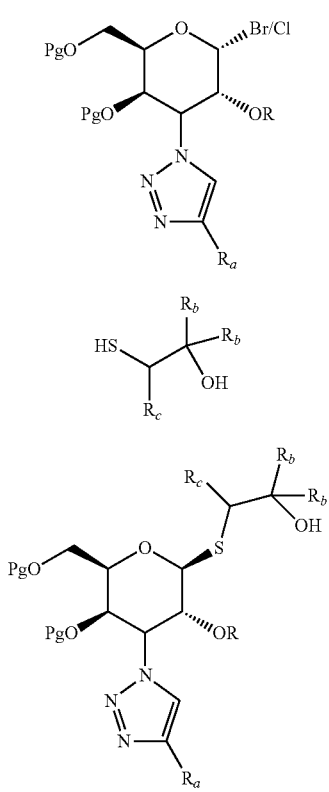

Structure 1

Structure 2

Structure 3

Compounds of Formula (I) are prepared e.g. by reacting a compound of Structure 1 where R is either hydrogen, a suitable protective group (Pg) or $R^1$ (as defined in Formula (I)) with a compound of Structure 2 in a solvent such as EA/water under phase transfer catalytic conditions in presence of tetrabutyl ammonium bromide or tetrabutyl ammonium hydrogensulfate and a base such as $Na_2CO_3$ (*Chem. Comm.* 2006, 2379). Alternatively compound of Structure 1 can react with a compound of Structure 2 under anhydrous conditions in THF or DMF in presence of NaH to give a compound of Structure 3. In Structures 1 and 3, the term Pg represents a protective group such as an acetyl, a chloroacetyl, a benzoyl, or a benzyl group or a 4-chlorobenzyl, which are well known to the person skilled in the art. The hydroxy groups in position 4 and 6 of Structure 1 can be protected with cyclic protective groups such as isopropylidene, benzylidene or bis-tert-butyl silyl groups. R is either hydrogen, a suitable protective group (Pg) or $R^1$ (as defined in Formula (I)). In the case Pg represents an acyl protective group, such a protective group can be cleaved following the reaction of a compound of Structure 1 with a compound of Structure 2 under standard conditions, e.g. by water or an alcohol in the presence or absence of additional solvents such as THF, dioxane, etc. and in the presence of a base such as NaOH, LiOH. In the case wherein such a protective group represents a benzyl group, the protective group can be cleaved e.g. by hydrogen in the presence of a catalyst such as Pd/C, PtO in methanol, ethyl acetate, THF, etc. or mixtures thereof, or by $BBr_3$ in a solvent such DCM. In the case where Pg is a cyclic protective groups such as isopropylidene, benzylidene or bis-tert-butyl silyl groups and R is either hydrogen, a suitable protective group (Pg) or $R^1$ (as defined in Formula (I)), the compounds of Structure 3 can be deprotected under acidic conditions using aqueous acetic acid or TFA.

Structure 4

Structure 5

The compounds of Structure 1 can be prepared e.g. by reacting a compound of Structure 4 with a compound of Structure 5 in the presence of CuI and DIPEA in solvents such as THF or DMF (*Click Chemistry in Glycoscience: New Development and Strategies,* 1st Edition, 2013, John Wiley& Sons), alternatively the reaction can be run on a commercial continuous-flow reactor (Vapourtec) using a copper coil in a solvent such as THF. Compounds of Structure 5 are either commercially available or can be prepared according to procedures known to a person skilled in the art (*Synthesis* 2011, 22, 3604-3611). Compounds of Structure 4 can be prepared in 3 steps from gulo furanose through methods well known to a person skilled in the art (*Carbohydrate Research* 1994, 251, 33-67).

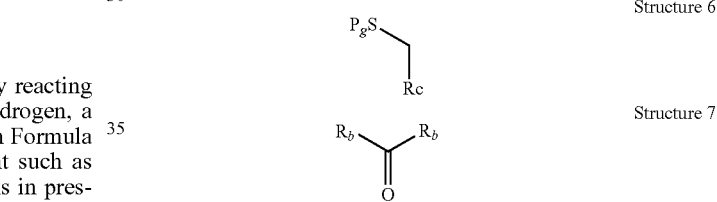

Structure 6

Structure 7

The compounds of Structure 2 can be prepared by reacting a compound of Structure 6 in presence of a strong base such as LDA or BuLi in solvents such as THF, diethylether, toluene, with a compound of Structure 7. (*Eur JOC,* 2002, 1690-1695). In Structure 6, the term Pg represents a suited protective group for the thiol, stable to nucleophiles, such as a quinoline or a tetrahydropyrane. In the case Pg represents a quinoline group, such a protective group can be cleaved following the reaction of a compound of Structure 6 with a compound of Structure 7 under standard conditions, e.g. by mild treatment of sodium cyanoborohydride in acetic acid (*Tet Lett* 1999, 40, 1467-1470). In the case wherein such a protective group represents a tetrahydropyrane group, the protective group can be cleaved following the reaction of a compound of Structure 6 with a compound of Structure 7 e.g. by $AgNO_3$ in a solvent mixture such as THF/water, followed by treatment of the silver salt with NaSH in a solvent mixture such as THF/DCM/water (*Tetrahedron* 59 2003, 3853-3861), alternatively a combination of boron trifluoride, 2-mercaptoethanol in a solvent such as DCM can be used (*Chem Lett* 1996, 999-1000).

Compounds of Structure 6 can be prepared from a halogen methyl aryl/heteroaryl and a thiol protecting group as described in Ref *Eur JOC,* 2002, 1690-1695. Compounds of Structure 7 are commercially available.

Alternatively compounds of Structure 2 can be obtained from reduction of a compound of Structure 8 with LAH in a solvent such as diethyl ether or THF. In Structure 8, the term Pg represents a suited protective group for the thiol, a carbamodithioate, that can also be removed by treatment with LAH.

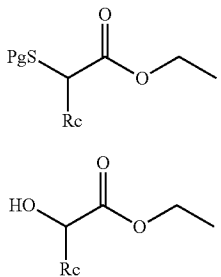

Structure 8

Structure 9

Compounds of Structure 8 are prepared from compounds of Structure 9, through introduction of the dithiocarbamate group carrying the thiol under Mitsunobu conditions in presence of triphenyl phosphine and DEAD in a solvent such as toluene (*Macromolecules* 2008, 41, 6627-6635). Compounds of Structure 9 are either commercially available or they can be prepared from compounds of Structure 10 through an OH insertion reaction in presence of $HClO_4$ in a solvent mixture such as dioxanol water, alternatively the reaction can be run solvent free, employing a silica-supported $HClO_4$ as the catalyst (*Green Chem* 2018, 20, 4547-4556). Compound of Structure 10 can be prepared from commercially available compounds of Structure 11 by diazo transfer reaction with p-ABSA and DBU in a solvent such as acetonitrile (*JOC* 2017, 82, 3000-3010).

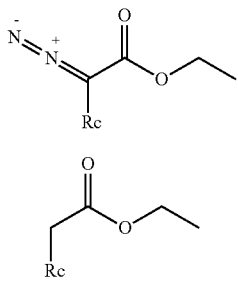

Structure 10

Structure 11

Whenever the compounds of Formula (I) are obtained in the form of mixtures of stereoisomers, the stereoisomers can be sometimes separated by preparative HPLC or more often by HPLC over a chiral stationary phase such as a Daicel ChiralCel OJ-H (5-10 µm) column, or a Daicel ChiralPak IH (5 µm) or AS-H (5 µm) or IB (5 µm) column. Typical conditions of chiral HPLC are an isocratic mixture of eluent A ($CO_2$) and eluent B (DCM/MeOH, 0.1% $Et_2NH$ in EtOH, MeOH, EtOH), at a flow rate of 0.8 to 160 mL/min.

Experimental Part

The following examples illustrate the invention but do not at all limit the scope thereof.

All temperatures are stated in ° C. Commercially available starting materials are used as received without further purification. Unless otherwise indicated, the reactions take place at rt under a nitrogen atmosphere and are run in a flame dried round-bottomed flask equipped with a magnetic stir bar. Compounds are purified by flash chromatography on silica gel (Kieselgel 60, 60 Å, 35-70 µM), by prep TLC (TLC-plates from Merck, Silica gel 60 $F_{254}$) or by preparative HPLC/MS or Flashmaster (Büchi or ISCO). Compounds described in the invention are characterized by $^1$H-NMR (Bruker Avance II, 400 MHz Ultra Shield™ or Brooker Avance III HD, Ascend 500 MHz; chemical shifts are given in ppm relative to the solvent used; multiplicities: s=singlet, d=doublet, t=triplet, q=quadruplet, quint=quintuplet, hex=hexet, hept=heptet, m=multiplet, br=broad, coupling constants are given in Hz) and/or by LCMS (retention time $t_R$ is given in min; molecular weight obtained for the mass spectrum is given in g/mol) or chiral HPLC (retention time $t_R$ is given in min) using the conditions listed below.

Abbreviations (as used herein and in the description above):

ABTS 2,2'-Azino-bis(3-ethylbenzothiazoline-6-sulfonic acid
AcOH acetic acid
$Ac_2O$ acetic anhydride
$AgNO_3$ silver nitrate
$Ag_2O$ silver oxide
aq. aqueous
Bu butyl (such as in nBuLi=n-butyl lithium)
CC column chromatography on silica
conc. concentrated
CSA 10-camphor-sulfonic acid
CuI copper iodide
DBU 1,8-diazabicyclo[5.4.0]undec-7-ene
DCM dichloromethane
DEAD diethyl azodicarboxylate
DIPEA N-ethyl diisopropyl amine
DMAP 4-dimethylamino pyridine
DMF dimethylformamide
DMSO dimethylsulfoxide
EA ethyl acetate
*E. coli. Escherichia coli*
EDC HCl N-(3-dimethylaminopropyl)-N'-ethylcarbodiimide hydrochloride
EtI ethyl iodide
eq (molar) equivalent(s)
Et ethyl
EtOH ethanol
$Et_2O$ diethyl ether
FC flash chromatography
h hour(s)
HATU 1-[Bis(dimethylamino)methylene]-1H-1,2,3-triazolo[4,5-b]pyridinium 3-oxidhexafluorophosphate
$HClO_4$ perchloric acid
Hept heptane
HOBt 1-hydroxybenzotriazole hydrate
HPLC high performance liquid chromatography
$K_2CO_3$ potassium carbonate
$KMnO_4$ potassium permanganate
LAH lithium aluminium hydride
LDA lithium diisopropylamide
LC liquid chromatography
M molarity [mol $L^{-1}$]
Me methyl
MeCN acetonitrile
MeI methyl iodide
MeOH methanol
$MgSO_4$ magnesium sulfate
MS mass spectroscopy
min. minute(s)
N normality
$Na_2CO_3$ sodium carbonate
$NaCNBH_3$ sodium cyanoborohydride NaHCO₃ sodium hydrogen carbonate
NaHMDS sodium bis-trimethylsilyl-amide or sodium hexamethyldisilazide
NaOAc sodium acetate
NaOMe sodium methoxide
NaOtBu sodium tert. (tertiary) butoxide
NaSH sodium hydrogen sulphide
NBS N-bromosuccinimide
NH₄Cl ammonium chloride
OD optical density
o/n over night
org. organic
p-ABSA p-acetamidobenzenesulfonyl azide
Pd/C Palladium on charcoal
Pd(Ph₃)₄ tetrakis(triphenylphosphine)palladium(0)
PPh₃ triphenylphosphine
Ph phenyl
PTSA p-Toluenesulfonic acid
rt room temperature
sat. saturated
SBr₂ thionylbromide
TBAB tetrabutylammonium bromide
TBME tert-butylmethylether
TBTU O-benzotriazol-1-yl-N,N,N',N'-tetramethyluronium tetrafluoroborate
tBu tert-butyl=tertiary butyl
TEA triethylamine
TFA trifluoroacetic acid
THF tetrahydrofuran
TMEDA Tetramethylethylenediamine
TMSCl trimethylsilyl chloride
TMSSMe trimethyl(methylthio)silane
TMSOTf trimethylsilyl trifluoromethanesulfonate
$t_R$ retention time
Ziram zinc dimethyl dithiocarbamate Characterization Methods Used:

Values of inhibitory activity of compounds are determined in the biological assay described below. If not explicitly mentioned otherwise, the inhibition data refer to the binding of biotinylated human Gal-3 (hGal-3).

The LC-MS retention times are obtained using the following elution conditions:

A) LC-MS (A):

Zorbax RRHD SB-Aq, 1.8 µm, 2.1×50 mm column thermostated at 40° C. The two elution solvents are as follows: solvent A=water+0.04% TFA; solvent B=acetonitrile. The eluent flow rate is 4.5 mL/min and the characteristics of the eluting mixture proportion in function of the time t from start of the elution are summarized in the table below (a linear gradient being used between two consecutive time points):

|  | t (min) | | | | |
| --- | --- | --- | --- | --- | --- |
|  | 0 | 0.01 | 1.20 | 1.90 | 2.10 |
| Solvent A (%) | 95 | 95 | 5 | 5 | 95 |
| Solvent B (%) | 5 | 5 | 95 | 95 | 5 |

Detection: UV at 210 nm.

B) LC-MS (B):

Zorbax RRHD SB-Aq, 1.8 µm, 3.0×50 mm column thermostated at 40° C. The two elution solvents are as follows: solvent A=water+0.04% TFA; solvent B=acetonitrile. The eluent flow rate is 1.6 mL/min and the characteristics of the eluting mixture proportion in function of the time t from start of the elution are summarized in the table below (a linear gradient being used between two consecutive time points):

|  | t (min) | | | | |
| --- | --- | --- | --- | --- | --- |
|  | 0 | 0.01 | 1.20 | 1.90 | 2.00 |
| Solvent A (%) | 95 | 95 | 5 | 5 | 95 |
| Solvent B (%) | 5 | 5 | 95 | 95 | 5 |

Detection: UV at 210 nm.

C) LC-MS (C):

Waters BEH C18, 2.5 µm, 2.1×50 mm column thermostated at 40° C. The two elution solvents are as follows: solvent A=water+0.04% TFA; solvent B=acetonitrile. The eluent flow rate is 0.8 mL/min and the characteristics of the eluting mixture proportion in function of the time t from start of the elution are summarized in the table below (a linear gradient being used between two consecutive time points):

|  | t (min) | | | | |
| --- | --- | --- | --- | --- | --- |
|  | 0 | 1.2 | 1.9 | 2.1 | 0 |
| Solvent A (%) | 95 | 5 | 5 | 95 | 95 |
| Solvent B (%) | 5 | 5 | 95 | 95 | 5 |

Detection: UV at 210 nm.

D) Chiral Analytical HPLC (D):

ChiralPak IC, 5 µm, 4.6×250 mm, column thermostated at 40° C. The two elution solvents are as follows: solvent A=$CO_2$; solvent B=DCM/MeOH (1/1). The eluent flow rate is 4.0 mL/min over 5 min. Elution: Isocratic 20% of the solvent B and 80% of the solvent A. Detection: 230 nm.

E) Chiral Analytical HPLC (E):

ChiralPak IH, 5 µm, 4.6×250 mm, column thermostated at 40° C. The two elution solvents are as follows: solvent A=$CO_2$; solvent B=DCM/MeOH (1/1). The eluent flow rate is 4.0 mL/min over 5 min. Elution: Isocratic 15% of the solvent B and 85% of the solvent A. Detection: 254 nm.

F) Chiral Analytical HPLC (F):

ChiralPak 1H, 5 µm, 4.6×250 mm, column thermostated at 40° C. The two elution solvents are as follows: solvent A=$CO_2$; solvent B=EtOH. The eluent flow rate is 4.0 mL/min over 5 min. Elution: Isocratic 25% of solvent B and 75% of solvent A. Detection: 210 nm.

G) Chiral Analytical HPLC (G):

Chiralcel OJ-H, 5 µm, 4.6×250 mm, column thermostated at 40° C. The two elution solvents are as follows: solvent A=$CO_2$; solvent B=MeCN/EtOH (1/1). The eluent flow rate is 4.0 mL/min over 3 min. Elution: Isocratic 10% of solvent B and 90% of solvent A. Detection: 210 nm.

H) Chiral Analytical HPLC (H):

ChiralPak 1H, 5 µm, 4.6×250 mm, column thermostated at 40° C. The two elution solvents are as follows: solvent A=$CO_2$; solvent B=DCM/MeOH/DEA (50/50/0.1). The eluent flow rate is 4.0 mL/min over 5 min. Elution: Isocratic 15% of solvent B and 85% of solvent A. Detection: 210 nm.

I) Chiral Analytical HPLC (I):

Epimers of an epimer mixture are characterized by chiral analytical HPLC. Conditions vary for each epimer mixture. Several columns are used, all have the same size: 4.6×250 mm, 50 µm. Elution is done at isocratic conditions: Eluent A is always $CO_2$, eluent B is either an organic solvent or a mixture thereof. Runs last from 2.5 to 5 min.

Column type, B solvent and the length of the elution is mentioned for each epimer mixture in the corresponding Tables shown herewith.

J) Chiral Analytical HPLC (J):

ChiralPak IB, 5 μm, 4.6×250 mm, column thermostated at 40° C. The two elution solvents are as follows: solvent A=$CO_2$; solvent B=EtOH. The eluent flow rate is 4.0 mL/min over 5 min. Elution: Isocratic 35% of solvent B and 65% of solvent A. Detection: 246 nm.

K) Chiral Analytical HPLC (K):

ChiralPak IB, 5 μm, 4.6×250 mm, column thermostated at 40° C. The two elution solvents are as follows: solvent A=$CO_2$; solvent B=EtOH. The eluent flow rate is 4.0 mL/min over 5 min. Elution: Isocratic 30% of solvent B and 70% of solvent A. Detection: 210 nm.

L) Chiral Analytical HPLC (L):

ChiralPak IB, 5 μm, 4.6×250 mm, column thermostated at 40° C. The two elution solvents are as follows: solvent A=$CO_2$; solvent B=MeOH, 01% DEA. The eluent flow rate is 4.0 mL/min over 5 min. Elution: Isocratic 25% of solvent B and 75% of solvent A. Detection: 210 nm.

M) Chiral Analytical HPLC (M):

ChiralPak IB, 5 μm, 4.6×250 mm, column thermostated at 40° C. The two elution solvents are as follows: solvent A=$CO_2$; solvent B=MeOH, 01% DEA. The eluent flow rate is 4.0 mL/min over 5 min. Elution: Isocratic 30% of solvent B and 70% of solvent A. Detection: 210 nm.

N) Chiral Analytical HPLC (N):

Chiralcel OZ-H, 5 μm, 4.6×250 mm, column thermostated at 40° C. The two elution solvents are as follows: solvent A=$CO_2$; solvent B=MECN/MEOH, 1:1. The eluent flow rate is 4.0 mL/min over 5 min. Elution: Isocratic 30% of solvent B and 70% of solvent A. Detection: 247 nm.

O) Chiral Analytical HPLC (O):

Chiralcel OZ-H, 5 μm, 4.6×250 mm, column thermostated at 40° C. The two elution solvents are as follows: solvent A=$CO_2$; solvent B=MECN/MEOH, 1:1. The eluent flow rate is 4.0 mL/min over 5 min. Elution: Isocratic 40% of solvent B and 60% of solvent A. Detection: 210 nm.

Non-Chiral Preparative Methods Used:

The purifications by preparative LC-MS are performed using the conditions described hereafter.

P) Preparative LC-MS (I):

A Waters column (Waters XBridge C18, 10 μm OBD, 30×75 mm) is used. The two elution solvents are as follows: solvent A=water+0.5% of a solution of 25% $NH_4OH$ in water; solvent B=acetonitrile. The eluent flow rate is 75 mL/min and the characteristics of the eluting mixture proportion in function of the time t from start of the elution are summarized in the tables below (a linear gradient being used between two consecutive time points):

|  | t (min) | | | | | |
| --- | --- | --- | --- | --- | --- | --- |
|  | 0 | 0.01 | 4.0 | 6.0 | 6.2 | 6.6 |
| Solvent A (%) | 90 | 90 | 5 | 5 | 90 | 90 |
| Solvent B (%) | 10 | 10 | 95 | 95 | 10 | 10 |

Detection 210 nm.

Q) Preparative LC-MS (II):

A Waters column (Waters XBridge C18, 10 μm OBD, 30×75 mm) is used. The two elution solvents are as follows: solvent A=water+HCOOH 0.5%; solvent B=acetonitrile. The eluent flow rate is 75 mL/min and the characteristics of the eluting mixture proportion in function of the time t from start of the elution are summarized in the tables below (a linear gradient being used between two consecutive time points):

|  | t (min) | | | | | |
| --- | --- | --- | --- | --- | --- | --- |
|  | 0 | 0.01 | 4.0 | 6.0 | 6.2 | 6.6 |
| Solvent A (%) | 90 | 90 | 5 | 5 | 90 | 90 |
| Solvent B (%) | 10 | 10 | 95 | 95 | 10 | 10 |

Detection

Chiral Preparative HPLC Methods Used:

The separation of selected enantiomeric building blocks is performed by preparative chiral column chromatography using the conditions described hereafter.

R) Chiral Preparative HPLC (I):

ChiralPack IC, 5 μm, 30×250 mm is used. The two elution solvents are as follows: solvent A=$CO_2$; solvent B=DCM/MeOH (1/1). The eluent flow rate was 160 mL/min. The elution is done using 80% of the solvent A and 20% of the solvent B. The injection V=3 mL, 20 mg/mL DCM/MeOH (1/1).

S) Chiral Preparative HPLC (II):

ChiralPack IH, 5 μm, 30×250 mm is used. The two elution solvents are as follows: solvent A=$CO_2$; solvent B=DCM/MeOH (1/1). The eluent flow rate was 160 mL/min. The elution is done using 75% of the solvent A and 25% of the solvent B. The injection V=2 mL, 10 mg/mL DCM/MeOH (1/1).

T) Chiral Preparative HPLC (III):

ChiralPack IB, 5 μm, 30×250 mm is used. The two elution solvents are as follows: solvent A=$CO_2$; solvent B=EtOH. The eluent flow rate was 160 mL/min. The elution is done using 60% of the solvent A and 40% of the solvent B. The injection V=1.0 mL, 21.1 mg/mL EtOH.

V) Chiral Preparative HPLC (IV):

ChiralPack IB, 5 μm, 30×250 mm is used. The two elution solvents are as follows: solvent A=$CO_2$; solvent B=EtOH. The eluent flow rate was 160 mL/min. The elution is done using 70% of the solvent A and 30% of the solvent B. The injection V=2.0 mL, 10 mg/mL EtOH.

W) Chiral Preparative HPLC (V):

ChiralPack IB, 5 μm, 30×250 mm is used. The two elution solvents are as follows: solvent A=$CO_2$; solvent B=MeOH, 0.1% DEA. The eluent flow rate was 160 mL/min. The elution is done using 75% of the solvent A and 25% of the solvent B. The injection V=1.0 mL, 10 mg/mL MeOH.

X) Chiral Preparative HPLC (VI):

ChiralPack IB, 5 μm, 30×250 mm is used. The two elution solvents are as follows: solvent A=$CO_2$; solvent B=MeOH, 0.1% DEA. The eluent flow rate was 160 mL/min. The elution is done using 70% of the solvent A and 30% of the solvent B. The injection V=1.0 mL, 7 mg/mL MeOH.

Y) Chiral Preparative HPLC (VII): ELN012-4912

Chiralcel OZ-H, 5 μm, 30×250 mm is used. The two elution solvents are as follows: solvent A=$CO_2$; solvent B=MECN/EtOH, 1:1. The eluent flow rate was 160 mL/min. The elution is done using 70% of the solvent A and 30% of the solvent B.

Z) Chiral Preparative HPLC (VIII): ELN370-0120

Chiralcel OZ-H, 5 μm, 30×250 mm is used. The two elution solvents are as follows: solvent A=$CO_2$; solvent B=MECN/EtOH, 1:1. The eluent flow rate was 160 mL/min. The elution is done using 60% of the solvent A and 40% of the solvent B.

PREPARATION OF THE INTERMEDIATES

Following Intermediates are prepared for the synthesis of the compounds.

Intermediate 1

(3R,4S,5R,6R)-6-(Acetoxymethyl)-4-azidotetrahydro-2H-pyran-2,3,5-triyl triacetate (3R,4S,5R,6R)-6-(Acetoxymethyl)-4-azidotetrahydro-2H-pyran-2,3,5-triyl triacetate is synthesized from (3aR,5S,6S,6aR)-5-((R)-2,2-dimethyl-1,3-dioxolan-4-yl)-2,2-dimethyltetrahydrofuro[2,3-d][1,3]dioxol-6-ol following the literature procedures from Ref: *Carbohydrate Research* 1994, 251, 33-67 and references cited therein.

Intermediate 2

(2R,3R,4S,5R,6R)-2-(Acetoxymethyl)-4-azido-6-bromotetrahydro-2H-pyran-3,5-diyl diacetate (3R,4S,5R,6R)-6-(Acetoxymethyl)-4-azidotetrahydro-2H-pyran-2,3,5-triyl triacetate To a solution of Intermediate 1 (8.0 g, 21.4 mmol) in DCM (250.0 mL) and EA (25.0 mL) is added titanium(IV) bromide (2.4 g, 64.3 mmol, 3.0 eq). The reaction mixture is stirred at rt for 48 h, quenched with NaOAc (25.0 g, 30.4 mmol, 1.4 eq) and stirred at rt for 1 h. The mixture is partitioned between $H_2O$ and DCM, the layers are separated and the aq. layer is extracted with DCM (3×). The combined organic layer is dried over $Na_2SO_4$, filtered and solvent removed in vacuo to give a pale yellow oil. The crude material is purified by Flash Master (Büchi, 120 g column, product added dry on isolute, Hept/EA 100/0 to 8/2, Rf(Hept/EA 8/2)=0.57, not UV-active, stained with $KMnO_4$) to yield the title compound as a colorless oil (11.4 g, 92%). LC-MS (A) $t_R$=0.91 min; [M+H]$^+$: 394.00. $^1$H NMR (400 MHz, CDCl$_3$) δ: 6.73 (d, J=3.7 Hz, 1H), 5.52 (d, J=2.9 Hz, 1H), 4.97 (dd, J$_1$=3.7 Hz, J$_2$=10.5 Hz, 1H), 4.44 (t, J=6.4 Hz, 1H), 4.21 (dd, J$_1$=6.0 Hz, J$_2$=11.5 Hz, 1H), 4.18 (dd, J$_1$=3.3 Hz, J$_2$=10.5 Hz, 1H), 4.07 (dd, J$_1$=7.0 Hz, J$_2$=11.5 Hz, 1H), 2.20 (s, 3H), 2.19 (s, 3H), 2.10 (s, 3H).

Intermediate 3

(2R,3R,4S,5R,6R)-2-(acetoxymethyl)-6-bromo-4-(4-(3,4,5-trifluorophenyl)-1H-1,2,3-triazol-1-yl)tetrahydro-2H-pyran-3,5-diyl diacetate To a solution of Intermediate 2 (11.1 g, 28.3 mmol) in THF (306.0 mL) are added 3,4,5-trifluorophenylacetylene (4.55 g, 28.3 mmol, 1.0 eq), CuI (1.6 g, 8.48 mmol, 0.3 eq) and DIPEA (14.5 mL, 84.8 mmol, 3.0 eq). The reaction mixture is stirred at 44° C. for 17 h. The mixture is cooled to rt, diluted with EA and filtered. The org. layer is washed with aq. sat. NH$_4$Cl (2×20 mL), brine, dried over Na$_2$SO$_4$, filtered and solvent concentrated under reduced pressure to afford a beige solid. The crude material is purified by Flash Master (ISCO, product added on isolute on the column, 220 g column, Hept/EA 85/15 to 50/50, EA in Hept, Rf(Hept/EA 1/1)=0.52, UV-active and stained with KMnO$_4$) to recover Intermediate 3 as a white powder (11.1 g, 72%). LC-MS (A) $t_R$=1.04 min; [M+H]$^+$: 552. $^1$H NMR (400 MHz, CDCl$_3$) δ: 7.82 (s, 1H), 7.46 (dd, J$_1$=6.5 Hz, J$_2$=8.1 Hz, 2H), 6.91 (d, J=3.8 Hz, 1H), 5.84 (dd, J$_1$=3.8 Hz, J$_2$=11.3 Hz, 1H), 5.64 (d, J=1.7 Hz), 5.34 (dd, J$_1$=3.0 Hz, J$_2$=11.4 Hz, 1H), 4.66 (t, J=6.4 Hz, 1H), 4.26 (dd, J$_1$=6.3 Hz, J$_2$=11.5 Hz, 1H), 4.16 (dd, J$_1$=6.5 Hz, J$_2$=11.5 Hz, 1H), 2.09 (s, 6H), 1.98 (s, 3H).

Intermediate 4

(2R,3R,4S,5R,6R)-2-(Acetoxymethyl)-6-bromo-4-(4-(3-fluorophenyl)-1H-1,2,3-triazol-1-yl)tetrahydro-2H-pyran-3,5-diyl diacetate Intermediate 4 (0.51 g) is synthesized from Intermediate 2 and 3-trifluorophenylacetylene following the procedure described for Intermediate 3. LC-MS (A) $t_R$=1.03 min; [M+H]$^+$: 513.82. $^1$H NMR (400 MHz, CDCl$_3$) δ: 7.83 (s, 1H), 7.55-7.60 (m, 2H), 7.42 (dd, J$_1$=7.7 Hz, J$_2$=14.0 Hz, 1H), 7.07 (td, J$_1$=1.8 Hz, J$_2$=8.5 Hz), 6.91 (d, J=3.7 Hz, 1H), 5.84 (dd, J$_1$=3.7 Hz, J$_2$=11.3 Hz, 1H), 5.66 (d, J=1.4 Hz, 1H), 5.36 (dd, J$_1$=2.8 Hz, J$_2$=11.3 Hz, 1H), 4.67 (t, J=6.5 Hz, 1H), 4.26 (dd, J$_1$=6.3 Hz, J$_2$=11.3 Hz, 1H), 4.16 (dd, J$_1$=6.8 Hz, J$_2$=11.8 Hz, 1H), 2.09 (s, 6H), 1.98 (s, 3H).

Intermediate 5

Intermediate 5 is prepared by using adapted procedures from Ref: *Eur JOC,* 2002, 1690-1695 and references cited therein.

1-Mercapto-2-methyl-1-(o-tolyl)propan-2-ol 1. 2-((2-Methylbenzyl)thio)quinoline

DBU (0.27 mL, 1.77 mmol, 1.0 eq) is added to a solution of 2-quinolinethiol (0.30 g, 1.77 mmol) in toluene (6.0 mL) at rt. The reaction mixture is stirred at rt for 30 min, 2-methylbenzyl bromide (0.25 mL, 1.77 mmol, 1.0 eq) is added and stirring is continued for 3 h. The reaction mixture is concentrated under reduced pressure to give a yellow solid, that is triturated from Hept. The mother liquor is concentrated in vacuo to yield the title compound (0.400 g, 85%). LC-MS (A) $t_R$=1.11 min; [M+H]$^+$: 266.03

2. 2-Methyl-1-(quinolin-2-ylthio)-1-(o-tolyl)propan-2-ol

To a cooled (−78° C.) solution of 2-((2-methylbenzyl)thio)quinoline (0.20 g, 0.75 mmol) in THF (8.0 mL) is added n-BuLi (1.6M in hexane, 0.71 mL, 1.13 mmol, 1.5 eq) and the reaction mixture is stirred at −78° C. for 1 h. Acetone (0.07 mL, 0.90 mmol, 1.2 eq) in THF (4.0 mL) is added and the reaction mixture is allowed to warm to −50° C. and stirred at this temperature for 4 h. The reaction mixture is quenched by the addition of aq. sat. NH$_4$Cl and extracted with EA, the layers are separated, the aqueous layer is extracted with EA (3×). The combined organic layer is washed with brine, dried over MgSO$_4$, filtered and solvent removed in vacuo to give a yellow oil. The crude material is purified by Flash Master (Büchi, 5 g column, product added dry on isolute, 10 mL/min, 5 mL fractions Hept/EA 100/0 to 8/2, Rf(Hept/EA 8/2)=0.15) to give 2-methyl-1-phenyl-1-(quinolin-2-ylthio)propan-2-ol as a colourless oil (0.14 g, 57%). LC-MS (A) $t_R$=1.05 min; [M+H]$^+$: 324.06.

3. 1-Mercapto-2-methyl-1-(o-tolyl)propan-2-ol (Intermediate 5)

2-Methyl-1-(quinolin-2-ylthio)-1-(o-tolyl)propan-2-ol (0.13 g, 0.42 mmol) is dissolved in AcOH (9.0 mL) and NaCNBH₃ (0.14 g, 2.1 mmol, 5.0 eq) is added. The reaction mixture is stirred at rt for 17 h, quenched with water (6.0 mL), stirred at rt for 1 h, then diluted with DCM. The layers are separated, the aqueous layer is extracted with DCM, the combined organic layer is washed with brine, dried over MgSO₄ and solvent is removed in vacuo to give the title compound as a yellow oil (0.18 g), that is used without further purification. LC-MS (A) $t_R$=0.85 min; [M+H]⁺: no mass.

Intermediate 6R (R)-1-Mercapto-2-methyl-1-(2-(trifluoromethyl)pyridin-3-yl)propan-2-ol 1. 2-Methyl-1-(quinolin-2-ylthio)-1-(2-(trifluoromethyl)pyridin-3-yl)propan-2-ol The title compound is prepared from 3-(bromomethyl)-2-(trifluoromethyl)pyridine and 2-quinoline thiol according to the procedure described for Intermediate 5 (Step 1. and Step 2.) as an orange oil (3.8 g). LC-MS (A): $t_R$=1.02 min; [M+H]⁺: 379.34.

2. (R)-2-Methyl-1-(quinolin-2-ylthio)-1-(2-(trifluoromethyl)pyridin-3-yl)propan-2-ol Separation of the epimers of 2-methyl-1-(quinolin-2-ylthio)-1-(2-(trifluoromethyl)pyridin-3-yl)propan-2-ol (3.8 g) by chiral preparative HPLC (I) yielded the title compound (1.87 g) as a yellow oil. Chiral analytical HPLC (D): $t_R$=1.45 min.

(R)-1-mercapto-2-methyl-1-(2-(trifluoromethyl)pyridin-3-yl)propan-2-ol (Intermediate 6R)

The title compound is prepared from (R)-2-methyl-1-(quinolin-2-ylthio)-1-(2-(trifluoromethyl)pyridin-3-yl)propan-2-ol according to the procedures described for Intermediate 5 (Step. 3) to yield a white solid (0.17, 88%). LC-MS (A): $t_R$=0.79 min; [M+H]⁺: 252.14. ¹H NMR (400 MHz, DMSO) δ: 8.59 (dd, $J_1$=1.3 Hz, $J_2$=4.5 Hz, 1H), 8.50 (d, J=8.0 Hz, 1H), 7.70 (dd, $J_1$=4.5 Hz, $J_2$=8.2 Hz, 1H), 4.13 (s, 1H), 3.13 (s, 1H), 1.40 (s, 3H), 0.97 (s, 3H).

Intermediate 6S (S)-1-Mercapto-2-methyl-1-(2-(trifluoromethyl)pyridin-3-yl)propan-2-ol The title compound, the S-epimer, is prepared from 3-(bromomethyl)-2-(trifluoromethyl)pyridine and 2-quinoline thiol according to the procedure described for Intermediate 6R (S-epimer is obtained at Step 2. through chiral separation by chiral preparative HPLC (I)) to yield a white solid (0.17 g). LC-MS (A): $t_R$=0.79 min; [M+H]⁺: 252.15.

Intermediate 7

4-(Mercapto(3,5,6-trimethylpyrazin-2-yl)methyl)-1-methylpiperidin-4-ol

1. S-(Tetrahydro-2H-pyran-2-yl) ethanethioate 3,4-Dihydro-2H-pyran (3.2 mL, 34.6 mmol, 1.0 eq) is added slowly to a cooled (0° C.) mixture of thioacetic acid (2.7 g, 34.6 mmol) in HCl (37%, 5.0 mL). After 2 h at rt, the reaction mixture is diluted with Et₂O, the organic layer is washed with aq. 10% NaHCO₃, dried over MgSO₄, filtered and solvent removed in vacuo to give a beige oil (6.1 g, >99%), that is used without further purification. ¹H NMR (400 MHz, CDCl₃) δ: 1.60-1.82 (m, 5H+H₂O), 1.96-2.07 (m, 1H), 2.38 (s, 3H), 3.70-3.76 (m, 1H), 3.86-3.93 (m, 1H), 5.58-5.80 (dd, J=4.3, 3.8 Hz, 1H).

2. 2,3,5-Trimethyl-6-(((tetrahydro-2H-pyran-2-yl)thio)methyl)pyrazine

S-(Tetrahydro-2H-pyran-2-yl) ethanethioate (3.0 g, 18.7 mmol) is added to the cooled (0° C.) stirred mixture of KOH (2.3 g, 37.4 mmol, 2.0 eq) in DMSO (28.0 mL) and water (10.0 mL). The reaction mixture is stirred at 0° C. for 15 min, followed by 30 min at rt, finally 2-(bromomethyl)-3,5,6-trimethylpyrazine (4.15 g, 18.7 mmol, 1.0 eq) is added portionwise at 0° C. The reaction mixture is allowed to warm to rt for 17 h, quenched with water and Et₂O, the layers are separated and the aqueous layer is extracted with Et₂O (3×). The combined organic layer is washed with water and brine, dried over MgSO₄, filtered and solvent removed in vacuo to give a beige oil. The crude material is purified by Flash Master (ISCO, 80 g column, product added on isolute, Hept/EA 100/0 to 1/1, Rf(Hept/EA 1/1)=0.27) to give 2,3,5-trimethyl-6-(((tetrahydro-2H-pyran-2-yl)thio)methyl)pyrazine as a colourless oil (2.9 g, 61%). LC-MS (A): $t_R$=0.76 min; [M+H]⁺: 253.26.

3. 1-Methyl-4-(((tetrahydro-2H-pyran-2-yl)thio)(3,5,6-trimethylpyrazin-2-yl)methyl)piperidin-4-ol To a cooled (−78°) solution of 2,3,5-trimethyl-6-(((tetrahydro-2H-pyran-2-yl)thio)methyl)pyrazine (2.4 g, 9.51 mmol) in THF (25.0 mL) is added n-BuLi (1.6 M in hexane, 8.9 mL, 14.3 mmol, 1.5 eq). The reaction mixture is stirred at −78° C. for 1 h, then a solution of N-methyl-4-piperidone (1.62 mL, 11.4 mmol, 1.2 eq) in THF (25.0 mL) is added at −78° C. and stirring continued at −78° C. for 1 h. The reaction mixture is quenched with aq. sat. NH₄Cl, extracted with EA, the layers are separated and the aqueous layer is extracted with EA (3×). The combined organic layer is washed with brine, dried over MgSO₄, filtered and solvent removed in vacuo to give a yellow oil. The crude material is purified by preparative HPLC/MS (I) to afford the title product as a pale yellow oil (2.2 g, 63%). LC-MS (A): $t_R$=0.58 min; [M+H]⁺: 366.26.

4. 4-(Mercapto(3,5,6-trimethylpyrazin-2-yl)methyl)-1-methylpiperidin-4-ol (Intermediate 7)

To a solution of 1-methyl-4-(((tetrahydro-2H-pyran-2-yl)thio)(3,5,6-trimethylpyrazin-2-yl)methyl)piperidin-4-ol (1.0 g, 2.74 mmol) in THF (5.0 mL) is added AgNO₃ (0.95 g, 5.56 mmol, 2.03 eq), followed by water (5.0 mL) and stirred for 20 min at rt. The reaction mixture is diluted with DCM (100.0 mL), NaSH (1.53 g, 27.4 mmol, 10.0 eq) is added and the mixture stirred vigorously for 30 min at rt. The resulting black precipitate is removed by filtration and washed with DCM (2×). The filtrate is collected and its layers separated, the organic layer is washed with aq. sat. NH₄Cl, dried over MgSO₄, filtered and solvent removed in vacuo to give a pale yellow oil (0.98 g). The crude material is purified by Flash Master (ISCO, 12 g gold column, DCM/MeOH 100/0 to 8/2, Rf(DCM/MeOH 9/1)=0.14) to give Intermediate 7 as a pale yellow oil (0.56 g, 73%). LC-MS (A): $t_R$=0.51 min; [M+H]⁺: 282.27.

Intermediate 8

(2R,3R,4S,5R,6S)-2-(Acetoxymethyl)-6-(((4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate

1. 1,1,1-Trichloro-2-methylpropan-2-yl 4-oxopiperidine-1-carboxylate

Piperidin-4-one HCl (0.50 g, 3.5 mmol) is dissolved in DCM (25.0 mL), 2,2,2-trichloro-1,1-dimethylethyl chloroformate (0.87 g, 3.5 mmol, 1.0 eq) followed by DIPEA (1.8 mL, 10.5 mmol, 3.0 eq) are added and the reaction mixture is stirred at rt for 17 h. DIPEA is added again (1.0 mL, 5.8 mmol) and the reaction mixture stirred for further 5 h, then partitioned between DCM and water. The layers are separated and the aqueous layer is extracted with DCM (3×). The combined organic layer is dried over MgSO$_4$, filtered and the solvent removed in vacuo to give an orange oil that is purified by preparatory HPLC/MS (I) to recover 1,1,1-trichloro-2-methylpropan-2-yl 4-oxopiperidine-1-carboxylate as a white powder (0.434 g, 41%). LC-MS (A): $t_R$=0.91 min; [M+H]$^+$: 301.87.

2. 1,1,1-Trichloro 4-hydroxy-4-(mercapto(phenyl)methyl)piperidine-1-carboxylate 1,1,1-Trichloro 4-hydroxy-4-(mercapto(phenyl)methyl)piperidine-1-carboxylate is prepared from 1-(bromomethyl)-2-(trifluoromethyl)benzene and 1,1,1-trichloro-2-methylpropan-2-yl 4-oxopiperidine-1-carboxylate according to the procedures described for the synthesis of Intermediate 5. LC-MS(A): $t_R$=1.14 min, [M+1$^+$=493.83.

3. (2R,3R,4S,5R,6S)-2-(Acetoxymethyl)-6-(((4-hydroxy-1-(((1,1,1-trichloro-2-methylpropan-2-yl)oxy)carbonyl)piperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate To a solution of Intermediate 3 (0.28 g, 0.509 mmol) in EA (8.0 mL) are added TBAB (0.041 g, 0.13 mmol, 0.25 eq), aq. 1M Na$_2$CO$_3$ (12.0 mL) and 1,1,1-trichloro 4-hydroxy-4-(mercapto(phenyl)methyl)piperidine-1-carboxylate (0.25 g, 0.51 mmol, 1.0 eq). The reaction mixture is stirred at rt over 17 h, diluted with EA, followed by water and brine. The phases are separated and the aq. layer is extracted with EA (3×). The combined organic layer is dried over MgSO$_4$, filtered and solvent removed in vacuo to give a yellow oil, that is purified by preparative HPLC/MS(I). The title compound is obtained as a beige solid (0.17 g, 34%). LC-MS (A): $t_R$=1.21 min; [M+H]$^+$: 965.06.

4. (2R,3R,4S,5R,6S)-2-(Acetoxymethyl)-6-(((4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate (Intermediate 8)

To a solution of (2R,3R,4S,5R,6S)-2-(acetoxymethyl)-6-(((4-hydroxy-1-(((1,1,1-trichloro-2-methylpropan-2-yl)oxy)carbonyl)piperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate (0.17 g, 0.17 mmol) in THF (12.0 mL) and glacial acetic acid (0.3 mL) is added zinc powder (0.114 g, 1.74 mmol, 10.0 eq). The reaction mixture is stirred for 17 h, filtered and diluted with EA and water. The layer are separated, the aqueous layer is extracted with EA and the combined organic layer washed with brine, dried over MgSO$_4$, filtered and solvent removed in vacuo to give Intermediate 8 as a white solid (0.145 g; >99%), that is used without further purification. LC-MS (A): $t_R$=0.87 min; [M+H]$^+$: 761.01.

Intermediate 8R (2R,3R,4S,5R,6S)-2-(Acetoxymethyl)-6-(((R)-(4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate

1. 2-((2-(Trifluoromethyl)benzyl)thio)quinoline

To a solution of 2-quinolinethiol (1.0 g, 5.9 mmol) in toluene (15.0 mL) is added DBU (0.898 mL, 5.9 mmol). The reaction mixture is stirred at rt for 0.5 h before 2-(trifluoromethyl)benzyl bromide (1.44 g, 5.9 mmol, 1.0 eq) is added. The solution is stirred at rt for 17 h, concentrated under reduced pressure to give a solid. Trituration from Hept gave a yellow/orange solid as the title compound (1.24 g, >99%). LC-MS (A): $t_R$=1.16 min; [M+H]$^+$: 320.09.

2. 4-((Quinolin-2-ylthio)(2-(trifluoromethyl)phenyl)methyl)piperidin-4-ol 2-((2-(Trifluoromethyl)benzyl)thio)quinoline (0.90 g, 2.54 mmol) is dissolved in THF (45.0 mL) and cooled to −78° C. n-BuLi (1.6M in hexane, 4.75 mL, 7.61 mmol, 3.0 eq) is added and the reaction mixture is stirred at −78° C. for 1 h. 1,1,1-Trichloro-2-methylpropan-2-yl 4-oxopiperidine-1-carboxylate (described in Intermediate 8 Step 1.) (0.84 g, 2.70 mmol, 1.1 eq) in THF (19.0 mL) is added and the reaction mixture is allowed to warm up to −70° C. After 2 h at −70° C. the reaction is quenched with aq. sat. NH$_4$Cl, diluted with EA, the layers are separated and the aqueous layer is extracted with EA (3×). The combined organic layer is washed with brine, dried over MgSO$_4$, filtered and solvent removed in vacuo to give the title compound as a yellow oil, that is not further purified (1.04 g). LC-MS (A): $t_R$=0.81 min; [M+H]$^+$: 419.11.

3. 1,1,1-Trichloro-2-methylpropan-2-yl 4-hydroxy-4-((quinolin-2-ylthio)(2-(trifluoromethyl)phenyl)methyl)piperidine-1-carboxylate 4-((Quinolin-2-ylthio)(2-(trifluoromethyl)phenyl)methyl)piperidin-4-ol (1.04 g, 2.49 mmol) is dissolved in DCM (25.0 mL) and 2,2,2-trichloro-1,1-dimethylethyl chloroformate (0.61 g, 2.49 mmol, 1.0 eq) and DIPEA (1.28 mL, 7.46 mmol, 3.0 eq) are added. The reaction mixture is stirred at rt for 4 h, then partitioned between DCM and water, the layers are separated and the aqueous layer is extracted with DCM (3×). The combined organic layer is dried over MgSO$_4$, filtered and solvent removed in vacuo to give an orange oil. The crude is purified by preparative HPLC/MS (I) to recover the title compound as a white solid (0.82 g, 53%). LC-MS (A): $t_R$=1.24 min; [M+H]$^+$: 621.13.

4. 1,1,1-Trichloro-2-methylpropan-2-yl (R)-4-hydroxy-4-((quinolin-2-ylthio)(2-(trifluoromethyl)phenyl)methyl)piperidine-1-carboxylate Chiral separation over chiral preparative HPLC (II) of 1,1,1-trichloro-2-methylpropan-2-yl 4-hydroxy-4-((quinolin-2-ylthio)(2-(trifluoromethyl)phenyl)methyl)piperidine-1-carboxylate (1.54 g) yielded the title compound (0.71 g). Chiral analytical HPLC (E): $t_R$=1.81 min.

5. 1,1,1-Trichloro-2-methylpropan-2-yl (R)-4-hydroxy-4-(mercapto(2-(trifluoromethyl)phenyl)methyl)piperidine-1-carboxylate To a solution of 1,1,1-trichloro-2-methylpropan-2-yl (R)-4-hydroxy-4-((quinolin-2-ylthio)(2-(trifluoromethyl)phenyl)methyl)piperidine-1-carboxylate (0.71 g, 1.14 mmol) in acetic acid (50.0 mL) is added NaCNBH$_3$ (0.38 g, 5.71 mmol, 5.0 eq). The reaction mixture is stirred at rt for 72 h, quenched with water (9.0 mL), and stirred for 1 h. DCM is added, the layers are separated, the aqueous layer is extracted with DCM, the combined organic layer is washed with brine, dried over MgSO$_4$ and solvent is removed in vacuo to give a yellow oil. The crude material is purified by preparative HPLC/MS(II) to yield the title compound as a colourless oil (0.28 g, 49%). LC-MS (A): $t_R$=1.15 min; [M+H]$^+$: 494.01. Chiral analytical HPLC (F): $t_R$=1.947 min.

6. (2R,3R,4S,5R,6S)-2-(Acetoxymethyl)-6-(((R)-(4-hydroxy-1-(((1,1,1-trichloro-2-methylpropan-2-yl)oxy)carbonyl)piperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate To a solution of Intermediate 3 (0.31 g, 0.563 mmo, 1.0 eq) in EA (36.0 mL) are added TBAB (0.045 g, 0.141 mmol, 0.25 eq), aq. 1M Na$_2$CO$_3$ (6.0 mL) and 1,1,1-trichloro-2-methylpropan-2-yl (R)-4-hydroxy-4-(mercapto(2-(trifluoromethyl)phenyl)methyl)piperidine-1-carboxylate (0.28 g, 0.563 mmol). The reaction mixture is stirred at rt for 17 h, diluted with EA, followed by water and brine. The phases are separated and the aq. layer is extracted with EA (3×). The combined organic layer is dried over MgSO$_4$, filtered and solvent removed in vacuo to give a yellow oil. The crude is purified by preparative HPLC/MS(I) to yield the title compound as a beige solid (0.059 g, 39%). LC-MS (A): $t_R$=1.23 min; [M+H]$^+$: 965.28. Chiral analytical HPLC (G): $t_R$=1.59 min.

7. (2R,3R,4S,5R,6S)-2-(Acetoxymethyl)-6-(((S)-(4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate (Intermediate 8R)

To a solution of (2R,3R,4S,5R,6S)-2-(acetoxymethyl)-6-(((R)-(4-hydroxy-1-(((1,1,1-trichloro-2-methylpropan-2-yl)oxy)carbonyl)piperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate (0.25 g, 0.26 mmol) in THF (18.0 mL) and glacial acetic acid (0.75 mL) is added zinc powder (0.17 mg, 2.6 mmol, 10.0 eq). The reaction mixture is stirred at rt for 17 h, filtered and partitioned between EA and water. The layers are separated, the aqueous layer is extracted with EA, the combined organic layer is washed with brine, dried over MgSO$_4$, filtered and solvent removed in vacuo to give a white solid. The crude is purified by preparative HPLC/MS(I) to give the title compound as a white powder (0.13 g, 68%). LC-MS (A): $t_R$=0.87 min; [M+H]$^+$: 761.13. Chiral analytical HPLC (H): $t_R$=2.0 min. $^1$H NMR (400 MHz, MeOD) δ: 8.41 (s, 1H), 8.16 (d, J=8.0 Hz, 1H), 7.76 (d, J=7.9 Hz, 1H), 7.69 (t, J=7.6 Hz, 1H), 7.60 (dd, J$_1$=6.7 Hz, J$_2$=8.6 Hz, 2H), 7.53 (t, J=7.7 Hz, 1H), 5.78 (t, J=10.4 Hz, 1H), 5.54 (d, J=3.0 Hz, 1H), 5.33 (dd, J$_1$=3.2 Hz, J$_2$=10.8 Hz, 1H), 4.57 (s, 1H), 4.52 (d, J=9.9 Hz, 1H), 4.25-4.08 (m, 3H), 3.33 (m), 3.29-3.06 (m, 3H), 2.68 (dd, J$_1$=1.8 Hz, J$_2$=14.7 Hz, 1H), 2.10 (s, 3H), 2.07 (s, 3H), 1.92-1.77 (m, 2H), 1.75 (s, 3H), 1.35-1.09 (m, 2H).

Intermediate 8S (2R,3R,4S,5R,6S)-2-(Acetoxymethyl)-6-(((S)-(4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate (Intermediate 8S)

The title compound, the S-epimer, is prepared from 2-(trifluoromethyl)benzyl bromide and 2-quinolinethiol according to the procedure described for Intermediate 8R (S-epimer is obtained at Step 4. through chiral separation) to yield a white solid (0.18 g). LC-MS (A): $t_R$=0.87 min; [M+H]$^+$: 761.01. Chiral analytical HPLC (H): $t_R$=2.91 min.

Intermediate 8A (2R,3R,4S,5R,6S)-2-(Acetoxymethyl)-6-(((3-hydroxyazetidin-3-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate Intermediate 8A is prepared from 2-((2-(trifluoromethyl)benzyl)thio)quinoline and 1,1,1-trichloro-2-methylpropan-2-yl 3-oxoazetidine-1-carboxylate in analogy to Intermediate 8 to yield a light yellow solid (0.11 g). LC-MS(A) $t_R$=0.84 min, [M+H]$^+$=733.18.

Intermediate 9

(2R,3R,4S,5R,6S)-2-(Acetoxymethyl)-4-azido-6-((2-hydroxy-2-methyl-1-(2-(trifluoromethyl)phenyl)propyl)thio)tetrahydro-2H-pyran-3,5-diyl diacetate

1. 1-Mercapto-2-methyl-1-(2-(trifluoromethyl)phenyl)propan-2-ol

1-Mercapto-2-methyl-1-(2-(trifluoromethyl)phenyl)propan-2-ol is synthesized from 1-(bromomethyl)-2-(trifluoromethyl)benzene and acetone according to the procedures described for the synthesis of 1-mercapto-2-methyl-1-phenylpropan-2-ol (Intermediate 5). LC-MS(A) $t_R$=0.93 min, [M+H]$^+$=no mass. $^1$H NMR (400 MHz, CDCl$_3$) δ: 8.04 (d, J=8.0 Hz, 1H), 7.64 (d, J=8.3 Hz, 1H), 7.55 (t, J=7.8 Hz, 1H), 7.37 (t, J=7.8 Hz, 1H), 4.37 (d, J=7.3 Hz, 1H), 2.06 (d, J=6.8 Hz, 1H), 1.48 (s, 3H), 1.12 (s, 3H).

2. (2R,3R,4S,5R,6S)-2-(Acetoxymethyl)-4-azido-6-((2-hydroxy-2-methyl-1-(2-(trifluoromethyl)phenyl)propyl)thio)tetrahydro-2H-pyran-3,5-diyl diacetate (Intermediate 9)

To a solution of Intermediate 2 (0.71 g, 1.8 mmol) in EA (30.0 mL) are added TBAB (014 g, 0.45 mmol, 0.25 eq), aq. 1M Na$_2$CO$_3$ (15.0 mL) and 1-mercapto-2-methyl-1-(2-(trifluoromethyl)phenyl)propan-2-ol (0.45 g, 1.8 mmol, 1.0 eq). The reaction mixture is stirred at rt for 72 h, then diluted with EA, followed by water and brine. The phases are separated and the aq. layer is extracted with EA (3×). The combined organic layer is dried over MgSO$_4$, filtered and solvent removed in vacuo to give an orange foam. The crude is purified by Flash Master (Büchi, product added on isolute, 20 g column, 15 mL/min, 15 mL fractions, Hept/EA 100/0 to 7/3, Rf(Hept/EA 7/3)=0.17, stained with KMnO$_4$) to give the title compound as a colorless oil (0.67 g, 66%). LC-MS (A): t$_R$=1.02 min; [M+H]$^+$: 564.18.

Intermediate 10

((2R,3R,4S,5R,6R)-3-Acetoxy-6-bromo-5-methoxy-4-(4-(3,4,5-trifluorophenyl)-1H-1,2,3-triazol-1-yl)tetrahydro-2H-pyran-2-yl)methyl acetate 1. (2R,3R,4S,5R,6S)-2-(Acetoxymethyl)-4-azido-6-(methylthio)tetrahydro-2H-pyran-3,5-diyl diacetate To a solution of Intermediate 1 (14.50 g, 38.8 mmol) in DCM (300.0 mL) at rt are added TMS-SMe (15.0 mL, 103.00 mmol, 2.6 eq) and molecular sieves (30.0 g, 4 Å) followed by TMS-OTf (6.5 mL, 35.3 mmol, 0.9 eq). The reaction mixture is stirred at rt for 15 h, then quenched with aq. sat. Na$_2$CO$_3$. The resulting solution is stirred for 1 h then diluted with DCM, followed by water. The phases are separated and the aq. phase is extracted with DCM (2×). The combined organic layer is dried over Na$_2$SO$_4$, filtered and solvent removed in vacuo to give an oil. The crude is purified by Flash Master (ISCO, product added on isolute, 220 g column, Hept/EA 100/0 to 60/40) to give the title compound as a colourless oil (13.5 g, 96%). LC-MS (A): t$_R$=0.85 min; [M+H]$^+$: 314.16.

2. (2R,3R,4S,5R,6S)-2-(Acetoxymethyl)-6-(methylthio)-4-(4-(3,4,5-trifluorophenyl)-1H-1,2,3-triazol-1-yl)tetrahydro-2H-pyran-3,5-diyl diacetate To a solution of (2R,3R,4S,5R,6S)-2-(acetoxymethyl)-4-azido-6-(methylthio)tetrahydro-2H-pyran-3,5-diyl diacetate (14.02 g, 38.8 mmol) in DMF (200.0 mL) are added 3,4,5-trifluorophenylacetylene (6.24 g, 38.8 mmol, 1.0 eq), CuI (2.22 g, 11.6 mmol, 0.3 eq) and DIPEA (19.9 mL, 116.0 mmol, 3.0 eq). The reaction mixture is stirred at 45° C. for 1 h, cooled to rt, diluted with EA and filtered. The organic layer is washed with aq. sat. NH$_4$Cl, followed by brine, dried over Na$_2$SO$_4$, filtered and solvent removed in vacuo to give the title compound as a beige solid (21.24 g, >99%), that is used without further purification. LC-MS (A): t$_R$=0.98 min; [M+H]$^+$: 517.81

3. (2R,3R,4S,5R,6S)-2-(Hydroxymethyl)-6-(methylthio)-4-(4-(3,4,5-trifluorophenyl)-1H-1,2,3-triazol-1-yl)tetrahydro-2H-pyran-3,5-diol NaOMe (3.05 g, 56.5 mmol, 1.5 eq) is added at rt to a suspension of (2R,3R,4S,5R,6S)-2-(acetoxymethyl)-6-(methylthio)-4-(4-(3,4,5-trifluorophenyl)-1H-1,2,3-triazol-1-yl)tetrahydro-2H-pyran-3,5-diyl diacetate (21.24 g, 37.7 mmol) in MeOH (400.0 mL) and stirring is continued at rt for 48 h. The reaction mixture is neutralized with the addition of DOWEX 50WX2 (until pH=6-7), filtered and solvent removed in vacuo to recover the crude that is dissolved in EA. The organic layer is washed with water, dried over Na$_2$SO$_4$, filtered and solvent removed in vacuo to give a pale brown solid (17.12 g, >99%), that is used without further purification. LC-MS (A): t$_R$=0.65 min; [M+H]$^+$: 392.12

4. (4aR,6S,7R,8R,8aR)-2,2-Dimethyl-6-(methylthio)-8-(4-(3,4,5-trifluorophenyl)-1H-1,2,3-triazol-1-yl)hexahydropyrano[3,2-d][1,3]dioxin-7-ol 2,2-Dimethoxypropane (14.1 mL, 115.0 mmol, 3.0 eq), and CSA (4.38 g, 18.9 mmol, 0.5 eq) are added to a solution of (2R,3R,4S,5R,6S)-2-(hydroxymethyl)-6-(methylthio)-4-(4-(3,4,5-trifluorophenyl)-1H-1,2,3-triazol-1-yl)tetrahydro-2H-pyran-3,5-diol (14.76 g, 37.7 mmol), in DMF (200.0 mL). The reaction mixture is heated at 50° C. for 1 h, cooled to rt and quenched with EA and brine. The phases are separated and the aq. layer is extracted with EA (3×). The combined organic layer is dried over Na$_2$SO$_4$, filtered and solvent removed in vacuo to give the crude, that is purified by Flash Master (ISCO, product added on isolute, 120 g column, Hept/EA 95/5 to 55/45) The title compound is obtained as a beige solid (9.85 g, 61%). LC-MS (A): t$_R$=0.91 min; [M+H]$^+$: 432.14

5. 1-((4aR,6S,7R,8S,8aR)-7-Methoxy-2,2-dimethyl-6-(methylthio)hexahydropyrano[3,2-d][1,3]dioxin-8-yl)-4-(3,4,5-trifluorophenyl)-1H-1,2,3-triazole To a solution of (4aR,6S,7R,8R,8aR)-2,2-dimethyl-6-(methylthio)-8-(4-(3,4,5-trifluorophenyl)-1H-1,2,3-triazol-1-yl)hexahydropyrano[3,2-d][1,3]dioxin-7-ol (9.85 g, 22.8 mmol) in DMF (200.0 mL) are added molecular sieves (4 Å), followed by Ag$_2$O (26.46 g, 114.00 mmol, 5.0 eq). The reaction mixture is stirred for 15 min at rt, then MeI (7.34 mL, 114.0 mmol, 5.0 eq) is added and stirring at rt is continued for 15 h. The mixture is filtered, diluted with EA, followed by water, the phases are separated and the aqueous layer is extracted with EA (2×). The combined organic layer is dried over Na$_2$SO$_4$, filtered and solvent removed in vacuo to give a beige solid, that is purified by Flash Master (ISCO, product added on isolute, 120 g column, Hept/EA 90/10 to 30/70 Rf(Hept/EA 1/1)=0.52, UV-active). The title compound is obtained as a white powder (6.18 g, 61%). LC-MS (A): t$_R$=0.99 min; [M+H]$^+$: 446.21.

6. (2R,3R,4S,5R,6S)-2-(Hydroxymethyl)-5-methoxy-6-(methylthio)-4-(4-(3,4,5-trifluorophenyl)-1H-1,2,3-triazol-1-yl)tetrahydro-2H-pyran-3-ol To a solution of 1-((4aR,6S,7R,8S,8aR)-7-methoxy-2,2-dimethyl-6-(methylthio)hexahydropyrano[3,2-d][1,3]dioxin-8-yl)-4-(3,4,5-trifluorophenyl)-1H-1,2,3-triazole (1.55 g, 2.96 mmol, 1.0 eq) in THF (35.0 mL) is added a mixture of AcOH/water (1:1, 100.0 mL) and the solution is stirred at 65° C. for 15 h. The reaction mixture is diluted with EA, followed by aq. sat. NaHCO$_3$. The layers are separated, the aq. phase is extracted with EA (2×). The combined organic layer is dried over Na$_2$SO$_4$, filtered and solvent removed in vacuo to recover the title compound as a beige solid (1.63 g, >99%), that is used without further purification. LC-MS (A): t$_R$=0.80 min; [M+H]$^+$: 405.96

7. ((2R,3R,4S,5R,6S)-3-Acetoxy-5-methoxy-6-(methylthio)-4-(4-(3,4,5-trifluorophenyl)-1H-1,2,3-triazol-1-yl)tetrahydro-2H-pyran-2-yl)methyl acetate To a cooled (0° C.) solution of (2R,3R,4S,5R,6S)-2-(hydroxymethyl)-5-methoxy-6-(methylthio)-4-(4-(3,4,5-trifluorophenyl)-1H-1,2,3-triazol-1-yl)tetrahydro-2H-pyran-3-ol (5.64 g, 13.9 mmol, 1.0 eq) in pyridine (99.0 mL) is added Ac$_2$O (8.0 mL, 83.4 mmol, 6.0 eq). The reaction mixture is stirred at rt for 2 h, then concentrated under reduced pressure. The resulting residue is partitioned between EA and water, the phases are separated and the organic layer is washed with water, dried over $Na_2SO_4$, filtered and solvent removed in vacuo to give a beige solid. Purification by Flash master (ISCO, product added on isolute, 1200 g column, Hept/EA 95/5 to 30/70) yielded the title compound as a white solid (5.66 g, 83%). LC-MS (A): $t_R$=1.00 min; [M+H]$^+$: 490.07

8. ((2R,3R,4S,5R,6RS)-3-Acetoxy-6-bromo-5-methoxy-4-(4-(3,4,5-trifluorophenyl)-1H-1,2,3-triazol-1-yl)tetrahydro-2H-pyran-2-yl)methyl acetate (Intermediate 10)

NBS (4.00 g, 22.4 mmol, 2.0 eq) is added to a solution of ((2R,3R,4S,5R,6S)-3-acetoxy-5-methoxy-6-(methylthio)-4-(4-(3,4,5-trifluorophenyl)-1H-1,2,3-triazol-1-yl)tetrahydro-2H-pyran-2-yl)methyl acetate (5.66 g, 11.2 mmol) in DCM (165.0 mL). The reaction mixture is stirred at rt for 15 h, quenched with water and diluted with DCM. The layers are separated and the aq. layer is extracted with DCM (2×). The combined organic layer is washed with brine, dried over $Na_2SO_4$, filtered and solvent removed in vacuo to give the crude. Purification by Flash Master (ISCO, product added on isolute, 80 g column, Hept/EA 100/0 to 30/70) yielded Intermediate 10 as a beige solid (1.72 g, 29%). LC-MS (A): $t_R$=1.01 min; [M+H]$^+$: 524.02. $^1$H NMR (500 MHz, $CDCl_3$) δ: 7.82 (s, 1H), 7.45 (dd, $J_1$=7.3 Hz, $J_2$=7.3 Hz, 2H), 6.87 (d, J=3.6 Hz, 1H), 5.60 (d, J=2.3 Hz, 1H), 5.01 (dd, $J_1$=10.7 Hz, $J_2$=2.9 Hz, 1H), 4.63 (t, J=6.6 Hz, 1H), 4.48 (dd, $J_1$=10.7 Hz, $J_2$=3.6 Hz, 1H), 4.24 (dd, $J_1$=11.3 Hz, $J_2$=6.4 Hz, 1H), 4.18 (dd, $J_1$=11.3 Hz, $J_2$=6.4 Hz, 1H), 3.39 (s, 3H), 2.10 (s, 3H), 2.08 (s, 3H).

Intermediate 11

((2R,3R,4S,5R,6R)-3-Acetoxy-6-bromo-5-ethoxy-4-(4-(3,4,5-trifluorophenyl)-1H-1,2,3-triazol-1-yl)tetrahydro-2H-pyran-2-yl)methyl acetate Intermediate 11 is prepared from Intermediate 1 in analogy to Intermediate 10. In Step 5. EtI is added to the reaction mixture and the Intermediate 11 is obtained as a white powder. LC-MS (A): $t_R$=1.03 min; [M+H]$^+$: 538.15

Intermediate 12

((2R,3R,4S,5R,6S)-3-Acetoxy-6-(((4-hydroxypiperidin-4-yl)(2-(trifluoromethyl)phenyl)methyl)thio)-5-methoxy-4-(4-(3,4,5-trifluorophenyl)-1H-1,2,3-triazol-1-yl)tetrahydro-2H-pyran-2-yl)methyl acetate Intermediate 12 is prepared from (2R,3R,4S,5R,6S)-2-(acetoxymethyl)-6-(((4-hydroxy-1-(((1,1,1-trichloro-2-methylpropan-2-yl)oxy)carbonyl)piperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate (Intermediate 8 Step 3).

1. 1,2,2,2-Trichloroethyl 4-hydroxy-4-((((4aR,6S,7R,8S,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)thio)(2-(trifluoromethyl)phenyl)methyl)piperidine-1-carboxylate 2,2,2-Trichloroethyl 4-hydroxy-4-((((4aR,6S,7R,8S,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)thio)(2-(trifluoromethyl)phenyl)methyl)piperidine-1-carboxylate is obtained in 3 steps starting from Intermediate 8 Step 3. according to the procedures described for Intermediate 10 Step 3-5 to yield a white powder. LC-MS(A) $t_R$=1.25 min, [M+H]$^+$=891.07.

2. ((2R,3R,4S,5R,6S)-3-Acetoxy-6-(((4-hydroxypiperidin-4-yl)(2-(trifluoromethyl)phenyl)methyl)thio)-5-methoxy-4-(4-(3,4,5-trifluorophenyl)-1H-1,2,3-triazol-1-yl)tetrahydro-2H-pyran-2-yl)methyl acetate (Intermediate 12)

To a solution of 1,2,2,2-trichloroethyl 4-hydroxy-4-((((4aR,6S,7R,8S,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)thio)(2-(trifluoromethyl)phenyl)methyl)piperidine-1-carboxylate (0.16 g, 0.18 mmol) in THF (10.0 mL) and AcOH (0.15 mL) is added zinc (0.12 g, 1.85 mmol, 10.0 eq). The reaction mixture is stirred at rt for 15 h, filtered and partitioned between EA and water. The layers are separated, the aqueous layer is extracted with EA and the combined organic layer is washed with brine, dried over $MgSO_4$, filtered and solvent removed in vacuo to give the title compound as a white solid (0.053 g, >99%), that was not further purified. LC-MS(A) $t_R$=0.85 min, [M+H]$^+$ =688.95.

PREPARATION OF THE REFERENCE EXAMPLES

Reference Example 1

(2R,3R,4S,5R,6S)-2-(Hydroxymethyl)-6-((2-methoxy-1-phenylethyl)thio)-4-(4-(3,4,5-trifluorophenyl)-1H-1,2,3-triazol-1-yl)tetrahydro-2H-pyran-3,5-diol (2.30.100.OMe)

1. (2R,3R,4S,5R,6S)-2-(Acetoxymethyl)-6-((2-methoxy-1-phenylethyl)thio)-4-(4-(3,4,5-trifluorophenyl)-1H-1,2,3-triazol-1-yl)tetrahydro-2H-pyran-3,5-diyl diacetate To a solution of Intermediate 3 (0.088 g, 0.15 mmol) in EA (1.65 mL) are added TBAB (0.012 g, 0.037 mmol, 0.25 eq), aq. 1M $Na_2CO_3$ (0.8 mL) and 2-methoxy-1-phenylethane-1-thiol (0.038 g, 0.225 mmol, 1.5 eq). The reaction mixture is stirred for 17 at rt, diluted with EA, followed by water and brine. The phases are separated and the aq. layer is extracted with EA (3×). The combined organic layer is dried over $MgSO_4$, filtered and solvent removed in vacuo. The crude material is purified by preparative HPLC/MS (II) to yield the title compound as a white solid (0.019 g, 20%). LC-MS (A): $t_R$=1.12 min; [M+H]$^+$: 638.03.

2. (2R,3R,4S,5R,6S)-2-(Hydroxymethyl)-6-((2-methoxy-1-phenylethyl)thio)-4-(4-(3,4,5-trifluorophenyl)-1H-1,2,3-triazol-1-yl)tetrahydro-2H-pyran-3,5-diol (2.30.100.OMe)

(2R,3R,4S,5R,6S)-2-(Acetoxymethyl)-6-((2-methoxy-1-phenylethyl)thio)-4-(4-(3,4,5-trifluorophenyl)-1H-1,2,3-triazol-1-yl)tetrahydro-2H-pyran-3,5-diyl diacetate (0.019 g, 0.029 mmol) is dissolved in MeOH (1.4 mL) and NaOMe (0.003 g, 0.0588 mmol, 2.0 eq) is added. The reaction mixture is stirred at rt for 17 h. The mixture is neutralized with HCl 1N, concentrated in vacuo and purified by preparative HPLC/MS (I) to yield the titled compound as a white solid (0.01, 67%). LC-MS (A): $t_R$=0.85 min; [M+H]$^+$: 512.26.

Following examples are prepared starting from a thiol and Intermediate 3, according to the procedures described for Reference Example 1. LC-MS and Gal-3 inhibition data are listed in Table 1 below. The LC-MS conditions used were LC-MS (A).

TABLE 1

| Example | Name | $t_R$ [min] | [M + H]$^+$ | IC$_{50}$ [uM] |
|---|---|---|---|---|
| 2.30.100.OMe Ref. 1 | (2R,3R,4S,5R,6S)-2-(Hydroxymethyl)-6-((2-methoxy-1-phenylethyl)thio)-4-(4-(3,4,5-trifluorophenyl)-1H-1,2,3-triazol-1-yl)tetrahydro-2H-pyran-3,5-diol | 0.85 | 512.26 | 2.90 |
| 2.55.100. Ref. 2 | (2R,3R,4S,5R,6S)-2-(Hydroxymethyl)-6-((1-phenylethyl)thio)-4-(4-(3,4,5-trifluorophenyl)-1H-1,2,3-triazol-1-yl)tetrahydro-2H-pyran-3,5-diol | 0.88 | 481.74 | 4.03 |
| 2.54.100. Ref. 3 | (2S,3R,4S,5R,6R)-2-((Cyclopropyl(phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.92 | 508.28 | 3.21 |

Preparation of the Compounds of Structure 1 and Examples Thereof

Example 2.30.100R (2S,3R,4S,5R,6R)-2-(((R)-2-Hydroxy-1-phenylethyl)thio)-6-(hydroxymethyl)-4-(4-(3,4,5-trifluorophenyl)-1H-1,2,3-triazol-1-yl)tetrahydro-2H-pyran-3,5-diol 1. Ethyl (R)-2-((dimethylcarbamothioyl)thio)-2-phenylacetate To a solution of S-ethylmandelate (1.0 g, 5.55 mmol) in toluene (50.0 mL) are added PPh$_3$ (2.9 g, 11.1 mmol, 2.0 eq) and Ziram (1.2 g, 3.9 mmol, 0.7 eq). The suspension is cooled to 2-4° C., DEAD (40% in toluene, 5.05 mL, 11.1 mmol, 2.0 eq) is added dropwise and the reaction mixture stirred at rt over 17 h. The solvent is removed in vacuo and the crude product directly purified by column chromatography on silica gel eluting with (Hept/EA 4/1) to give ethyl (R)-2-((dimethylcarbamothioyl)thio)-2-phenylacetate as an oil (1.3 g, 81%). LC-MS (B): $t_R$=1.04 min; [M+H]$^+$: 284.21.

2. (R)-2-Mercapto-2-phenylethan-1-ol

To a cooled solution (0°) of ethyl (R)-2-((dimethylcarbamothioyl)thio)-2-phenylacetatein (1.27 g, 4.48 mmol) in Et$_2$O (50.0 mL) is added LAH (2M in THF, 4.5 mL, 8.96 mmol, 2.0 eq). The cooling bath is removed and the reaction mixture allowed to warm up to rt and heated to reflux for 1 h. The suspension is cooled to rt, carefully quenched with water and Et$_2$O, the pH adjusted to 4 through addition of aq. 2M HCl. The phases are separated, the aq. phase is extracted with Et$_2$O (2×), the combined organic layer is dried over MgSO$_4$, filtered and solvent removed in vacuo. The crude is purified by preparative HPLC/MS(II) to yield (R)-2-mercapto-2-phenylethan-1-ol as an oil (0.4 g, 57%). LC-MS (B): $t_R$=072 min; [M+H]$^+$: no mass seen. $^1$H NMR (400 MHz, CDCl3) δ: 7.38 (m, 4H), 7.30-7.33 (m, 1H), 4.13 (q, J=7.3 Hz, 1H), 3.96 (dd, J$_1$=6.5 Hz, J$_2$=11.3 Hz, 1H), 3.84 (dd, J$_1$=7.5 Hz, J$_2$=11.0 Hz, 1H), 2.03 (s, 1H), 2.00 (d, J=7.5 Hz, 1H).

3. (2S,3R,4S,5R,6R)-4-(4-(3,4,5-Trifluorophenyl)-1H-1,2,3-triazol-1-yl)-2-(((R)-2-hydroxy-1-phenylethyl)thio)-6-(hydroxymethyl)tetrahydro-2H-pyran-3,5-diol (2.30.100R.)

To a solution of Intermediate 3 (0.8 g, 1.46 mmol) in EA (32.0 mL) are added TBAB (0.117 g, 0.364 mmol, 0.25 eq) and aq. 1M Na$_2$CO$_3$ (16.0 mL). The reaction mixture is stirred at rt for 16 h, diluted with EA, the layers are separated and the aqueous layer is extracted with EA. The combined organic layer is dried over MgSO$_4$, and solvent removed in vacuo. Purification over preparative HPLC/MS(I) yielded the desired acetyl-protected thioglycoside as an oil (0.085 g, 9%). LC-MS (B): $t_R$=1.03 min; [M+H]$^+$: 623.95.

The above thioglycoside is dissolved in 0.02M NaOMe solution in MeOH and stirred at rt over 2 h. The solvent is removed in vacuo and the residue purified by preparative HPLC/MS(I) to yield the title compound (0.0041 g, 6%) as a solid. LC-MS (B): $t_R$=0.77 min; [M+H]$^+$: 498.17.

Example 1.30.101

(2S,3R,4S,5R,6R)-2-((1-(2-Bromophenyl)-2-hydroxyethyl)thio)-4-(4-(3-fluorophenyl)-1H-1,2,3-triazol-1-yl)-6-(hydroxymethyl)tetrahydro-2H-pyran-3,5-diol 1. Ethyl 2-(2-bromophenyl)-2-diazoacetate Ethyl-(2-bromophenyl)acetate (1.0 g, 4.11 mmol) and p-ABSA (1.28 g, 5.35 mmol, 1.3 eq) are dissolved in MeCN (20.0 mL) and the solution cooled to 0° C. DBU (0.77 mL, 5.35 mmol, 1.45 eq) is added, and stirring continued at 0° C. After 20 min the cooling bath is removed and the reaction mixture stirred at rt for 15 h. The mixture is diluted with DCM, and the organic phase washed with water, dried over MgSO$_4$, filtered and the solvent removed in vacuo. The residue is purified by column chromatography on silica gel eluting with (Hept/EA 4/1) to give ethyl 2-(2-bromophenyl)-2-diazoacetate (1.0 g, 90%) as an oil. LC-MS (C): $t_R$=1.09 min; [M+H]$^+$: no mass.

2. Ethyl-2-(2-bromophenyl)-2-hydroxyacetate

Ethyl 2-(2-bromophenyl)-2-diazoacetate (1.0 g, 3.72 mmol) is added to 0.5M HClO$_4$ in dioxane/water=6/4. After 2 h at rt, the reaction mixture is poured over water and extracted with DCM (2×), the combined organic layer is dried over MgSO$_4$, filtered and solvent removed in vacuo. The residue is purified by preparative HPLC/MS (II) to afford ethyl-2-(2-bromophenyl)-2-hydroxyacetate as an oil (0.69 g, 72%). LC-MS (C): $t_R$=0.80 min; [M+H]$^+$: 258.90.

3. (2S,3R,4S,5R,6R)-2-((1-(2-Bromophenyl)-2-hydroxyethyl)thio)-4-(4-(3-fluorophenyl)-1H-1,2,3-triazol-1-yl)-6-(hydroxymethyl)tetrahydro-2H-pyran-3,5-diol (1.30.101.)

The last three steps are performed according to the procedures described for Example 1.30.100R to afford the title compound (1.30.101.) as a solid (0.065 g). LC-MS (C): $t_R$=0.74 min; [M+H]$^+$: 539.92.

Example 2.30.105

(2S,3R,4S,5R,6R)-2-((2-Hydroxy-1-(2-isopropylphenyl)ethyl)thio)-6-(hydroxymethyl)-4-(4-(3,4,5-trifluorophenyl)-1H-1,2,3-triazol-1-yl)tetrahydro-2H-pyran-3,5-diol

1. Methyl 2-(2-bromophenyl)-2-hydroxyacetate

The title compound is prepared from methyl-(2-bromophenyl)acetate according to the procedures described in Example 1.30.101. (Step 1 & Step 2). LC-MS (C): $t_R$=0.71 min; [M+H]$^+$: 244.86.

2. Methyl 2-acetoxy-2-(2-bromophenyl)acetate

Methyl 2-(2-bromophenyl)-2-hydroxyacetate (2.46 g, 10.0 mmol) is dissolved in pyridine (20.0 mL). Acetic anhydride (1.42 mL, 15.1 mmol, 1.5 eq) is added and the reaction mixture stirred at rt for 72 h. Removal of the solvent under vacuum yielded the title compound (2.99, >99%) that is not further purified. LC-MS (C): $t_R$=0.93 min; [M+H]$^+$: 288.82.

3. Methyl 2-acetoxy-2-(2-(prop-1-en-2-yl)phenyl)acetate

Methyl 2-acetoxy-2-(2-bromophenyl)acetate (1.50 g, 5.22 mmol) and isopropenyl boronic acid pinacolester (1.55 mL, 7.84 mmol, 1.5 eq) are dissolved in dioxane (50.0 mL) and water (12.0 mL). $K_2CO_3$ and Pd(Ph$_3$)$_4$ are added and the reaction mixture is heated at 100° C. for 17 h. The mixture is cooled to rt, diluted with EA, the layers are separated and the organic layer is washed with water, dried over MgSO$_4$, filtered and solvent removed in vacuo. The residue is purified by column chromatography on silica gel eluting with (Hept/EA 4/1) to give methyl 2-acetoxy-2-(2-(prop-1-en-2-yl)phenyl)acetate (0.96 g, 74%). LC-MS (C) $t_R$=1.0 min; [M+H]$^+$: 248.99.

4. Methyl 2-acetoxy-2-(2-isopropylphenyl)acetate

Methyl 2-acetoxy-2-(2-(prop-1-en-2-yl)phenyl)acetate (0.96 g, 3.87 mmol) is dissolved in THF. Palladium on charcoal is added, followed by MeOH and the reaction mixture is submitted to hydrogenation under 5 bar for 72 h. The suspension is filtered (glass microfiber filters) and the solvent removed undervacuum to yield the title compound (0.93, 96%), that is not further purified. LC-MS (C) $t_R$=1.03 min; [M+H]$^+$: 250.08.

5. Methyl 2-hydroxy-2-(2-isopropylphenyl)acetate

Methyl 2-acetoxy-2-(2-isopropylphenyl)acetate is dissolved in 0.02M NaOMe in MeOH (20.0 mL) and stirred at rt for 1 h. The reaction mixture is poured over water and extracted with EA (2×). The combined organic layer is dried over MgSO$_4$, filtered and solvent removed in vacuo to yield the title compound (0.71 g, 92%), that is not further purified. LC-MS (C) $t_R$=0.83 min; [M+H]$^+$: no mass.

6. Methyl 2-bromo-2-(2-isopropylphenyl)acetate

To a solution of methyl 2-hydroxy-2-(2-isopropylphenyl)acetate (0.715 g, 3.43. mmol) in DCM (20.0 mL), is added pyridine (0.41 mL, 5.15 mmol, 1.5 eq) and SBr$_2$ (0.332 mL, 4.29 mmol, 1.25 eq) and the reaction mixture stirred at rt for 16 h. The mixture is diluted with DCM and washed with water, the organic phase is dried over MgSO$_4$, filtered and solvent removed in vacuo. The residue is purified by column chromatography on silica gel eluting with (Hept/EA 4/1) to give methyl 2-bromo-2-(2-isopropylphenyl)acetate (0.49 g, 53%). LC-MS (C) $t_R$=0.63 min; [M+H]$^+$: 270.04.

7. Methyl 2-(acetylthio)-2-(2-isopropylphenyl)acetate

To a solution of methyl 2-bromo-2-(2-isopropylphenyl)acetate (0.49 g, 1.81 mmol) in acetone (10.0 mL) is added potassium thioacetate (0.41 g, 3.61 mmol, 2.0 eq) and the reaction mixture stirred at rt for 1 h. The mixture is filtered and diluted with EA, washed with water and brine. The organic layer is dried over MgSO$_4$, filtered and solvent removed in vacuo to give the title compound (0.63 g, >99%), that is not further purified. LC-MS (C) $t_R$=1.10 min; [M+H]$^+$: 267.01.

8. 2-Mercapto-2-phenylethan-1-ol

Methyl 2-(acetylthio)-2-(2-isopropylphenyl)acetate (0.4 g, 1.5 mmol) is dissolved in THF (10.0 mL) and the solution is cooled to 0° C. LAH (2M solution in THF 1.5 mL, 3.0 mmol, 2.0 eq) is added dropwise. Upon ending the LAH addition, the cooling bath is removed and the reaction is allowed to reach rt, and it is stirred at rt for 1 h. The mixture is quenched with aq. 1M HCl and extracted with EA (2×). The combined organic layer is dried over MgSO$_4$, filtered and solvent removed in vacuo and the crude is purified by preparative HPLC/MS (II) to give the title compound (0.174, 59%). LC-MS (C) $t_R$=0.92 min; [M+H]$^+$: no mass.

9. (2S,3R,4S,5R,6R)-2-((2-Hydroxy-1-(2-isopropylphenyl)ethyl)thio)-6-(hydroxymethyl)-4-(4-(3,4,5-trifluorophenyl)-1H-1,2,3-triazol-1-yl)tetrahydro-2H-pyran-3,5-diol (2.30.105.)

Aq. 1M $K_2CO_3$ solution (5.0 mL)) is added at rt to a solution of (Intermediate 3) (0.20 g, 0.36 mmol) in EA (10.0 mL). The reaction mixture is stirred at rt for 52 h, diluted with EA, washed with water. The organic layer is dried over MgSO$_4$, filtered and solvent removed in vacuo and the crude is purified by preparative HPLC/MS (I) to give the thioglycoside. LC-MS (A): $t_R$=1.13 min; [M+H]$^+$: 666.00.

The above thioglycoside is dissolved in 0.01M NaOMe solution in MeOH and stirred at rt over 40 min. The solvent is removed in vacuo and the residue purified by preparative HPLC/MS(I) to yield the title compound (0.023 g, 12%). LC-MS (B): $t_R$=0.89 min; [M+H]$^+$: 540.01.

LC-MS and Gal-3 inhibition data from Examples 2.30.100R. to Example 2.30.105. are listed in Table 2 below. The LC-MS conditions used were LC-MS (C).

TABLE 2

| Example | Name | $t_R$ [min] | [M + H]$^+$ | IC$_{50}$ [uM] |
|---|---|---|---|---|
| 2.30.100R. | (2S,3R,4S,5R,6R)-2-(((R)-2-Hydroxy-1-phenylethyl)thio)-6-(hydroxymethyl)-4-(4-(3,4,5-trifluorophenyl)-1H-1,2,3-triazol-1-yl)tetrahydro-2H-pyran-3,5-diol | 0.77 | 498.17 | 0.8 |
| 1.30.101. | (2S,3R,4S,5R,6R)-2-(((1-(2-Bromophenyl)-2-hydroxyethyl)thio)-4-(4-(3-fluorophenyl)-1H-1,2,3-triazol-1-yl)-6-(hydroxymethyl)tetrahydro-2H-pyran-3,5-diol | 0.74 | 539.92 | 1.7 |
| 2.30.105. | (2S,3R,4S,5R,6R)-2-((2-Hydroxy-1-(2-isopropylphenyl) ethyl)thio)-6-(hydroxymethyl)-4-(4-(3,4,5-trifluorophenyl)-1H-1,2,3-triazol-1-yl)tetrahydro-2H-pyran-3,5-diol | 0.89 | 540.01 | 0.40 |

Example 2.31.102

(2S,3R,4S,5R,6R)-2-((2-Hydroxy-2-methyl-1-(o-tolyl)propyl)thio)-6-(hydroxymethyl)-4-(4-(3,4,5-trifluorophenyl)-1H-1,2,3-triazol-1-yl)tetrahydro-2H-pyran-3,5-diol 1. (2R,3R,4S,5R,6S)-2-(Acetoxymethyl)-6-((2-hydroxy-2-methyl-1-(o-tolyl)propyl)thio)-4-(4-(3,4,5-trifluorophenyl)-1H-1,2,3-triazol-1-yl)tetrahydro-2H-pyran-3,5-diyl diacetate To a solution of Intermediate 3 (0.15 g, 0.27 mmol) in EA (3.0 mL) are added TBAB (0.022 g, 0.068 mmol, 0.25 eq), aq. 1M Na$_2$CO$_3$ (2.0 mL) and Intermediate 5 (0.161 g, 0.41 mmol, 1.5 eq). The reaction mixture is stirred at rt for 72 h, diluted with EA, followed by water and brine. The phases are separated and the aq. layer is extracted with EA (3×). The combined organic layer is dried over MgSO$_4$, filtered and solvent removed in vacuo to give a yellow oil. The crude material is purified by preparative HPLC/MS(I) to yield a colorless oil (0.066 g, 36%) as the title compound. LC-MS (A) $t_R$=1.08 min; [M+H]$^+$: 666.03.

2. ((2S,3R,4S,5R,6R)-2-((2-Hydroxy-2-methyl-1-(o-tolyl)propyl)thio)-6-(hydroxymethyl)-4-(4-(3,4,5-trifluorophenyl)-1H-1,2,3-triazol-1-yl)tetrahydro-2H-pyran-3,5-diol (2.31.102.)

(2R,3R,4S,5R,6S)-2-(Acetoxymethyl)-6-((2-hydroxy-2-methyl-1-(o-tolyl)propyl)thio)-4-(4-(3,4,5-trifluorophenyl)-1H-1,2,3-triazol-1-yl)tetrahydro-2H-pyran-3,5-diyl diacetate (0.066 g, 0.10 mmol) is dissolved in MeOH (2.0 mL), NaOMe (0.5M in MeOH, 0.60 mL, 0.29 mmol, 3.0 eq) is added. The reaction mixture is stirred at rt over 17 h, the solvent removed in vacuo and the residue dissolved in MeCN, before being purified by preparative HPLC/MS(I) to give the title compound as a white solid (0.024 g, 44%). LC-MS (A) $t_R$=0.86 min; [M+H]$^+$: 540.04.

Example 2.31.102R (2S,3R,4S,5R,6R)-2-(((R)-2-Hydroxy-2-methyl-1-(o-tolyl)propyl)thio)-6-(hydroxymethyl)-4-(4-(3,4,5-trifluorophenyl)-1H-1,2,3-triazol-1-yl)tetrahydro-2H-pyran-3,5-diol Separation of the epimers of Example 2.31.102. (0.02 g) by chiral preparative HPLC (III) yielded the title compound (0.09 g) as a white solid. Chiral analytical HPLC (J): $t_R$=1.8 min.

Example 2.31.102S (2S,3R,4S,5R,6R)-2-(((S)-2-Hydroxy-2-methyl-1-(o-tolyl)propyl)thio)-6-(hydroxymethyl)-4-(4-(3,4,5-trifluorophenyl)-1H-1,2,3-triazol-1-yl)tetrahydro-2H-pyran-3,5-diol Separation of the epimers of Example 2.31.102. (0.02 g) by chiral preparative HPLC (III) yielded the title compound (0.05 g) as a white solid. Chiral analytical HPLC (J): $t_R$=1.23 min.

Example 2.31.118R (2S,3R,4S,5R,6R)-2-(((R)-2-Hydroxy-2-methyl-1-(2-(trifluoromethyl)pyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol The title compound is prepared from Intermediate 3 and Intermediate 6R according to the procedures described for Example 2.31.102. (Step 1. and Step 2.) as a white solid (0.145 g). LC-MS (A) $t_R$=0.79 min; [M+H]$^+$: 595.05.

Example 2.31.118S (2S,3R,4S,5R,6R)-2-(((S)-2-Hydroxy-2-methyl-1-(2-(trifluoromethyl)pyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol The title compound is prepared from Intermediate 3 and Intermediate 6S according to the procedures described for Example 2.31.102. (Step 1. and Step 2.) as a white solid (0.135 g). LC-MS (A) $t_R$=0.8 min; [M+H]$^+$: 595.21.

Following examples are prepared starting from o-substituted benzyl bromides, the corresponding dimethyl or diethyl ketones and Intermediate 3, according to the procedures described for Example 2.31.102. LC-MS and Gal-3 inhibition data are listed in Table 3 below. The LC-MS conditions used were LC-MS (A). Chiral analytical HPLC (I) (conditions and retention time) and inhibition data of the epimers R and S of selected Examples are also listed.

TABLE 3

| Example | Name | $t_R$ [min] | [M + H]$^+$ | HPLC conditions | $t_R$ chiral [min] | IC$_{50}$ [uM] |
|---|---|---|---|---|---|---|
| 2.31.102. | (2S,3R,4S,5R,6R)-2-((2-Hydroxy-2-methyl-1-(o-tolyl)propyl)thio)-6-(hydroxymethyl)-4-(4-(3,4,5-trifluorophenyl)-1H-1,2,3-triazol-1-yl)tetrahydro-2H-pyran-3,5-diol | 0.86 | 540.04 | | | 0.17 |
| 2.31.102R. | (2S,3R,4S,5R,6R)-2-(((R)-2-Hydroxy-2-methyl-1-(o-tolyl)propyl)thio)-6-(hydroxymethyl)-4-(4-(3,4,5-trifluorophenyl)-1H-1,2,3-triazol-1-yl)tetrahydro-2H-pyran-3,5-diol | 0.85 | 540.02 | Chiralpak IB B: 35% EtOH 3 min run | 1.8 | 0.12 |
| 2.31.102S. | (2S,3R,4S,5R,6R)-2-(((S)-2-Hydroxy-2-methyl-1-(o-tolyl)propyl)thio)-6-(hydroxymethyl)-4-(4-(3,4,5-trifluorophenyl)-1H-1,2,3-triazol-1-yl)tetrahydro-2H-pyran-3,5-diol | 0.87 | 540.03 | Chiralpak IB B: 35% EtOH 3 min run | 1.23 | 4.43 |
| 2.31.100. | (2S,3R,4S,5R,6R)-2-((2-Hydroxy-2-methyl-1-phenylpropyl)thio)-6-(hydroxymethyl)-4-(4-(3,4,5-trifluorophenyl)-1H-1,2,3-triazol-1-yl)tetrahydro-2H-pyran-3,5-diol | 0.82 | 526.01 | | | 1.9 |
| 2.31.103. | (2S,3R,4S,5R,6R)-2-((1-(2-Ethylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.90 | 554.31 | | | 0.30 |
| 2.31.104. | (2S,3R,4S,5R,6R)-2-((2-Hydroxy-2-methyl-1-(2-propylphenyl) propyl)thio)-6-(hydroxymethyl)-4-(4-(3,4,5-trifluorophenyl)-1H-1,2,3-triazol-1-yl)tetrahydro-2H-pyran-3,5-diol | 0.93 | 568.03 | | | 0.17 |
| 2.31.105. | (2S,3R,4S,5R,6R)-2-((2-Hydroxy-1-(2-isopropylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.92 | 568.31 | | | 0.18 |
| 2.31.105R. | (2S,3R,4S,5R,6R)-2-(((R)-2-Hydroxy-1-(2-isopropylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.93 | 568.26 | Chiralpak IB B: 30% EtOH 5 min run | 1.74 | 0.06 |
| 2.31.105S. | (2S,3R,4S,5R,6R)-2-(((S)-2-Hydroxy-1-(2-isopropylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.94 | 568.27 | Chiralpak IB B: 30% EtOH 5 min run | 1.33 | 8.3 |
| 2.31.106. | (2S,3R,4S,5R,6R)-2-((1-(2-Cyclopropylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.90 | 566.34 | | | 0.20 |
| 2.31.106R. | (2S,3R,4S,5R,6R)-2-(((R)-1-(2-cyclopropylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.9 | 566.35 | Chiralpak IB B: 30% EtOH 5 min run | 2.3 | 0.14 |
| 2.31.106S. | (2S,3R,4S,5R,6R)-2-(((S)-1-(2-cyclopropylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.91 | 566.36 | Chiralpak IB B: 30% EtOH 5 min run | 1.46 | 15.9 |
| 2.31.107. | (2S,3R,4S,5R,6R)-2-((2-Hydroxy-1-(2-isobutylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.96 | 582.02 | | | 0.26 |
| 2.31.107R. | (2S,3R,4S,5R,6R)-2-(((R)-2-hydroxy-1-(2-isobutylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.96 | 582.01 | Chiralpak IB B: 30% EtOH 5 min run | 1.73 | 0.2 |
| 2.31.107S. | (2S,3R,4S,5R,6R)-2-(((S)-2-hydroxy-1-(2-isobutylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.98 | 582.03 | Chiralpak IB B: 30% EtOH 5 min run | 1.24 | 0.95 |
| 2.31.108. | (2S,3R,4S,5R,6R)-2-((2-Hydroxy-1-(2-(2-hydroxyethyl)phenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.78 | 570.19 | | | 0.38 |
| 2.31.108R. | (2S,3R,4S,5R,6R)-2-(((R)-2-Hydroxy-1-(2-(2-hydroxyethyl)phenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.79 | 570.17 | Chiralpak IB B: 20% MeOH, 0.1% DEA 5 min run | 3.89 | 0.27 |
| 2.31.108S. | (2S,3R,4S,5R,6R)-2-(((S)-2-Hydroxy-1-(2-(2-hydroxyethyl)phenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.8 | 570.17 | Chiralpak IB B: 20% MeOH 0.1% DEA 5 min run | 3.25 | 8.1 |

TABLE 3-continued

| Example | Name | $t_R$ [min] | $[M + H]^+$ | HPLC conditions | $t_R$ chiral [min] | IC$_{50}$ [uM] |
|---|---|---|---|---|---|---|
| 2.31.109. | (2S,3R,4S,5R,6R)-2-((2-Hydroxy-2-methyl-1-(2-pentylphenyl) propyl)thio)-6-(hydroxymethyl)-4-(4-(3,4,5-trifluorophenyl)-1H-1,2,3-triazol-1-yl)tetrahydro-2H-pyran-3,5-diol | 1.01 | 595.98 | | | 0.54 |
| 2.31.110. | (2S,3R,4S,5R,6R)-2-((1-([1,1'-Biphenyl]-2-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.96 | 602.07 | | | 0.18 |
| 2.31.110R. | (2S,3R,4S,5R,6R)-2-(((R)-1-([1,1'-Biphenyl]-2-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.96 | 601.93 | Chiralpak IB B: 35% EtOH 3 min run | 1.92 | 0.22 |
| 2.31.110S. | (2S,3R,4S,5R,6R)-2-(((S)-1-([1,1'-Biphenyl]-2-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.97 | 601.96 | Chiralpak IB B: 35% EtOH 3 min run | 1.25 | 4.9 |
| 2.31.111. | (2S,3R,4S,5R,6R)-2-((1-(2-Chlorophenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.86 | 560.02 | | | 0.41 |
| 2.31.111R. | (2S,3R,4S,5R,6R)-2-(((R)-1-(2-Chlorophenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.85 | 559.91 | Chiralpak IB B: 25% EtOH 3 min run | 3.36 | 0.38 |
| 2.31.111S. | (2S,3R,4S,5R,6R)-2-(((S)-1-(2-Chlorophenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.86 | 559.89 | Chiralpak IB B: 25% EtOH 3 min run | 2.13 | 4.3 |
| 2.31.112. | (2S,3R,4S,5R,6R)-2-((2-Hydroxy-2-methyl-1-(2-(trifluoromethyl)phenyl)propyl)thio)-6-(hydroxymethyl)-4-(4-(3,4,5-trifluorophenyl)-1H-1,2,3-triazol-1-yl)tetrahydro-2H-pyran-3,5-diol | 0.89 | 593.69 | | | 0.25 |
| 2.31.112R. | (2S,3R,4S,5R,6R)-2-(((R)-2-Hydroxy-2-methyl-1-(2-(trifluoromethyl)phenyl)propyl)thio)-6-(hydroxymethyl)-4-(4-(3,4,5-trifluorophenyl)-1H-1,2,3-triazol-1-yl)tetrahydro-2H-pyran-3,5-diol | 0.89 | 594.12 | Chiralpak IB B: 40% EtOH 5 min run | 1.52 | 0.29 |
| 2.31.112S. | (2S,3R,4S,5R,6R)-2-(((S)-2-Hydroxy-2-methyl-1-(2-(trifluoromethyl)phenyl)propyl)thio)-6-(hydroxymethyl)-4-(4-(3,4,5-trifluorophenyl)-1H-1,2,3-triazol-1-yl)tetrahydro-2H-pyran-3,5-diol | 0.89 | 594.11 | Chiralpak IB B: 40% EtOH 5 min run | 1.09 | 7.07 |
| 2.31.113. | (2S,3R,4S,5R,6R)-2-((1-(2,3-Dichlorophenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.90 | 593.64 | | | 0.46 |
| 2.31.114. | (2S,3R,4S,5R,6R)-2-((1-(3-Fluoro-2-methylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.87 | 557.99 | | | 0.13 |
| 2.31.114R. | (2S,3R,4S,5R,6R)-2-(((S)-1-(3-Fluoro-2-methylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.87 | 557.98 | Chiralpak IB B: 30% EtOH 5 min run | 1.94 | 0.18 |
| 2.31.114S. | (2S,3R,4S,5R,6R)-2-(((S)-1-(3-Fluoro-2-methylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.88 | 557.96 | Chiralpak IB B: 30% EtOH 5 min run | 1.34 | 5.4 |
| 2.31.115. | (2S,3R,4S,5R,6R)-2-((2-Hydroxy-2-methyl-1-(naphthalen-1-yl)propyl)thio)-6-(hydroxymethyl)-4-(4-(3,4,5-trifluorophenyl)-1H-1,2,3-triazol-1-yl)tetrahydro-2H-pyran-3,5-diol | 0.89 | 576.2 | | | 0.18 |
| 2.31.115R. | (2S,3R,4S,5R,6R)-2-(((R)-2-Hydroxy-2-methyl-1-(naphthalen-1-yl)propyl)thio)-6-(hydroxymethyl)-4-(4-(3,4,5-trifluorophenyl)-1H-1,2,3-triazol-1-yl)tetrahydro-2H-pyran-3,5-diol | 0.89 | 576.26 | Chiralpak IC B: 25% EtOH 5 min run | 2.42 | 0.17 |
| 2.31.115S. | (2S,3R,4S,5R,6R)-2-(((S)-2-Hydroxy-2-methyl-1-(naphthalen-1-yl)propyl)thio)-6-(hydroxymethyl)-4-(4-(3,4,5-trifluorophenyl)-1H-1,2,3-triazol-1-yl)tetrahydro-2H-pyran-3,5-diol | 0.91 | 576.25 | Chiralpak IC B: 25% EtOH 5 min run | 3.51 | 10.3 |
| 2.31.116. | (2S,3R,4S,5R,6R)-2-((2-Hydroxy-2-methyl-1-(2-methylpyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol | 0.62 | 540.96 | | | 0.30 |
| 2.31.117. | (2S,3R,4S,5R,6R)-2-((2-Hydroxy-2-methyl-1-(4-methylpyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol | 0.62 | 541.05 | | | 0.53 |

TABLE 3-continued

| Example | Name | $t_R$ [min] | [M + H]+ | HPLC conditions | $t_R$ chiral [min] | IC$_{50}$ [uM] |
|---|---|---|---|---|---|---|
| 2.31.118R.* | (2S,3R,4S,5R,6R)-2-(((R)-2-hydroxy-2-methyl-1-(2-(trifluoromethyl)pyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol | 0.79 | 595.05 | Chiralpak IB B: 30% iPrOH 5 min run | 2.53 | 0.21 |
| 2.31.118S.* | (2S,3R,4S,5R,6R)-2-(((S)-2-Hydroxy-2-methyl-1-(2-(trifluoromethyl)pyridin-3-yl)propyl)thio)-6-(hydroxymethyl)-4-(4-(3,4,5-trifluorophenyl)-1H-1,2,3-triazol-1-yl)tetrahydro-2H-pyran-3,5-diol | 0.8 | 595.21 | Chiralpak IB B: 30% iPrOH 5 min run | 2.19 | 6.21 |
| 2.31.119. | (2S,3R,4S,5R,6R)-2-((2-Hydroxy-2-methyl-1-(3,5,6-trimethylpyrazin-2-yl)propyl)thio)-6-(hydroxymethyl)-4-(4-(3,4,5-trifluorophenyl)-1H-1,2,3-triazol-1-yl)tetrahydro-2H-pyran-3,5-diol | 0.75 | 570.06 | | | 0.23 |
| 2.31.119R. | (2S,3R,4S,5R,6R)-2-(((R)-2-Hydroxy-2-methyl-1-(3,5,6-trimethylpyrazin-2-yl)propyl)thio)-6-(hydroxymethyl)-4-(4-(3,4,5-trifluorophenyl)-1H-1,2,3-triazol-1-yl)tetrahydro-2H-pyran-3,5-diol | 0.76 | 570.34 | Chiralpak IC B: 25% (1/1) MeCN/EtOH 5 min run | 3.57 | 0.27 |
| 2.31.119S. | (2S,3R,4S,5R,6R)-2-(((S)-2-Hydroxy-2-methyl-1-(3,5,6-trimethylpyrazin-2-yl)propyl)thio)-6-(hydroxymethyl)-4-(4-(3,4,5-trifluorophenyl)-1H-1,2,3-triazol-1-yl)tetrahydro-2H-pyran-3,5-diol | 0.75 | 570.35 | Chiralpak IC B: 25% (1/1) MeCN/EtOH 5 min run | 1.26 | 2.63 |
| 2.31.120. | (2S,3R,4S,5R,6R)-2-((2-Hydroxy-2-methyl-1-(4-methylisoxazol-3-yl)propyl)thio)-6-(hydroxymethyl)-4-(4-(3,4,5-trifluorophenyl)-1H-1,2,3-triazol-1-yl)tetrahydro-2H-pyran-3,5-diol | 0.75 | 530.98 | | | 0.73 |
| 2.31.120R. | (2S,3R,4S,5R,6R)-2-(((R)-2-Hydroxy-2-methyl-1-(4-methylisoxazol-3-yl)propyl)thio)-6-(hydroxymethyl)-4-(4-(3,4,5-trifluorophenyl)-1H-1,2,3-triazol-1-yl)tetrahydro-2H-pyran-3,5-diol | 0.75 | 531.00 | Chiralpak ID B: 35% 2-ProOH 5 min run | 2.76 | 0.32 |
| 2.31.120S. | (2S,3R,4S,5R,6R)-2-(((S)-2-Hydroxy-2-methyl-1-(4-methylisoxazol-3-yl)propyl)thio)-6-(hydroxymethyl)-4-(4-(3,4,5-trifluorophenyl)-1H-1,2,3-triazol-1-yl)tetrahydro-2H-pyran-3,5-diol | 0.76 | 531.01 | Chiralpak ID B: 35% 2-ProOH 5 min run | 1.67 | 12.4 |
| 2.31.121. | (2S,3R,4S,5R,6R)-2-((1-(3,5-Dimethylisoxazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.75 | 544.9 | | | 0.71 |
| 2.31.122. | (2S,3R,4S,5R,6R)-2-((1-(2,5-Dimethyloxazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.72 | 545.05 | | | 0.88 |
| 2.31.122R. | (2S,3R,4S,5R,6R)-2-(((R)-1-(2,5-Dimethyloxazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.73 | 545.09 | Chiralpak IB B: 30% EtOH 5 min run | 1.92 | 0.37 |
| 2.31.122S. | (2S,3R,4S,5R,6R)-2-(((S)-1-(2,5-dimethyloxazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.72 | 545.04 | Chiralpak IB B: 30% EtOH 5 min run | 1.27 | 4.12 |
| 2.31.123. | (2S,3R,4S,5R,6R)-2-((1-(2,5-Dimethylthiazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.71 | 562.02 | | | 0.55 |
| 2.31.123R. | (2S,3R,4S,5R,6R)-2-(((R)-1-(2,5-Dimethylthiazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.71 | 562.05 | Chiralcel OD-H B: 35% MeOH 0.1% DEA 5 min run | 2.34 | 0.28 |
| 2.31.123S. | (2S,3R,4S,5R,6R)-2-(((S)-1-(2,5-Dimethylthiazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol | 0.71 | 562.07 | Chiralcel OD-H B: 35% MeOH 0.1% DEA 5 min run | 1.24 | 4.7 |
| 2.31.124. | (2S,3R,4S,5R,6R)-2-((2-Hydroxy-2-methyl-1-(4-methylthiophen-3-yl)propyl)thio)-6-(hydroxymethyl)-4-(4-(3,4,5-trifluorophenyl)-1H-1,2,3-triazol-1-yl)tetrahydro-2H-pyran-3,5-diol | 0.84 | 545.67 | | | 0.50 |
| 2.32.120R.* | (2S,3R,4S,5R,6R)-2-(((R)-2-Ethyl-2-hydroxy-1-(3-methylisoxazol-4-yl)butyl)thio)-6-(hydroxymethyl)-4-(4-(3,4,5-trifluorophenyl)-1H-1,2,3-triazol-1-yl)tetrahydro-2H-pyran-3,5-diol | 0.84 | 559.24 | Chiralpak IC B: 25% (1/1) MeCN/EtOH 5 min run | 2.52 | 1.22 |

TABLE 3-continued

| Example | Name | $t_R$ [min] | $[M + H]^+$ | HPLC conditions | $t_R$ chiral [min] | $IC_{50}$ [uM] |
|---|---|---|---|---|---|---|
| 2.32.120S.* | (2S,3R,4S,5R,6R)-2-(((S)-2-Ethyl-2-hydroxy-1-(3-methylisoxazol-4-yl)butyl)thio)-6-(hydroxymethyl)-4-(4-(3,4,5-trifluorophenyl)-1H-1,2,3-triazol-1-yl)tetrahydro-2H-pyran-3,5-diol | 0.84 | 559.24 | Chiralpak IC B: 25% (1/1) MeCN/EtOH 5 min run | 3.23 | 11.3 |

*Epimers are obtained from the chiral separation of the corresponding thioquinoline intermediates in analogy to the procedures described for Example 2.31.118R. and Example 2.31.118S..

Following examples are prepared starting from 1-(bromomethyl)-2-(trifluoromethyl)benzene, the corresponding aldehyde and Intermediate 3, according to the procedures described for 2.31.102. LC-MS and Gal-3 inhibition data are listed in Table 4 below. The LC-MS conditions used were LC-MS (A).

TABLE 4

| Example | Name | $t_R$ [min] | $[M + H]^+$ | $IC_{50}$ [uM] |
|---|---|---|---|---|
| 2.60.112. | (2S,3R,4S,5R,6R)-2-((2-Hydroxy-1-(2-(trifluoromethyl)phenyl) butyl)thio)-6-(hydroxymethyl)-4-(4-(3,4,5-trifluorophenyl)-1H-1,2,3-triazol-1-yl)tetrahydro-2H-pyran-3,5-diol | 0.91 | 594.17 | 0.23 |
| 2.61.112. | (2S,3R,4S,5R,6R)-2-((2-Hydroxy-2-phenyl-1-(2-(trifluoromethyl)phenyl)ethyl)thio)-6-(hydroxymethyl)-4-(4-(3,4,5-trifluorophenyl)-1H-1,2,3-triazol-1-yl)tetrahydro-2H-pyran-3,5-diol | 0.95 | 642.00 | 1.1 |
| 2.62.112. | (2S,3R,4S,5R,6R)-2-((2-Hydroxy-2-(o-tolyl)-1-(2-(trifluoromethyl)phenyl)ethyl)thio)-6-(hydroxymethyl)-4-(4-(3,4,5-trifluorophenyl)-1H-1,2,3-triazol-1-yl)tetrahydro-2H-pyran-3,5-diol | 0.97 | 656.18 | 1.22 |

Example 2.33.112

(2S,3R,4S,5R,6R)-2-(((3,3-Difluoro-1-hydroxycyclobutyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol 1. 2-((2-(Trifluoromethyl)benzyl)thio)quinoline DBU (1.8 mL, 11.8 mmol, 1.0 eq) is added to a solution of 2-quinolinethiol (2.0 g, 11.8 mmol, 1.0 eq) in toluene (40.0 mL) at rt. The reaction mixture is stirred at rt for 30 min. 2-(Trifluoromethyl)benzyl bromide (2.8 g, 11.8 mmol) is added and the solution is stirred at rt for 48 h. The reaction mixture is concentrated under reduced pressure to give a yellow solid. Trituration from Hept yielded a solid, that is removed by filtration and the remaining Hept is concentrated in vacuo to give an orange solid as 2-((2-(trifluoromethyl)benzyl)thio)quinoline (3.61 g, 96%). LC-MS (A) $t_R$=1.16 min; $[M+H]^+$: 320.08.

2. 3,3-Difluoro-1-((quinolin-2-ylthio)(2-(trifluoromethyl)phenyl)methyl)cyclobutan-1-ol To a cooled (−78° C.) solution of 2-((2-(trifluoromethyl)benzyl)thio)quinoline (1.0 g, 3.1 mmol) in THF (30.0 mL) is added at −78° C. n-BuLi (1.6M in hexane, 4.7 mmol, 1.5 eq) and the reaction mixture is stirred at −78° C. for 60 min. 3,3-Difluoro-cyclobutanone (0.41 g, 3.7 mmol, 1.2 eq) in THF (15.0 mL) is added and the reaction mixture is allowed to warm to −50° C. for 2 h, then cooled down to −78° C. and n-BuLi (1.6 M in hexane, 3.0 mL, 4.68 mmol, 1.5 eq) is added again, followed by 3,3-difluoro-cyclobutanone (0.41 g, 3.76 mmol, 1.2 eq). The reaction mixture is allowed to warm to rt for 17 h, quenched with aq. sat. NH$_4$Cl, extracted with EA, the layers are separated and the aqueous layer is extracted with EA (3×). The combined organic layer is washed with brine, dried over MgSO$_4$, filtered and the solvent removed in vacuo to give a brown oil. The crude is purified by preparative HPLC-MS (I) to afford a brown solid as the title compound (0.23 g, 18%). LC-MS (A): $t_R$=1.12 min; $[M+H]^+$: 426.1.

3. 3,3-Difluoro-1-(mercapto(2-(trifluoromethyl)phenyl)methyl)cyclobutan-1-ol

To a solution of 3,3-difluoro-1-((quinolin-2-ylthio)(2-(trifluoromethyl)phenyl)methyl)cyclobutan-1-ol (0.24 g, 0.55 mmol, 1.0 eq) in glacial acetic acid (10.0 mL) is added sodium cyanoborohydride (0.22 g, 3.33 mmol, 6.0 eq) and stirring is continued at rt for 17 h. The reaction mixture is quenched by the addition of water (5.0 mL) and is left stirring at rt for 1 h, diluted with DCM, the layers are separated and the aqueous layer is extracted with DCM. The combined organic layer is washed with brine, dried over MgSO$_4$ and the solvent is removed in vacuo to give a yellow oil. The crude material is purified by Flash Master (Büchi, product added dry on isolute, 10 g column, 15 mL/min, 10 mL fractions, Hept/EA 100/0 to 1/1, Rf(Hept/EA 1/1)=0.38) to give 3,3-difluoro-1-(mercapto(2-(trifluoromethyl)phenyl)methyl)cyclobutan-1-ol as a yellow oil (0.13 g, 77%). LC-MS (A): $t_R$=0.97 min; $[M+H]^+$: no mass visible.

4. (2R,3R,4S,5R,6S)-2-(Acetoxymethyl)-6-(((3,3-difluoro-1-hydroxycyclobutyl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate To a solution of Intermediate 3 (0.20 g, 0.36 mmol) in EA (6.0 mL) is added 3,3-difluoro-1-(mercapto(2-(trifluoromethyl)phenyl)methyl)cyclobutan-1-ol (0.13 g, 0.43 mmol, 1.2 eq) and TBAB (0.03 g, 0.09 mmol, 0.25 eq), followed by aq 1M Na$_2$CO$_3$ (3.0 mL). The reaction mixture is stirred at rt over 72 h, then diluted with EA, followed by water and brine. The phases are separated and the aq. layer is extracted with EA (3×). The combined organic layer is dried over MgSO$_4$, filtered and the solvent is removed in vacuo to give a brown oil, that is purified by preparative HPLC/MS (I) to afford the title compound as a beige oil (0.27 g, 96%). LC-MS (A): t$_R$=1.12 min; [M+H]$^+$: 768.19.

5. (2S,3R,4S,5R,6R)-2-(((3,3-Difluoro-1-hydroxycyclobutyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol (2.33.112.)

(2R,3R,4S,5R,6S)-2-(Acetoxymethyl)-6-(((3,3-difluoro-1-hydroxycyclobutyl)(2-(trifluoromethyl)phenyl)methyl) thio)-4-(4-(3,4,5-trifluorophenyl)-1H-1,2,3-triazol-1-yl)tetrahydro-2H-pyran-3,5-diyl diacetate (0.27 g, 0.35 mmol, 1.0 eq) is dissolved in MeOH (4.0 mL) and K$_2$CO$_3$ (0.09 g, 0.07 mmol, 0.2 eq) is added at rt. The reaction mixture is stirred at rt for 48 h, then diluted with MeCN, followed by water and the mixture is directly purified by preparative HPLC/MS (I) to give the title compound as a white solid (0.12 g, 52%). LC-MS (A): t$_R$=0.94 min; [M+H]$^+$: 642.04.

Example 2.33.112R (2S,3R,4S,5R,6R)-2-(((R)-(3,3-Difluoro-1-hydroxycyclobutyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol[1,3-di-deoxy-1-((3,3-difluoro-1-hydroxy-cyclobutan-1-yl)-(2-(trifluoromethyl)phenyl)methyl-(R)-thio)-3-[4-(3,4,5-trifluorophenyl)-1H-1,2,3-triazol-1-yl]-β-D-galactopyranoside]

Separation of the epimers of Example 2.33.112. (0.116 g) by chiral preparative HPLC (IV) yielded the title compound (0.038 g) as a white solid. Chiral analytical HPLC (K): t$_R$=1.7 min.

Example 2.33.112S (2S,3R,4S,5R,6R)-2-(((S)-(3,3-Difluoro-1-hydroxycyclobutyl)(2-(trifluoromethylphenyl)methyl)thio)-6-(hydroxymethyl)-4-(4-(3,4,5-trifluorophenyl)-1H-1,2,3-triazol-1-yl)tetrahydro-2H-pyran-3,5-diol Separation of the epimers of Example 2.33.112. (0.116 g) by chiral preparative HPLC (IV) yielded the title compound (0.041 g) as a white solid. Chiral analytical HPLC (K): t$_R$=1.25 min.

Following examples are prepared starting from o-substituted benzyl bromides, the corresponding cyclic ketons and Intermediate 3 according to the procedures described for Example 2.33.112. LC-MS and Gal-3 inhibition data are listed in Table 5 below. The LC-MS conditions used were LC-MS (A). Chiral analytical HPLC (conditions and retention time) and inhibition data of the epimers R and S of selected Examples are also listed.

TABLE 5

| Example | Name | t$_R$ [min] | [M + H]$^+$ | HPLC conditions | t$_R$ chiral [min] | IC$_{50}$ [uM] |
|---|---|---|---|---|---|---|
| 2.33.112. | (2S,3R,4S,5R,6R)-2-(((3,3-Difluoro-1-hydroxycyclobutyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.94 | 642.04 | | | 0.25 |
| 2.33.112R. | (2S,3R,4S,5R,6R)-2-(((R)-(3,3-Difluoro-1-hydroxycyclobutyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.94 | 642.04 | Chiralpak IB B: 30% EtOH 2.5 min run | 1.69 | 0.14 |
| 2.33.112S. | (2S,3R,4S,5R,6R)-2-(((S)-(3,3-Difluoro-1-hydroxycyclobutyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.94 | 642.08 | Chiralpak IB B: 30% EtOH 2.5 min run | 1.24 | 11.3 |
| 2.34.102. | (2S,3R,4S,5R,6R)-2-(((1-Hydroxycyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.9 | 551.98 | | | 1.00 |
| 2.35.102. | (2S,3R,4S,5R,6R)-2-(((1-Hydroxy-3,3-dimethylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.96 | 579.99 | | | 0.35 |
| 2.36.102. | (2S,3R,4S,5R,6R)-2-(((1-Hydroxy-3-methylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.91 | 565.96 | | | 0.46 |
| 2.36.102R. | (2S,3R,4S,5R,6R)-2-(((1R)-(1-Hydroxy-3-methylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.91 | 565.99 | Chiralpak IB B: 30% EtOH 2.5 min run | 2.44 | 0.44 |

TABLE 5-continued

| Example | Name | $t_R$ [min] | [M + H]+ | HPLC conditions | $t_R$ chiral [min] | IC$_{50}$ [uM] |
|---|---|---|---|---|---|---|
| 2.36.102S. | (2S,3R,4S,5R,6R)-2-(((1S)-(1-Hydroxy-3-methylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.94 | 565.99 | Chiralpak IB B: 30% EtOH 2.5 min run | 1.44 | 7.2 |
| 2.37.102. | (2S,3R,4S,5R,6R)-2-(((1-Hydroxy-2,3-dimethylcyclobutyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.96 | 580 | | | 0.56 |
| 2.38.102. | (2S,3R,4S,5R,6R)-2-(((1-Hydroxycyclopentyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.92 | 565.97 | | | 0.18 |
| 2.38.102R. | (2S,3R,4S,5R,6R)-2-(((R)-(1-Hydroxycyclopentyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.90 | 566.02 | Chiralpak IB B: 30% EtOH 4 min run | 2.18 | 0.11 |
| 2.38.102S. | (2S,3R,4S,5R,6R)-2-(((S)-(1-Hydroxycyclopentyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.92 | 566.1 | Chiralpak IB B: 30% EtOH 4 min run | 1.65 | 2.75 |
| 2.39.128. | (2S,3R,4S,5R,6R)-2-(((5-Cyclopropyl-3-methylisoxazol-4-yl)(1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.89 | 611.2 | | | 0.21 |
| 2.39.128R. | (2S,3R,4S,5R,6R)-2-(((R)-(5-Cyclopropyl-3-methylisoxazol-4-yl)(1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.88 | 611.2 | Chiralcel OJ-H B: 15% (1/1) MeCN/EtOH 3 min run | 1.41 | 0.19 |
| 2.39.128S. | (2S,3R,4S,5R,6R)-2-(((S)-(5-Cyclopropyl-3-methylisoxazol-4-yl)(1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.88 | 611.2 | Chiralcel OJ-H B: 15% (1/1) MeCN/EtOH 3 min run | 1.28 | 3.21 |
| 2.39.102. | (2S,3R,4S,5R,6R)-2-(((1-Hydroxycyclohexyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.96 | 579.99 | | | 0.09 |
| 2.39.102R. | (2S,3R,4S,5R,6R)-2-(((R)-(1-Hydroxycyclohexyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.95 | 580.01 | Chiralpak IB B: 30% EtOH 3 min run | 2.18 | 0.09 |
| 2.39.102S. | (2S,3R,4S,5R,6R)-2-(((S)-(1-Hydroxycyclohexyl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.97 | 579.99 | Chiralpak IB B: 30% EtOH 3 min run | 1.74 | 4.54 |
| 2.40.102. | (2S,3R,4S,5R,6R)-2-(((4-Hydroxy-1-methylpiperidin-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.69 | 594.92 | | | 0.09 |
| 2.41.102. | (2R,3R,4S,5R,6S)-2-(Hydroxymethyl)-6-((4-hydroxytetrahydro-2H-pyran-4-yl)(o-tolyl)methyl)thio)-4-(4-(3,4,5-trifluorophenyl)-1H-1,2,3-triazol-1-yl)tetrahydro-2H-pyran-3,5-diol | 0.81 | 581.99 | | | 0.09 |
| 2.41.102R. | (2R,3R,4S,5R,6S)-2-(Hydroxymethyl)-6-(((R)-4-hydroxytetrahydro-2H-pyran-4-yl)(o-tolyl)methyl)thio)-4-(4-(3,4,5-trifluorophenyl)-1H-1,2,3-triazol-1-yl)tetrahydro-2H-pyran-3,5-diol | 0.81 | 582.07 | Chiralpak IF B: 35% 2-ProOH 5 min run | 2.42 | 0.04 |
| 2.41.102S. | (2R,3R,4S,5R,6S)-2-(Hydroxymethyl)-6-(((S)-4-hydroxytetrahydro-2H-pyran-4-yl)(o-tolyl)methyl)thio)-4-(4-(3,4,5-trifluorophenyl)-1H-1,2,3-triazol-1-yl)tetrahydro-2H-pyran-3,5-diol | 0.83 | 582.09 | Chiralpak IF B: 35% 2-ProOH 5 min run | 1.61 | 7.36 |
| 2.42.102. | (2S,3R,4S,5R,6R)-2-(((4-Hydroxy-2,2,6,6-tetramethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.95 | 638.13 | | | 0.38 |
| 2.42.102R. | (2S,3R,4S,5R,6R)-2-(((R)-(4-Hydroxy-2,2,6,6-tetramethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.93 | 638.16 | Chiralpak IA B: 3% EtOH 5 min run | 1.91 | 0.09 |

TABLE 5-continued

| Example | Name | $t_R$ [min] | $[M + H]^+$ | HPLC conditions | $t_R$ chiral [min] | $IC_{50}$ [uM] |
|---|---|---|---|---|---|---|
| 2.42.102S. | (2S,3R,4S,5R,6R)-2-(((S)-(4-Hydroxy-2,2,6,6-tetramethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.95 | 638.16 | Chiralpak IA B: 3% EtOH 5 min run | 1.53 | 7.82 |
| 2.43.102. | (2S,3R,4S,5R,6R)-2-(((4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.89 | 610.12 | | | 0.12 |
| 2.43.102RS. | (2S,3R,4S,5R,6R)-2-(((R)-((S)-4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.87 | 609.93 | Chiralpak AD-H B: 30% 2-ProOH 5 min run | 2.39 | 0.04 |
| 2.43.102RR. | (2S,3R,4S,5R,6R)-2-(((R)-((R)-4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.86 | 609.92 | Chiralpak AD-H B: 30% 2-ProOH 5 min run | 3.36 | 0.29 |
| 2.43.102SS. | (2S,3R,4S,5R,6R)-2-(((S)-((S)-4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.89 | 609.94 | Chiralpak AD-H B: 30% 2-ProOH 5 min run | 1.85 | 3.92 |
| 2.43.102SR. | (2S,3R,4S,5R,6R)-2-(((S)-(R)-4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.88 | 609.87 | Chiralpak AD-H B: 30% 2-ProOH 5 min run | 1.16 | 3.9 |
| 2.43.112RS. | (2S,3R,4S,5R,6R)-2-(((R)-((S)-4-Hydroxy-2,2-dimethyltetrahydro-2H-pyran-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.91 | 664.13 | Chiralpak IA B: 30% (1/1) MeCN/EtOH 5 min run | 1.21 | 0.13 |
| 2.43.112RR. | (2S,3R,4S,5R,6R)-2-(((R)-((R)-4-Hydroxy-2,2-dimethyltetrahydro-2H-pyran-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.89 | 664.05 | Chiralcel OJ-H B: 20% (1/1) MeCN/EtOH 5 min run | 1.14 | 1.5 |
| 2.43.112SR. | (2S,3R,4S,5R,6R)-2-(((S)-((R)-4-Hydroxy-2,2-dimethyltetrahydro-2H-pyran-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.92 | 664.13 | Chiralpak IA B: 30% (1/1) MeCN/EtOH 5 min run | 3.3 | 4.9 |
| 2.43.112SS. | (2S,3R,4S,5R,6R)-2-(((S)-((S)-4-Hydroxy-2,2-dimethyltetrahydro-2H-pyran-4-yl)(o-tolyl)methyl)thio)-6-(hydroxymethyl)-4-(4-(3,4,5-trifluorophenyl)-1H-1,2,3-triazol-1-yl)tetrahydro-2H-pyran-3,5-diol | 0.9 | 664.05 | Chiralcel OJ-H B: 20% (1/1) MeCN/EtOH 5 min run | 1.95 | 7.3 |
| 2.35.125. | (2S,3R,4S,5R,6R)-2-(((3,3-Difluoro-1-hydroxycyclobutyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.96 | 635.15 | | | 0.32 |
| 2.35.125R. | (2S,3R,4S,5R,6R)-2-(((R)-(3,3-Difluoro-1-hydroxycyclobutyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.96 | 635.15 | Chiralpak ID B: 40% EtOH 5 min run | 1.03 | 0.1 |
| 2.35.125S. | (2S,3R,4S,5R,6R)-2-(((S)-(3,3-Difluoro-1-hydroxycyclobutyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.95 | 635.18 | Chiralpak ID B: 40% EtOH 5 min run | 1.39 | 3.0 |
| 2.39.125R.* | (2S,3R,4S,5R,6R)-2-(((R)-(1-Hydroxycyclohexyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.94 | 635.33 | Chiralpak ID B: 40% MeOH 5 min run | 1.14 | 0.1 |
| 2.39.125S.* | (2S,3R,4S,5R,6R)-2-(((S)-(1-Hydroxycyclohexyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.93 | 635.32 | Chiralpak ID B: 40% MeOH 5 min run | 1.84 | 3.0 |

TABLE 5-continued

| Example | Name | t_R [min] | [M + H]+ | HPLC conditions | t_R chiral [min] | IC_50 [uM] |
|---|---|---|---|---|---|---|
| 2.39.119R.* | (2S,3R,4S,5R,6R)-2-(((R)-(1-Hydroxycyclohexyl) (3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.86 | 610.28 | Chiralpak IB B: 35% MeOH 5 min run | 1.74 | 0.07 |
| 2.39.119S.* | (2S,3R,4S,5R,6R)-2-(((S)-(1-Hydroxycyclohexyl) (3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.85 | 610.28 | Chiralpak IB B: 35% MeOH 5 min run | 1.3 | 3.96 |
| 2.39.120R.* | (2S,3R,4S,5R,6R)-2-(((R)-(1-Hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol | 0.85 | 571.16 | Chiralpak IC B: 30% MeOH 5 min run | 2.23 | 0.2 |
| 2.39.120S.* | (2S,3R,4S,5R,6R)-2-(((S)-(1-Hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol | | | Chiralpak IC B: 30% MeOH 5 min run | 2.75 | 14.8 |
| 2.44.120R.* | (2S,3R,4S,5R,6R)-2-(((R)-(4,4-Difluoro-1-hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol | 0.86 | 607.32 | Chiralpak AD-H B: 40% MeOH 5 min run | 1.68 | 0.11 |
| 2.44.120S.* | (2S,3R,4S,5R,6R)-2-(((S)-(4,4-Difluoro-1-hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol | 0.86 | 607.32 | Chiralpak AD-H B: 40% MeOH 5 min run | 1.02 | 8.27 |
| 2.44.105. | (2S,3R,4S,5R,6R)-2-(((4,4-Difluoro-1-hydroxycyclohexyl)(2-isopropylphenyl)methyl)thio)-6-(hydroxymethyl)-4-(4-(3,4,5-trifluorophenyl)-1H-1,2,3-triazol-1-yl)tetrahydro-2H-pyran-3,5-diol [1,3-di-deoxy-1-((4,4-difluoro-1-hydroxy-cyclohexan-1-yl)-(2-(-isopropyl)phenyl)methyl-thio)-3-[4-(3,4,5-trifluorophenyl)-1H-1,2,3-triazol-1-yl]-β-D-galactopyranoside] | 1.01 | 644.3 | | | 0.14 |
| 2.44.105R. | (2S,3R,4S,5R,6R)-2-(((R)-(4,4-Difluoro-1-hydroxycyclohexyl)(2-isopropylphenyl)methyl)thio)-6-(hydroxymethyl)-4-(4-(3,4,5-trifluorophenyl)-1H-1,2,3-triazol-1-yl)tetrahydro-2H-pyran-3,5-diol [1,3-di-deoxy-1-((4,4-difluoro-1-hydroxy-cyclohexan-1-yl)-(2-(-isopropyl)phenyl)methyl-(R)-thio)-3-[4-(3,4,5-trifluorophenyl)-1H-1,2,3-triazol-1-yl]-β-D-galactopyranoside] | 1.00 | 644.2 | Chiralpak AD-H B: 35% EtOH 5 min run | 1.73 | 0.06 |
| 2.44.105S. | (2S,3R,4S,5R,6R)-2-(((S)-(4,4-Difluoro-1-hydroxycyclohexyl)(2-isopropylphenyl)methyl)thio)-6-(hydroxymethyl)-4-(4-(3,4,5-trifluorophenyl)-1H-1,2,3-triazol-1-yl)tetrahydro-2H-pyran-3,5-diol | 1.01 | 644.21 | Chiralpak AD-H B: 35% EtOH 5 min run | 1.1 | 0.95 |
| 2.44.119R.* | (2S,3R,4S,5R,6R)-2-(((R)-(4,4-Difluoro-1-hydroxycyclohexyl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.88 | 646.19 | Chiralpak ID B: 25% MeOH 4 min run | 1.5 | 0.03 |
| 2.44.119S.* | (2S,3R,4S,5R,6R)-2-(((S)-(4,4-Difluoro-1-hydroxycyclohexyl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.87 | 646.2 | Chiralpak ID B: 25% MeOH 4 min run | 1.86 | 0.7 |
| 2.44.125R.* | (2S,3R,4S,5R,6R)-2-(((R)-(4,4-Difluoro-1-hydroxycyclohexyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.94 | 671.18 | Chiralpak ID B: 30% (1/1) (MeCN/MeOH) 3.5 min run | 1.18 | 0.05 |
| 2.44.125S.* | (2S,3R,4S,5R,6R)-2-(((S)-(4,4-Difluoro-1-hydroxycyclohexyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.94 | 671.18 | Chiralpak ID B: 30% (1/1) (MeCN/MeOH) 3.5 min run | 1.64 | 0.82 |
| 2.44.111R* | (2S,3R,4S,5R,6R)-2-(((R)-(2-Chlorophenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.94 | 636.17 | Chiralpak IB B: 25% EtOH 3.5 min run | 2.42 | 0.09 |
| 2.44.111S * | (2S,3R,4S,5R,6R)-2-(((S)-(2-Chlorophenyl)(4,4-difluoro-1-hydroxycyclohexyl)methyl)thio)-6-(hydroxymethyl)- | 0.96 | 636.15 | Chiralpak IB B: 25% EtOH | 2.17 | 18.4 |

TABLE 5-continued

| Example | Name | t_R [min] | [M + H]+ | HPLC conditions | t_R chiral [min] | IC_50 [uM] |
|---|---|---|---|---|---|---|
| | (hydroxymethyl)-4-(4-(3,4,5-trifluorophenyl)-1H-1,2,3-triazol-1-yl)tetrahydro-2H-pyran-3,5-diol | | | 3.5 min run | | |
| 2.44.112. | (2S,3R,4S,5R,6R)-2-(((4,4-Difluoro-1-hydroxycyclohexyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.97 | 670.12 | | | 0.3 |
| 2.44.112R. | (2S,3R,4S,5R,6R)-2-(((R)-(4,4-Difluoro-1-hydroxycyclohexyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.97 | 670.12 | Chiralpak IG B: 35% MeCN/EtOH/DEA (50:50:0.1) 5 min run | 1.33 | 0.08 |
| 2.44.112S. | (2S,3R,4S,5R,6R)-2-(((S)-(4,4-Difluoro-1-hydroxycyclohexyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | | | Chiralpak IG B: 35% MeCN/EtOH/DEA (50:50:0.1) 5 min run | 2.06 | 19.5 |
| 2.44.113. | (2S,3R,4S,5R,6R)-2-(((2,3-Dichlorophenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 670.07 | 0.98 | | | 0.36 |
| 2.44.113R. | (2S,3R,4S,5R,6R)-2-(((R)-(2,3-Dichlorophenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 670.04 | 0.97 | Chiralpak AY-H B: 30% MeCN/2-PrOH/DEA 50:50:0.1 5 min run | 1.23 | 0.80 |
| 2.44.113S. | (2S,3R,4S,5R,6R)-2-(((S)-(2,3-Dichlorophenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 670.05 | 0.98 | Chiralpak AY-H B: 30% MeCN/2-PrOH/DEA 50:50:0.1 5 min run | 1.30 | 57.5 |
| 2.44.106R.* | (2S,3R,4S,5R,6R)-2-(((R)-(2-Cyclopropylphenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 641.87 | 0.97 | Chiralpak IA B: 30% (1/1) MeCN/EtOH 5 min run | 3.04 | 0.06 |
| 2.44.106S.* | (2S,3R,4S,5R,6R)-2-(((S)-(2-Cyclopropylphenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 641.88 | 0.98 | Chiralpak IA B: 30% (1/1) MeCN/EtOH 5 min run | 2.18 | 0.93 |
| 2.41.112. | (2R,3R,4S,5R,6S)-2-(Hydroxymethyl)-6-(((4-hydroxytetrahydro-2H-pyran-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol | 0.85 | 636.08 | | | 0.11 |
| 2.41.112R. | (2R,3R,4S,5R,6S)-2-(Hydroxymethyl)-6-(((R)-(4-hydroxytetrahydro-2H-pyran-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol | 0.85 | 636.09 | Chiralpak IG B: 35% 2-ProOH 5 min run | 1.57 | 0.08 |
| 2.41.112S. | (2R,3R,4S,5R,6S)-2-(Hydroxymethyl)-6-(((S)-(4-hydroxytetrahydro-2H-pyran-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol | 0.86 | 636.08 | Chiralpak IG B: 35% 2-ProOH 5 min run | 2.63 | 6 |
| 2.41.125. | (2R,3R,4S,5R,6S)-2-(Hydroxymethyl)-6-(((4-hydroxytetrahydro-2H-pyran-4-yl)(3-(trifluoromethyl)pyridin-2-yl)methyl)thio)-4-(4-(3,4,5-trifluorophenyl)-1H-1,2,3-triazol-1-yl)tetrahydro-2H-pyran-3,5-diol | 0.82 | 636.95 | | | 0.25 |
| 2.41.125R. | (2R,3R,4S,5R,6S)-2-(Hydroxymethyl)-6-(((R)-(4-hydroxytetrahydro-2H-pyran-4-yl)(3-(trifluoromethyl)pyridin-2-yl)methyl)thio)-4-(4-(3,4,5-trifluorophenyl)-1H-1,2,3-triazol-1-yl)tetrahydro-2H-pyran-3,5-diol | 0.83 | 636.97 | Chiralpak IF B: 35% (1/1) MeCN/EtOH 4 min run | 1.55 | 0.03 |
| 2.41.125S. | (2R,3R,4S,5R,6S)-2-(Hydroxymethyl)-6-(((S)-(4-hydroxytetrahydro-2H-pyran-4-yl)(3-(trifluoromethyl)pyridin-2-yl)methyl)thio)-4-(4-(3,4,5-trifluorophenyl)-1H-1,2,3-triazol-1-yl)tetrahydro-2H-pyran-3,5-diol | 0.81 | 636.95 | Chiralpak IF B: 35% (1/1) MeCN/EtOH 4 min run | 2.48 | 1.83 |
| 2.41.119. | (2R,3R,4S,5R,6S)-2-(Hydroxymethyl)-6-(((4-hydroxytetrahydro-2H-pyran-4-yl)(3,5,6-trimethylpyrazin-2-yl)methyl)thio)-4-(4-(3,4,5- | 0.74 | 611.90 | | | 0.16 |

TABLE 5-continued

| Example | Name | $t_R$ [min] | $[M + H]^+$ | HPLC conditions | $t_R$ chiral [min] | $IC_{50}$ [uM] |
|---|---|---|---|---|---|---|
| | trifluorophenyl)-1H-1,2,3-triazol-1-yl)tetrahydro-2H-pyran-3,5-diol | | | | | |
| 2.41.119R. | (2R,3R,4S,5R,6S)-2-(Hydroxymethyl)-6-(((R)-(4-hydroxytetrahydro-2H-pyran-4-yl)(3,5,6-trimethylpyrazin-2-yl)methyl)thio)-4-(4-(3,4,5-trifluorophenyl)-1H-1,2,3-triazol-1-yl)tetrahydro-2H-pyran-3,5-diol | 0.75 | 612.13 | Chiralpak IC B: 35% (1/1) MeCN/EtOH 4 min run | 1.72 | 0.06 |
| 2.41.119S. | (2R,3R,4S,5R,6S)-2-(Hydroxymethyl)-6-(((S)-(4-hydroxytetrahydro-2H-pyran-4-yl)(3,5,6-trimethylpyrazin-2-yl)methyl)thio)-4-(4-(3,4,5-trifluorophenyl)-1H-1,2,3-triazol-1-yl)tetrahydro-2H-pyran-3,5-diol | 0.74 | 612.13 | Chiralpak IC B: 35% (1/1) MeCN/EtOH 4 min run | 2.49 | 2.99 |
| 2.40.112. | (2S,3R,4S,5R,6R)-2-(((4-Hydroxy-1-methylpiperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.71 | 649.11 | | | 0.13 |
| 2.40.112R. | (2S,3R,4S,5R,6R)-2-(((R)-(4-Hydroxy-1-methylpiperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.72 | 648.99 | Chiralpak ID B: 30% (1/1/0.1) (DCM/MeOH/DEA) 5 min run | 2.17 | 0.06 |
| 2.40.112S. | (2S,3R,4S,5R,6R)-2-(((S)-(4-Hydroxy-1-methylpiperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.70 | 649.02 | Chiralpak ID B: 30% (1/1/0.1) (DCM/MeOH/DEA) 5 min run | 2.87 | 3.95 |
| 2.40.125. | (2S,3R,4S,5R,6R)-2-(((4-Hydroxy-1-methylpiperidin-4-yl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.65 | 649.96 | | | 0.2 |
| 2.40.125R. | (2S,3R,4S,5R,6R)-2-(((R)-(4-Hydroxy-1-methylpiperidin-4-yl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.67 | 650.32 | Chiralpak IB B: 35% EtOH, 0.1% DEA 5 min run | 2.61 | 0.02 |
| 2.40.125S. | (2S,3R,4S,5R,6R)-2-(((S)-(4-Hydroxy-1-methylpiperidin-4-yl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.65 | 650.32 | Chiralpak IB B: 35% EtOH, 0.1% DEA 5 min run | 1.94 | 3.65 |

*Epimers are obtained from the chiral separation of the corresponding thioquinoline intermediates according to the procedures described for Example 2.31.118R. and Example 2.31.118S..

Example 2.40.119

(2S,3R,4S,5R,6R)-2-(((4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol[1,3-dideoxy-1-((1-methyl-4-hydroxy-piperidin-4-yl)-(3,5,6-trimethylpyrazin-2-yl)methyl-thio)-3-[4-(3,4,5-trifluorophenyl)-1H-1,2,3-triazol-1-yl]-β-D-galactopyranoside]

Example 2.40.119 is synthesized from Intermediate 3 and Intermediate 5.

1. (2R,3R,4S,5R,6S)-2-(Acetoxymethyl)-6-(((4-hydroxy-1-methylpiperidin-4-yl)(3,5,6-trimethylpyrazin-2-yl)methyl)thio)-4-(4-(3,4,5-trifluorophenyl)-1H-1,2,3-triazol-1-yl)tetrahydro-2H-pyran-3,5-diyl diacetate To a solution of Intermediate 3 (0.80 g, 1.45 mmol) in EA (20.0 mL) are added Intermediate 5 (0.480 g, 1.71 mmol, 1.17 eq), TBAB (0.12 g, 0.36 mmol, 0.25 eq) and aq. 1M Na$_2$CO$_3$ (10.0 mL) at rt. The reaction mixture is stirred at rt for 48 h, diluted with EA, followed by water, then brine. The phases are separated and the aq. layer is extracted with EA (3×). The combined organic layer is dried over MgSO$_4$, filtered and solvent removed in vacuo to give a beige solid, that is purified by preparative HPLC/MS(I) to give the title compound as a white solid (0.33 g, 30%). LC-MS (A): $t_R$=0.82 min; $[M+H]^+$: 751.27.

2. (2S,3R,4S,5R,6R)-2-(((4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol (2.40.119.)

K$_2$CO$_3$ (0.012 g, 0.09 mmol, 0.2 eq) is added to a solution of (2R,3R,4S,5R,6S)-2-(acetoxymethyl)-6-(((4-hydroxy-1-methylpiperidin-4-yl)(3,5,6-trimethylpyrazin-2-yl)methyl)thio)-4-(4-(3,4,5-trifluorophenyl)-1H-1,2,3-triazol-1-yl)tetrahydro-2H-pyran-3,5-diyl diacetate (0.33 g, 0.44 mmol) in MeOH (3.0 mL) at rt. The reaction mixture is stirred at rt for 1 h, quenched by the addition of MeCN and water and the mixture is directly purified by preparative HPLC/MS(I) to yield the title compound as a white solid (0.21 g, 75%). LC-MS (A): $t_R$=0.63 min; $[M+H]^+$: 625.06. $^1$H NMR (400

MHz, MeOD) δ: 8.53 (s, 1H), 7.65 (dd, $J_1$=7.6 Hz, $J_2$=7.6 Hz, 2H), 4.79 (dd, $J_1$=2.8 Hz, $J_2$=10.7 Hz, 1H), 4.55 (s, 1H), 4.47 (d, J=9.4 Hz, 1H), 4.24 (t, J=10.0 Hz, 1H), 4.11 (d, J=2.6 Hz, 1H), 3.68 (m, 3H), 2.71 (d, J=11.5 Hz, 1H), 2.64 (s, 3H), 2.57-2.61 (m, 1H), 2.53 (s, 6H), 2.38-2.46 (m, 2H), 2.30 (s, 3H), 2.25 (bd, J=13.8 Hz, 1H), 1.85-1.94 (m, 1H), 1.71-1.81 (m, 1H), 1.45 (dd, $J_1$=1.5 Hz, $J_2$=13.7 Hz, 1H).

Example 2.40.119R (2S,3R,4S,5R,6R)-2-(((R)-(4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol[1,3-di-deoxy-1-((1-methyl-4-hydroxy-piperidin-4-yl)-(3,5,6-trimethylpyrazin-2-yl)methyl-(R)-thio)-3-[4-(3,4,5-trifluorophenyl)-1H-1,2,3-triazol-1-yl]-β-D-galactopyranoside]

Separation of the epimers of Example 2.40.119. (0.017 g) by chiral preparative HPLC (V) yielded the title compound (0.006 g) as a white solid. Chiral analytical HPLC (L): $t_R$=1.7 min.

Example 2.40.119S (2S,3R,4S,5R,6R)-2-(((S)-(4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol[1,3-di-deoxy-1-((1-methyl-4-hydroxy-piperidin-4-yl)-(3,5,6-trimethylpyrazin-2-yl)methyl-(S)-thio)-3-[4-(3,4,5-trifluorophenyl)-1H-1,2,3-triazol-1-yl]-β-D-galactopyranoside]

Separation of the epimers of Example 2.40.119. (0.017 g) by chiral preparative HPLC (V) yielded the title compound (0.006 g) as a white solid. Chiral analytical HPLC (L): $t_R$=2.4 min.

Following examples are prepared starting from o-substituted bromomethyl heteroaryls, the corresponding cyclic ketons and Intermediate 3 according to the procedures described for Example 2.40.119. LC-MS and Gal-3 inhibition data are listed in Table 6 below. The LC-MS conditions used were LC-MS (A). Chiral analytical HPLC (I) (conditions and retention time) and inhibition data of the epimers R and S of selected Examples are also listed.

TABLE 6

| Example | Name | $t_R$ [min] | [M + H]⁺ | HPLC conditions | $t_R$ chiral [min] | IC₅₀ [uM] |
|---|---|---|---|---|---|---|
| 2.40.119. | (2S,3R,4S,5R,6R)-2-(((4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.65 | 625.07 | | | 0.10 |
| 2.40.119R. | (2S,3R,4S,5R,6R)-2-(((R)-(4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.64 | 625.07 | Chiralpak IB B: 25% MeOH, 0.1% DEA 5 min run | 2.41 | 0.05 |
| 2.40.119S. | (2S,3R,4S,5R,6R)-2-(((S)-(4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.63 | 625.06 | Chiralpak IB B: 25% MeOH, 0.1% DEA 5 min run | 1.9 | 3.04 |
| 2.38.125. | (2S,3R,4S,5R,6R)-2-(((1-Hydroxycyclopentyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.89 | 621.15 | | | 0.13 |
| 2.38.125R. | (2S,3R,4S,5R,6R)-2-(((R)-(1-Hydroxycyclopentyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.91 | 621.16 | Chiralpak IC B: 25% MeOH 5 min run | 2.4 | 0.08 |
| 2.38.125S. | (2S,3R,4S,5R,6R)-2-(((S)-(1-Hydroxycyclopentyl)(3-(trifluoromethyl)pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.90 | 621.17 | Chiralpak IC B: 25% MeOH 5 min run | 1.2 | 5.62 |
| 2.44.126. | (2S,3R,4S,5R,6R)-2-(((4,4-Difluoro-1-hydroxycyclohexyl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.71 | 617.18 | | | 0.06 |
| 2.44.126R. | (2S,3R,4S,5R,6R)-2-(((R)-(4,4-Difluoro-1-hydroxycyclohexyl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.72 | 617.19 | Chiralcel OJ-H B: 20% (1/1) MeCN/EtOH 5 min run | 1.97 | 0.04 |
| 2.44.126S. | (2S,3R,4S,5R,6R)-2-(((S)-(4,4-Difluoro-1-hydroxycyclohexyl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.72 | 617.21 | Chiralcel OJ-H B: 20% (1/1) MeCN/EtOH 5 min run | 1.42 | 3.35 |
| 2.44.129. | (2S,3R,4S,5R,6R)-2-(((4,4-Difluoro-1-hydroxycyclohexyl)(3-methylpyrazin-2- | 0.83 | 618.19 | | | 0.09 |

TABLE 6-continued

| Example | Name | t_R [min] | [M + H]+ | HPLC conditions | t_R chiral [min] | IC_50 [uM] |
|---|---|---|---|---|---|---|
|  | yl)methyl)thio)-6-(hydroxymethyl)-4-(4-(3,4,5-trifluorophenyl)-1H-1,2,3-triazol-1-yl)tetrahydro-2H-pyran-3,5-diol |  |  |  |  |  |
| 2.44.129R. | (2S,3R,4S,5R,6R)-2-(((R)-(4,4-Difluoro-1-hydroxycyclohexyl)(3-methylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.83 | 618.16 | Chiracel OJ-H B: 18% EtOH 3.5 min run | 2.23 | 0.03 |
| 2.44.129S. | (2S,3R,4S,5R,6R)-2-(((S)-(4,4-Difluoro-1-hydroxycyclohexyl)(3-methylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.83 | 618.16 | Chiracel OJ-H B: 18% EtOH 3.5 min run | 1.53 | 1.48 |
| 2.44.130. | (2S,3R,4S,5R,6R)-2-(((5-Cyclopropyl-4-ethylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.96 | 661.19 |  |  | 0.06 |
| 2.44.130R. | (2S,3R,4S,5R,6R)-2-(((R)-(5-Cyclopropyl-4-ethylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.96 | 661.19 | Chiracel OJ-H B: 15% (1/1) MeCN/MeOH 5 min run | 2.91 | 0.02 |
| 2.44.130S. | (2S,3R,4S,5R,6R)-2-(((S)-(5-Cyclopropyl-4-ethylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.96 | 661.19 | Chiracel OJ-H B: 15% (1/1) MeCN/MeOH 5 min run | 1.92 | 1.85 |
| 2.44.131. | (2S,3R,4S,5R,6R)-2-(((5-Cyclopropyl-4-isobutylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 1.02 | 690.11 |  |  | 0.11 |
| 2.44.131 R. | (2S,3R,4S,5R,6R)-2-(((R)-(5-Cyclopropyl-4-isobutylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 1.01 | 689 | Chiracel OJ-H B: 15% MeOH 5 min run | 1.98 | 0.05 |
| 2.44.131S. | (2S,3R,4S,5R,6R)-2-(((S)-(5-Cyclopropyl-4-isobutylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 1.02 | 688.99 | Chiracel OJ-H B: 15% MeOH 5 min run | 1.35 | 9.74 |
| 2.44.132. | (2S,3R,4S,5R,6R)-2-(((4,4-Difluoro-1-hydroxycyclohexyl)(3-isopropylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.77 | 645.21 |  |  | 0.1 |
| 2.44.132R. | (2S,3R,4S,5R,6R)-2-(((R)-(4,4-Difluoro-1-hydroxycyclohexyl)(3-isopropylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.77 | 645.21 | Chiracel OD-H B: 30% (1/1) MeCN/EtOH 5 min run | 1.85 | 0.05 |
| 2.44.132S. | (2S,3R,4S,5R,6R)-2-(((S)-(4,4-Difluoro-1-hydroxycyclohexyl)(3-isopropylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol | 0.78 | 645.21 | Chiracel OD-H B: 30% (1/1) MeCN/EtOH 1:1 5 min run | 1.29 | 2.27 |
| 2.44.133. | (2S,3R,4S,5R,6R)-2-(((3-Chloropyrazin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.85 | 638.14 |  |  | 0.04 |
| 2.44.133R. | (2S,3R,4S,5R,6R)-2-(((R)-(3-Chloropyrazin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.86 | 638.14 | Regis (R,R) Whelk-O1 B: 25% (1/1) MeCN/EtOH 5 min run | 2.2 | 0.02 |
| 2.44.133S. | (2S,3R,4S,5R,6R)-2-(((S)-(3-Chloropyrazin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.86 | 638.15 | Regis (R,R) Whelk-O1 B: 25% (1/1) MeCN/EtOH 1:1 5 min run | 1.79 | 1.83 |
| 2.44.134. | (2S,3R,4S,5R,6R)-2-(((3-Cyclopropylpyridin-2-yl)(4,4-difluoro-1-hydroxycyclohexyl)methyl)thio)- | 0.75 | 643.21 |  |  | 0.07 |

TABLE 6-continued

| Example | Name | $t_R$ [min] | $[M + H]^+$ | HPLC conditions | $t_R$ chiral [min] | $IC_{50}$ [uM] |
|---|---|---|---|---|---|---|
| 2.44.134R. | 6-(hydroxymethyl)-4-(4-(3,4,5-trifluorophenyl)-1H-1,2,3-triazol-1-yl)tetrahydro-2H-pyran-3,5-diol (2S,3R,4S,5R,6R)-2-(((R)-(3-Cyclopropylpyridin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.75 | 643.21 | Chiralpak ID B: 20% (1/1) MeCN/EtOH 5 min run | 2.85 | 0.01 |
| 2.44.134S. | (2S,3R,4S,5R,6R)-2-(((S)-(3-Cyclopropylpyridin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol | 0.74 | 643.3 | Chiralpak ID B: 20% (1/1) MeCN/EtOH 5 min run | 3.55 | 0.7 |
| 2.44.135. | (2S,3R,4S,5R,6R)-2-(((4,4-Difluoro-1-hydroxycyclohexyl)(4-methylpyridazin-3-yl)methyl)thio)-6-(hydroxymethyl)-4-(4-(3,4,5-trifluorophenyl)-1H-1,2,3-triazol-1-yl)tetrahydro-2H-pyran-3,5-diol | 0.77 | 618.21 | | | 0.07 |
| 2.44.135R. | (2S,3R,4S,5R,6R)-2-(((R)-(4,4-Difluoro-1-hydroxycyclohexyl)(4-methylpyridazin-3-yl)methyl)thio)-6-(hydroxymethyl)-4-(4-(3,4,5-trifluorophenyl)-1H-1,2,3-triazol-1-yl)tetrahydro-2H-pyran-3,5-diol | 0.79 | 618.2 | Chiralpak ID B: 35% (1/1) MeCN/EtOH 5 min run | 1.63 | 0.04 |
| 2.44.135S. | (2S,3R,4S,5R,6R)-2-(((S)-(4,4-Difluoro-1-hydroxycyclohexyl)(4-methylpyridazin-3-yl)methyl)thio)-6-(hydroxymethyl)-4-(4-(3,4,5-trifluorophenyl)-1H-1,2,3-triazol-1-yl)tetrahydro-2H-pyran-3,5-diol | 0.77 | 618.22 | Chiralpak ID B: 35% (1/1) MeCN/EtOH 5 min run | 1.19 | 2.79 |
| 2.66.120. | 4-((((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(4-methylisoxazol-3-yl)methyl)-4-hydroxytetrahydro-2H-thiopyran 1,1-dioxide | 0.72 | 621.08 | | | 0.14 |
| 2.66.120R. | 4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(4-methylisoxazol-3-yl)methyl)-4-hydroxytetrahydro-2H-thiopyran 1,1-dioxide | 0.72 | 621.12 | Chiracel OJ-H B: 20% EtOH 5 min run | 1.23 | 0.03 |
| 2.66.120S. | 4-((S)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(4-methylisoxazol-3-yl)methyl)-4-hydroxytetrahydro-2H-thiopyran 1,1-dioxide | 0.73 | 621.11 | Chiracel OJ-H B: 20% EtOH 5 min run | 2.17 | 4.57 |
| 2.66.126R. | 4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(3-methylpyridin-2-yl)methyl)-4-hydroxytetrahydro-2H-thiopyran 1,1-dioxide | 0.63 | 631.14 | Chiracel OJ-H B: 20% EtOH 5 min run | 1.26 | 0.02 |
| 2.66.126S. | 4-((S)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(3-methylpyridin-2-yl)methyl)-4-hydroxytetrahydro-2H-thiopyran 1,1-dioxide | 0.62 | 631.16 | Chiracel OJ-H B: 20% EtOH 5 min run | 1.99 | 2.0 |
| 2.41.126. | (2R,3R,4S,5R,6S)-2-(Hydroxymethyl)-6-(((4-hydroxytetrahydro-2H-pyran-4-yl)(3-methylpyridin-2-yl)methyl)thio)-4-(4-(3,4,5-trifluorophenyl)-1H-1,2,3-triazol-1-yl)tetrahydro-2H-pyran-3,5-diol | 0.6 | 583.2 | | | 0.08 |
| 2.41.126R. | (2R,3R,4S,5R,6S)-2-(Hydroxymethyl)-6-(((R)-(4-hydroxytetrahydro-2H-pyran-4-yl)(3-methylpyridin-2-yl)methyl)thio)-4-(4-(3,4,5-trifluorophenyl)-1H-1,2,3-triazol-1-yl)tetrahydro-2H-pyran-3,5-diol | 0.61 | 583.19 | Chiralpak IC B: 50% (1/1) MeCN/EtOH 5 min run | 1.2 | 0.03 |
| 2.41.126S. | (2R,3R,4S,5R,6S)-2-(Hydroxymethyl)-6-(((S)-(4-hydroxytetrahydro-2H-pyran-4-yl)(3-methylpyridin-2-yl)methyl)thio)-4-(4-(3,4,5-trifluorophenyl)-1H-1,2,3-triazol-1-yl)tetrahydro-2H-pyran-3,5-diol | 0.6 | 583.2 | Chiralpak IC B: 50% (1/1) MeCN/EtOH 5 min run | 1.66 | 2.25 |

Example 2.45.112

(2R,3R,4S,5R,6S)-2-(Hydroxymethyl)-6-(((4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol Intermediate 8 (0.023 g, 0.03 mmol) is dissolved in MeOH (1.0 mL) and K$_2$CO$_3$ (0.004 g, 0.03 mmol, 1.0 eq) is added. The reaction mixture is stirred at rt for 17 h. The crude material is directly purified by preparative HPLC/MS (I) to yield the title product as a white solid (0.003 g, 17%). LC-MS (A): t$_R$=0.69 min; [M+H]$^+$: 635.3.

Example 2.46.112

(2S,3R,4S,5R,6R)-2-(((4-Hydroxy-1-(methylsulfonyl)piperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol 1. (2R,3R,4S,5R,6S)-2-(Acetoxymethyl)-6-(((4-hydroxy-1-(N-methylsulfamoyl)piperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate Methylsulfamoyl chloride (0.007, 0.06 mmol, 1.0 eq) and DIPEA (0.03 mL, 0.17 mmol, 3.0 eq) are added to a solution of Intermediate 8 (0.044 g, 0.06 mmol) in DCM (2.0 mL) at rt. The reaction mixture is stirred at rt for 48 h, partitioned between DCM and water, the layers are separated, the aqueous layer is extracted with DCM (3×). The combined organic layer is dried over MgSO$_4$, filtered and solvent removed in vacuo to give a colorless oil. The crude material is purified by preparative HPLC/MS(I) to give the title compound as a white solid (0.007 g, 14%). LC-MS (A): t$_R$=1.05 min; [M+H]$^+$: 853.98.

2. 4-(((((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxy-N-methylpiperidine-1-sulfonamide (2.46.112.)

To a solution of (2R,3R,4S,5R,6S)-2-(acetoxymethyl)-6-(((4-hydroxy-1-(N-methylsulfamoyl)piperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diyl diacetate (0.007 g, 0.008 mmol) in MeOH (1.0 mL) is added K$_2$CO$_3$ (0.002 g, 0.0002 mmol, 0.2 eq) at rt. The reaction mixture is stirred at rt for 17 h, diluted with MeCN, followed by water and the mixture is directly purified by preparative HPLC/MS(I). The title compound is obtained as a white solid (0.003 g, 52%). LC-MS (A): t$_R$=0.86 min; [M+H]$^+$: 727.94.

Example 2.47.112

(2S,3R,4S,5R,6R)-2-(((4-Hydroxy-1-(methylsulfonyl)piperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol Example 2.47.112. is synthesized from Intermediate 8 and methanesulfonyl chloride in analogy to Example 2.46.112. LC-MS (A): t$_R$=0.86 min; [M+H]$^+$: 712.9.

Example 2.47.112R (2S,3R,4S,5R,6R)-2-(((R)-(4-Hydroxy-1-(methylsulfonyl)piperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol[1,3-di-deoxy-1-((1-methylsulfonyl-4-hydroxy-piperidin-4-yl)-(2-(trifluoromethyl)phenyl)methyl-(R)-thio)-3-[4-(3,4,5-trifluorophenyl)-1H-1,2,3-triazol-1-yl]-β-D-galactopyranoside]

Example 2.47.112R. is synthesized from Intermediate 8R and methanesulfonyl chloride in analogy to Example 2.47.112. LC-MS (A): t$_R$=0.86 min; [M+H]$^+$: 713.19. $^1$H NMR (400 MHz, MeOD) δ: 8.49 (s, 1H), 8.17 (d, J=7.9 Hz, 1H), 7.70 (d, J=7.9 Hz, 1H), 7.64 (m, 3H), 7.46 (t, J=7.7 Hz, 1H), 4.71 (dd, J$_1$=3.0 Hz, J$_2$=10.5 Hz, 1H), 4.62 (s, 1H), 4.37 (d, J=9.5 Hz, 1H), 4.21 (t, J=10.3 Hz, 1H), 4.16 (d, J=2.8 Hz, 1H), 3.78-3.80 (m, 2H), 3.67 (t, J=6.3 Hz, 1H), 3.58-3.64 (m, 1H), 3.42-3.47 (m, 1H), 3.05 (td, J$_1$=2.5 Hz, J$_2$=12.5 Hz, 1H), 2.94 (td, J$_1$=2.3 Hz, J$_2$=12.0 Hz, 1H), 2.83 (s, 3H), 2.54 (dd, J$_1$=2.5 Hz, J$_2$=14.1 Hz, 1H), 1.2 (dd, J$_1$=2.4 Hz, J$_2$=13.7 Hz, 1H), 1.64-1.79 (m, 2H). Chiral analytical HPLC (L): t$_R$=1.7 min.

Example 2.48.112

1-(4-((((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidin-1-yl)ethan-1-one Example 2.48.112. is obtained as a side-product during the preparation of Example 2.47.112. LC-MS (A): t$_R$=0.84 min; [M+H]$^+$: 676.96.

Example 2.49.112R

N-Cyclopropyl-4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxamide Example 2.49.112R. is prepared from Intermediate 8R and isocyanato cyclopropane in analogy to Example 2.46.112. as a white powder. LC-MS (A): t$_R$=0.89 min; [M+H]$^+$: 693.23. LC-MS (A): t$_R$=0.84 min; [M+H]$^+$: 718.0. Chiral analytical HPLC (G): t$_R$=1.84 min. $^1$H NMR (400 MHz, MeOD) δ: 8.49 (s, 1H), 8.18 (d, J=8.0 Hz, 1H), 7.70-7.59 (m, 4H), 7.44 (t, J=7.7 Hz, 1H), 4.70 (dd, J$_1$=10.5 Hz, J$_2$=3.0 Hz, 1H), 4.58 (s, 1H), 4.34 (d, J=9.5 Hz, 1H), 4.2 (t, J=10.0 Hz, 1H), 4.15 (d, J=2.8 Hz, 1H), 3.92-3.85 (m, 1H), 3.78-3.75 (m, 1H), 3.74-3.68 (m, 1H), 3.65 (t, J=3.65

Hz, 1H), 3.08 (td, $J_1$=13.5 Hz, $J_2$=3.0 Hz, 1H), 2.96 (td, $J_1$=13.5 Hz, $J_2$=3.0 Hz, 1H), 2.53 (m, 1H), 2.38 (dd, $J_1$=13.6 Hz, $J_2$=2.2 Hz, 1H), 1.55 (m, 2H), 1.06 (dd, $J_1$=13.6 Hz, $J_2$=2.1 Hz, 1H), 0.65 (m, 2H), 0.44 (m, 2H).

Example 2.50.112R

Methyl 4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxylate Example 2.50.112. is prepared from Intermediate 8R and methyl chloroformate in analogy to Example 2.46.112. as a white powder. LC-MS (A): $t_R$=0.89 min; [M+H]$^+$: 693.23.

$^1$H NMR (400 MHz, MeOD) δ: 8.49 (s, 1H), 8.18 (d, J=8.0 Hz, 1H), 7.69 (d, J=8.0 Hz, 1H), 7.62-7.66 (m, 3H), 7.46 (t, J=7.7 Hz, 1H), 4.70 (dd, $J_1$=3.0 Hz, $J_2$=10.5 Hz, 1H), 4.58 (s, 1H), 4.34 (d, J=9.5 Hz, 1H), 4.20 (t, J=10.1 Hz, 1H), 4.15 (d, J=2.8 Hz, 1H), 4.01 (bd, J=13.3 Hz, 1H), 3.85 (bd, J=13.8 Hz, 1H), 3.75-3.80 (m, 2H), 3.69 (s, 3H), 3.65 (t, J=6.3 Hz, 1H), 2.92-3.23 (m, 2H), 2.43 (d, J=13.8 Hz, 1H), 1.47-1.62 (m, 2H), 1.08 (d, J=14.0 Hz, 1H).

Following examples are prepared starting from Intermediate 8, Intermediate 8R or Intermediate 8A in analogy to the procedures described above. LC-MS and Gal-3 inhibition data are listed in Table 7 below. The LC-MS conditions used were LC-MS (A). Chiral analytical HPLC (I) (conditions and retention time) and inhibition data of the epimers R and S of selected Examples are also listed.

TABLE 7

| Example | Name | $t_R$ [min] | [M + H]$^+$ | HPLC conditions | $t_R$ chiral [min] | IC$_{50}$ [uM] |
|---|---|---|---|---|---|---|
| 2.45.112. | (2R,3R,4S,5R,6S)-2-(Hydroxymethyl)-6-(((4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol | 0.69 | 635.3 | | | 0.13 |
| 2.46.112. | 4-((((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxy-N-methylpiperidine-1-sulfonamide | 0.86 | 727.94 | | | 0.05 |
| 2.47.112. | (2S,3R,4S,5R,6R)-2-(((4-Hydroxy-1-(methylsulfonyl)piperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.86 | 712.9 | | | 0.07 |
| 2.47.112R.* | (2S,3R,4S,5R,6R)-2-(((R)-(4-Hydroxy-1-(methylsulfonyl)piperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.86 | 713.19 | Chiralpak IB B: 25% EtOH 5 min run | 3.07 | 0.03 |
| 2.47.112S.* | (2S,3R,4S,5R,6R)-2-(((S)-(4-Hydroxy-1-(methylsulfonyl)piperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | 0.86 | 713.19 | Chiralpak IB B: 25% EtOH 5 min run | 2.62 | 2.82 |
| 2.48.112. | 1-(4-((((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidin-1-yl)ethan-1-one | 0.84 | 676.96 | | | 0.22 |
| 2.49.112R.* | N-Cyclopropyl-4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxamide | 0.84 | 718.0 | Chiralpak IE B: 45% (1/1) MeCN/EtOH 5 min run | 3.18 | 0.05 |
| 2.49.112S.* | N-Cyclopropyl-4-((S)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxamide | 0.84 | 718.0 | Chiralpak IE B: 45% (1/1) MeCN/EtOH 5 min run | 2.53 | 3.06 |
| 2.50.112R.* | Methyl 4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxylate | 0.89 | 693.23 | Chiralcel OD-H B: 30% MeOH 3 min run | 1.7 | 0.08 |
| 2.50.112S.* | Methyl 4-((S)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-4-hydroxypiperidine-1-carboxylate | 0.89 | 693.23 | Chiralcel OD-H B: 30% MeOH 3 min run | 2.2 | 7.7 |
| 2..57.112. | (2S,3R,4S,5R,6R)-2-(((3-Hydroxy-1-(methylsulfonyl)azetidin-3-yl)(2-(trifluoromethyl)phenyl)methyl)thio)-6-(Hydroxymethyl)-4-(4-(3,4,5-trifluorophenyl)-1H-1,2,3-triazol-1-yl)tetrahydro-2H-pyran-3,5-diol | 0.85 | 685.12 | | | 0.22 |

TABLE 7-continued

| Example | Name | $t_R$ [min] | [M + H]$^+$ | HPLC conditions | $t_R$ chiral [min] | IC$_{50}$ [uM] |
|---|---|---|---|---|---|---|
| 2..57.112R. | (2S,3R,4S,5R,6R)-2-(((R)-(3-Hydroxy-1-(methylsulfonyl)azetidin-3-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | | | Chiralpak IB B: 35% (1/1) MeCN/EtOH 5 min run | 1.6 | 0.17 |
| 2..57.112S. | (2S,3R,4S,5R,6R)-2-(((S)-(3-Hydroxy-1-(methylsulfonyl)azetidin-3-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol | | | Chiralpak IB B: 35% (1/1) MeCN/EtOH 5 min run | 1.21 | 5.8 |
| 2..58.112. | Methyl 3-((((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-3-hydroxyazetidine-1-carboxylate | 0.86 | 665.15 | | | 0.4 |
| 2..59.11.2 | N-Cyclopropyl-3-((((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)(2-(trifluoromethyl)phenyl)methyl)-3-hydroxyazetidine-1-carboxamide | 0.81 | 690.05 | | | 0.29 |

*Epimers are obtained from Intermediate 8R and Intermediate 8S.

Example 3.31.112

(2S,3R,4S,5R,6R)-4-(4-(3,5-Difluoro-4-methylphenyl)-1H-1,2,3-triazol-1-yl)-2-((2-hydroxy-2-methyl-1-(2-(trifluoromethyl)phenyl)propyl)thio)-6-(hydroxymethyl)tetrahydro-2H-pyran-3,5-diol 1. (2R,3R,4S,5R,6S)-2-(Acetoxymethyl)-4-(4-(3,5-difluoro-4-methylphenyl)-1H-1,2,3-triazol-1-yl)-6-((2-hydroxy-2-methyl-1-(2-(trifluoromethyl)phenyl)propyl)thio)tetrahydro-2H-pyran-3,5-diyl diacetate The triazole synthesis is conducted on a commercial continuous-flow reactor (Vapourtec) using a copper coil (10.0 mL internal volume) and a back-pressure regulator (6.0 bar). Intermediate 9 (0.062 g, 0.11 mmol) is dissolved in THF (2.0 mL), followed by the addition of the 5-ethynyl-1,3-difluoro-2-methylbenzene (4.41 mg, 0.11 mmol, 1 eq) and DIPEA (0.056 mL, 0.33 mmol, 3.0 eq). The mixture is pumped at a flow rate of 0.4 mL/min through the coil, which is kept at a temperature of 90° C. The reactor outlet is collected and concentrated under reduced pressure on a GeneVac EZ-2 Elite (40° C., 0 mbar, overnight) to obtain the crude, that is purified by preparative HPLC/MS (I) to give the title compound (0.033 g, 42%). LC-MS (A): $t_R$=1.1 min; [M+H]$^+$: 716.16.

2. (2S,3R,4S,5R,6R)-4-(4-(3,5-Difluoro-4-methylphenyl)-1H-1,2,3-triazol-1-yl)-2-(((R)-2-hydroxy-2-methyl-1-(2-(trifluoromethyl)phenyl)propyl)thio)-6-(hydroxymethyl)tetrahydro-2H-pyran-3,5-diol (3.31.112.)

(2R,3R,4S,5R,6S)-2-(Acetoxymethyl)-4-(4-(3,5-difluoro-4-methylphenyl)-1H-1,2,3-triazol-1-yl)-6-((2-hydroxy-2-methyl-1-(2-(trifluoromethyl)phenyl)propyl)thio)tetrahydro-2H-pyran-3,5-diyl diacetate (0.033 g, 0.0461 mmol) is dissolved in MeOH (2.0 mL) and K$_2$CO$_3$ (0.001 g, 0.009 mmol, 0.2 eq) is added at rt. The reaction mixture is stirred at rt for 2 h, quenched with MeCN, followed by water and the mixture is directly purified by preparative HPLC/MS(I) to yield a white solid (0.022 g, 82%) as the title compound. LC-MS (A): $t_R$=0.9 min; [M+H]$^+$: 590.24.

Example 3.31.112R (2S,3R,4S,5R,6R)-4-(4-(3,5-Difluoro-4-methylphenyl)-1H-1,2,3-triazol-1-yl)-2-(((R)-2-hydroxy-2-methyl-1-(2-(trifluoromethyl)phenyl)propyl)thio)-6-(hydroxymethyl)tetrahydro-2H-pyran-3,5-diol Separation of the epimers Example 3.31.112. (0.022 g) by chiral preparative HPLC (VI), followed by preparative HPLC/MS (I), yielded the title compound (0.006 g) as a white solid. Chiral analytical HPLC (M): $t_R$=1.67 min. $^1$H NMR (400 MHz, MeOD) δ: 8.45 (s, 1H), 8.20 (d, J=8.0 Hz, 1H), 7.68 (d, J=7.9 Hz, 1H), 7.62 (t, J=7.5 Hz, 1H), 7.39-7.46 (m, 3H), 4.7-4.66 (m, 2H), 4.18-4.27 (m, 2H), 4.15 (d, J=2.8 Hz, 1H), 3.77 (m, 2H), 3.63 (t, J=6.4 Hz, 1H), 2.22 (s, 3H), 1.52 (s, 3H), 1.09 (s, 3H).

Example 3.31.112S (2S,3R,4S,5R,6R)-4-(4-(3,5-Difluoro-4-methylphenyl)-1H-1,2,3-triazol-1-yl)-2-(((S)-2-hydroxy-2-methyl-1-(2-(trifluoromethyl)phenyl)propyl)thio)-6-(hydroxymethyl)tetrahydro-2H-pyran-3,5-diol Separation of the epimers Example 3.31.112. (0.022 g) by chiral preparative HPLC (VI), followed by preparative HPLC/MS (I), yielded the title compound (0.004 g) as a white solid. Chiral analytical HPLC (M): $t_R$=1.34 min.

Following examples are prepared starting from Intermediate 9 and the corresponding alkyne, in analogy to Example 3.31.112. LC-MS and Gal-3 inhibition data are listed in Table 8 below. The LC-MS conditions used were LC-MS (A). Chiral analytical HPLC (I) (conditions and retention time) and inhibition data of the epimers R and S of selected Examples are also listed.

TABLE 8

| Example | Name | $t_R$ [min] | $[M + H]^+$ | HPLC conditions | $t_R$ chiral [min] | $IC_{50}$ [uM] |
|---|---|---|---|---|---|---|
| 3.31.112. | (2S,3R,4S,5R,6R)-4-(4-(3,5-Difluoro-4-methylphenyl)-1H-1,2,3-triazol-1-yl)-2-((2-hydroxy-2-methyl-1-(2-(trifluoromethyl)phenyl)propyl)thio)-6-(hydroxymethyl)tetrahydro-2H-pyran-3,5-diol | 0.9 | 590.24 | | | 0.21 |
| 3.31.112R. | (2S,3R,4S,5R,6R)-4-(4-(3,5-Difluoro-4-methylphenyl)-1H-1,2,3-triazol-1-yl)-2-(((R)-2-hydroxy-2-methyl-1-(2-(trifluoromethyl)phenyl)propyl)thio)-6-(hydroxymethyl)tetrahydro-2H-pyran-3,5-diol | 0.9 | 590.28 | Chiralpak IB B: 30% MeOH, 0.1% DEA 5 min run | 1.67 | 0.15 |
| 3.31.112S. | (2S,3R,4S,5R,6R)-4-(4-(3,5-Difluoro-4-methylphenyl)-1H-1,2,3-triazol-1-yl)-2-(((S)-2-hydroxy-2-methyl-1-(2-(trifluoromethyl)phenyl)propyl)thio)-6-(hydroxymethyl)tetrahydro-2H-pyran-3,5-diol | 0.9 | 590.28 | Chiralpak IB B: 30% MeOH, 0.1% DEA 5 min run | 1.34 | 4.85 |
| 4.31.112 | (2S,3R,4S,5R,6R)-2-((2-Hydroxy-2-methyl-1-(2-(trifluoromethyl)phenyl)propyl)thio)-6-(hydroxymethyl)-4-(4-(naphthalen-2-yl)-1H-1,2,3-triazol-1-yl)tetrahydro-2H-pyran-3,5-diol | 0.89 | 590.27 | | | 2.24 |
| 5.31.112. | 4-(1-((2S,3R,4S,5R,6R)-3,5-Dihydroxy-2-((2-hydroxy-2-methyl-1-(2-(trifluoromethyl)phenyl)propyl)thio)-6-(hydroxymethyl)tetrahydro-2H-pyran-4-yl)-1H-1,2,3-triazol-4-yl)-2-fluorobenzonitrile | 0.85 | 583.24 | | | 1.5 |

Example 2.44.126R.I (2R,3R,4S,5R,6S)-6-(((R)-(4,4-Difluoro-1-hydroxycyclohexyl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol[1,3-di-deoxy-1-((4,4-difluoro-1-hydroxycyclohexan-1-yl)-(3-(-methyl)pyridin-2-yl)methyl-(R)-thio)-2-O-methyl-3-[4-(3,4,5-trifluorophenyl)-1H-1,2,3-triazol-1-yl]-b-D-galactopyranoside]

Example 2.44.126R.I. is synthesized from Example 2.44.126R. as described below.

1. (4aR,6S,7R,8R,8aR)-6-(((R)-(4,4-Difluoro-1-hydroxycyclohexyl)(3-methylpyridin-2-yl)methyl)thio)-2,2-dimethyl-8-(4-(3,4,5-trifluorophenyl)-1H-1,2,3-triazol-1-yl)hexahydropyrano[3,2-d][1,3]dioxin-7-ol A mixture of Example 2.44.126R. (0.26 g, 0.43 mmol), 2,2-dimethoxypropane (0.3 mL, 2.35 mmol, 5.5 eq), acetone (0.7 mL) and CSA (0.05 g, 0.21 mmol, 0.5 eq) in THF (4.0 mL) is heated at 60° C. for 6 h, then at rt for 15 h and again at 60° C. for 6 h. The reaction mixture is partitioned between EA and aq. sat. $NaHCO_3$, the layers are separated and the aqueous layer is extracted with EA (3×). The combined organic layer is washed with brine, dried over $MgSO_4$, filtered and the solvent removed in vacuo to give the title compound as a white solid (0.28 g, >99%), that is used without further purification. LC-MS (A): $t_R$=0.88 min; $[M+H]^+$: 657.92.

2. 4,4-Difluoro-1-((R)-(((4aR,6S,7R,8S,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)thio)(3-methylpyridin-2-yl)methyl)cyclohexan-1-ol To a stirred solution of (4aR,6S,7R,8R,8aR)-6-(((R)-(4,4-difluoro-1-hydroxycyclohexyl)(3-methylpyridin-2-yl)methyl)thio)-2,2-dimethyl-8-(4-(3,4,5-trifluorophenyl)-1H-1,2,3-triazol-1-yl)hexahydropyrano[3,2-d][1,3]dioxin-7-ol (0.26 g, 0.4 mmol) in DMF (3.0 mL) is added MeI (0.05 mL, 0.8 mmol, 2.0 eq), followed after 5 min by $CsCO_3$ (0.14 g, 0.4 mmol, 1.1 eq). The reaction mixture is stirred at rt for 48 h, partitioned between water and EA, the layers are separated and the aqueous layer is extracted with EA (3×). The combined organic layer is washed with brine, dried over $MgSO_4$, filtered and solvent removed in vacuo to give a yellow oil. Purification by preparative HPLC/MS (I) yielded the title compound as a white solid (0.20 g, 74%). LC-MS (A): $t_R$=0.95 min; $[M+H]^+$: 671.1.

3. (2R,3R,4S,5R,6S)-6-(((R)-(4,4-Difluoro-1-hydroxycyclohexyl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol (2.44.126R.I.)

To a mixture of 4,4-difluoro-1-((R)-(((4aR,6S,7R,8S,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)thio)(3-methylpyridin-2-yl)methyl)cyclohexan-1-ol (0.20 g, 0.3 mmol) in water (2.0 mL) is added AcOH (2.0 mL), the resulting solution is stirred at 60° C. for 8 h, then at rt for 24 h. The reaction mixture is cooled to 0° C., quenched with ($H_2O$/MeCN=1/1) (1.0 mL) and aq. $NH_4OH$ is added (until pH 5-6). The resulting solution is purified by preparative HPLC/MS(I) to give the title compound as a white solid (0.14 g, 76%). LC-MS (A): $t_R$=0.79 min; $[M+H]^+$: 631.1. $^1H$ NMR (400 MHz, MeOD) δ: 8.63 (s, 1H), 8.42 (d, J=4.0 Hz, 1H), 7.63-7.70 (m, 3H), 7.26 (dd, $J_1$=4.8 Hz, $J_2$=7.8 Hz, 1H), 4.85 (dd, $J_1$=2.9 Hz, $J_2$=10.5 Hz, 1H), 4.65 (s, 1H), 4.47 (d, J=9.5 Hz, 1H), 4.06 (d, J=2.9 Hz, 1H), 3.95 (t, J=9.9 Hz, 1H), 3.88-3.64 (m, 7H) 3.15 (s, 3H), 2.48 (s, 3H), 2.24 (m, 1H), 1.85 (m, 1H), 1.72 (m, 1H), 1.25-1.20 (m, 1H)

Following 2-OMe-Gal inhibitors are prepared from the corresponding 2-OH-Gal inhibitors as single epimers or as mixture of epimers according to the procedures described for Example 2.44.126R.I. LC-MS, Gal-3 inhibition data are listed in Table 9 below. The LC-MS conditions used were LC-MS (A). Chiral analytical HPLC (I) (conditions and retention time) and inhibition data of the epimers R and S of selected Examples are also listed.

TABLE 9

| Example | Name | $t_R$ | [M + H]$^+$ | HPLC conditions | $t_R$ chiral | IC$_{50}$ [uM] |
|---|---|---|---|---|---|---|
| 2.44.126R.I. | (2R,3R,4S,5R,6S)-6-(((R)-(4,4-Difluoro-1-hydroxycyclohexyl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.79 | 631.24 | ChiralCel OZ-H B: 40% (1/1) MeCN/EtOH 5 min run | 1.50 | 0.07 |
| 2.44.125R.I. | (2R,3R,4S,5R,6S)-6-(((R)-(4,4-Difluoro-1-hydroxycyclohexyl)(3-(trifluoromethyl)pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.02 | 685.05 | Chiralpak IB B: 20% MeCN/EtOH/DEA 1/1/0.1 5 min run | 1.89 | 0.06 |
| 2.39.125R.I. | (2R,3R,4S,5R,6S)-6-(((R)-(1-Hydroxycyclohexyl)(3-(trifluoromethyl)pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.03 | 649.07 | Chiralpak IB B: 25% MeCN/EtOH/DEA 1/1/0.1 5 min run | 2.35 | 0.09 |
| 2.44.137.I. | (2R,3R,4S,5R,6S)-6-(((3-Chloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.98 | 651.02 | | | 0.14 |
| 2.44.137R.I. | (2R,3R,4S,5R,6S)-6-(((R)-(3-Chloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.99 | 651.05 | Chiralpak IB B: 25% (1/1) MeCN/EtOH 5 min run | 2.4 | 0.07 |
| 2.43.112RS.I | (2R,3R,4S,5R,6S)-6-(((R)-((S)-4-Hydroxy-2,2-dimethyltetrahydro-2H-pyran-4-yl)(2-(trifluoromethyl)phenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.99 | 678.10 | Chiralpak IB B: 25% (1/1) MeCN/EtOH 5 min run | 1.45 | 0.14 |
| 2.66.126R.I. | 4-Hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(3-methylpyridin-2-yl)methyl)tetrahydro-2H-thiopyran 1,1-dioxide | 0.71 | 645.17 | Chiralpak IB B: 25% MeCN/EtOH/DEA 1/1/0.1 5 min run | 2.46 | 0.06 |
| 2.41.126R.I. | (2R,3R,4S,5R,6S)-2-(Hydroxymethyl)-6-(((R)-(4-hydroxytetrahydro-2H-pyran-4-yl)(3-methylpyridin-2-yl)methyl)thio)-5-methoxy-4-(4-(3,4,5-trifluorophenyl)-1H-1,2,3-triazol-1-yl)tetrahydro-2H-pyran-3-ol | 0.67 | 597.20 | Chiralpak IH B: 20% (1/1) MeCN/EtOH 5 min run | 2.4 | 0.06 |
| 2.43.102RS.I. | (2R,3R,4S,5R,6S)-6-(((R)-((S)-4-Hydroxy-2,2-dimethyltetrahydro-2H-pyran-4-yl)(o-tolyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.96 | 624.22 | Chiralpak IB B: 20% (1/1) MeCN/EtOH 5 min run | 2.40 | 0.06 |
| 2.44.132R.I. | (2R,3R,4S,5R,6S)-6-(((R)-(4,4-Difluoro-1-hydroxycyclohexyl)(3-isopropylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.85 | 659.24 | Chiralpak IB B: 20% MeCN/EtOH/DEA 1/1/0.1 5 min run | 1.85 | 0.12 |
| 2.44.134R.I. | (2R,3R,4S,5R,6S)-6-(((R)-(3-Cyclopropylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol- | 0.82 | 658.04 | Chiralcel OZH B: 35% MeCN/EtOH/DEA (1/1/0.1) 4 min run | 1.15 | 0.06 |

TABLE 9-continued

| Example | Name | $t_R$ | $[M + H]^+$ | HPLC conditions | $t_R$ chiral | $IC_{50}$ [uM] |
|---|---|---|---|---|---|---|
| | triazol-1-yl)tetrahydro-2H-pyran-3-ol [1,3-di-deoxy-1-((4,4-difluoro-1-hydroxy-cyclohexan-1-yl)-(3-(-cyclopropyl)pyridin-2-yl)methyl-(R)-thio)-2-O-methyl-3-[4-(3,4,5-trifluorophenyl)-1H-1,2,3-triazol-1-yl]-b-D-galactopyranoside] | | | | | |
| 2.44.135R.I. | (2R,3R,4S,5R,6S)-6-(((R)-(4,4-Difluoro-1-hydroxycyclohexyl)(4-methylpyridazin-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.89 | 632.39 | Chiralpak ID B: 35% (1/1) MeCN/EtOH 5 min run | 2.45 | 0.07 |
| 2.44.129R.I. | (2R,3R,4S,5R,6S)-6-(((R)-(4,4-Difluoro-1-hydroxycyclohexyl)(3-methylpyrazin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol [1,3-di-deoxy-1-((4,4-difluoro-1-hydroxy-cyclohexan-1-yl)-(3-(-methyl)pyrazin-2-yl)methyl-(R)-thio)-2-O-methyl-3-[4-(3,4,5-trifluorophenyl)-1H-1,2,3-triazol-1-yl]-b-D-galactopyranoside] | 0.93 | 632.16 | Chiralpak IG B: 35% (1/1) MeCN/MeOH 5 min run | 2.21 | 0.05 |

Example 2.39.120R.I (2R,3R,4S,5R,6S)-6-(((R)-(1-Hydroxycyclohexyl) (4-methylisoxazol-3-yl)methyl)thio)-2-(hydroxymethyl)-5-methoxy-4-(4-(3,4,5-trifluorophenyl)-1H-1, 2,3-triazol-1-yl)tetrahydro-2H-pyran-3-ol (2.39.120R.I.)

Example 2.39.120R.I. is synthesized from Example 2.39.120R. as described below.

1. (4aR,6S,7R,8R,8aR)-6-(((R)-(1-Hydroxycyclohexyl)(4-methylisoxazol-3-yl)methyl)thio)-2,2-dimethyl-8-(4-(3,4,5-trifluorophenyl)-1H-1,2,3-triazol-1-yl)hexahydropyrano[3,2-d][1,3]dioxin-7-ol A mixture of Example 2.39.120R. (0.14 g, 0.24 mmol), 2,2-dimethoxypropane (0.16 mL, 1.3 mmol, 5.5 eq), acetone (0.5 mL) and CSA (0.03 g, 0.12 mmol, 0.5 eq) in THF (1.5 mL) is heated at 50° C. for 2 h. The reaction mixture is partitioned between EA and sat.aq. NaHCO₃, the layers are separated and the aqueous layer is extracted with EA (3×). The combined organic layer is washed with brine, dried over MgSO₄, filtered and the solvent removed in vacuo to give a colorless oil, that is purified by preparative HPLC/MS (I) to give the title compound as a white solid (0.11 g, 76%). LC-MS (A): $t_R$=1.03 min; $[M+H]^+$: 611.22.

2. 1-((R)-(((4aR,6S,7R,8S,8aR)-7-Methoxy-2,2-dimethyl-8-(4-(3,4,5-trifluorophenyl)-1H-1,2,3-triazol-1-yl)hexahydropyrano[3,2-d][1,3]dioxin-6-yl) thio)(4-methylisoxazol-3-yl)methyl)cyclohexan-1-ol To a stirred solution of (4aR,6S,7R,8R,8aR)-6-(((R)-(1-hydroxycyclohexyl)(4-methylisoxazol-3-yl)methyl)thio)-2,2-dimethyl-8-(4-(3,4,5-trifluorophenyl)-1H-1,2,3-triazol-1-yl)hexahydropyrano[3,2-d][1,3]dioxin-7-ol (0.11 g, 0.18 mmol) in THF (2.0 mL) is added MeI (0.02 mL, 0.4 mmol, 2.0 eq) followed after 5 min by NaH (0.01 g, 0.2 mmol, 1.1 eq) and stirring is continued at rt for 2 h. The reaction mixture is partitioned between water and EA, the layers are separated and the aqueous layer is extracted with EA (3×). The combined organic layer is washed with brine, dried over MgSO₄, filtered and solvent removed in vacuo to give a brown oil. Purification by preparative HPLC/MS(I) gave the title compound as a white solid (0.07 g, 63%). LC-MS (A): $t_R$=1.10 min; $[M+H]^+$: 625.25

3. (2R,3R,4S,5R,6S)-6-(((R)-(1-Hydroxycyclohexyl) (4-methylisoxazol-3-yl)methyl)thio)-2-(hydroxymethyl)-5-methoxy-4-(4-(3,4,5-trifluorophenyl)-1H-1, 2,3-triazol-1-yl)tetrahydro-2H-pyran-3-ol (2.39.120R.I.)

To a mixture of 1-((R)-(((4aR,6S,7R,8S,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)thio)(4-methylisoxazol-3-yl)methyl)cyclohexan-1-ol (0.07 g, 0.11 mmol) in water (2.0 mL) is added AcOH (2.0 mL). The solution is stirred at 55° C. for 2.5 h, cooled (00), quenched with (H₂O/MeCN 1/1, 1.0 mL) and aq. NH₄OH is added (until pH 5-6) at 0° C. The resulting solution is purified by preparative HPLC/MS(I) to give the title compound as a white solid (0.05 g, 68%). ¹H NMR (400 MHz, MeOD) δ: 8.63 (s, 1H), 8.39 (s, 1H), 7.62-7.74 (m, 2H), 4.84 (dd, J=2.9 Hz, J=10.5 Hz, 1H), 4.52 (s, 1H), 4.32 (d, J=9.5 Hz, 1H), 4.09 (d, J=2.8 Hz, 1H), 4.01 (t, J=10.0 Hz, 1H), 3.83-3.68 (m, 2H), 3.64 (t, J=6.3 Hz, 1H), 3.23 (s, 3H), 2.21 (s, 3H), 1.87-2.03 (m, 1H), 1.5-1.8 (m, 8H), 1.28-1.38 (m, 1H). LC-MS (A): $t_R$=0.94 min; $[M+H]^+$: 585.23.

Example 2.39.120S.I (2R,3R,4S,5R,6S)-6-(((S)-(1-Hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol (2.39.120S.I.)

Example 2.39.120S.I. is synthesized from Example 2.39.120S. in analogy to Example 2.39.120R.I. as a white solid. LC-MS (A): $t_R$=0.95 min; [M+H]$^+$: 585.2.

Following 2-OMe-Gal inhibitors are prepared from the corresponding 2-OMe-Gal inhibitors according to the procedures described for Example 2.39.120R.I. LC-MS and Gal-3 inhibition data are listed in Table 10 below. The LC-MS conditions used were LC-MS (A). Chiral analytical HPLC (I) (conditions and retention time) and inhibition data of the epimers R and S of selected Examples are also listed.

TABLE 10

| Example | Name | $t_R$ | [M + H]$^+$ | HPLC conditions | $t_R$ chiral | IC$_{50}$ [uM] |
|---|---|---|---|---|---|---|
| 2.39.120R.I. | (2R,3R,4S,5R,6S)-6-(((R)-(1-Hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.94 | 585.23 | Chiralpak IA B: 30% (1/1) MeCN/EtOH 5 min run | 4.06 | 0.25 |
| 2.39.120S.I. | (2R,3R,4S,5R,6S)-6-(((S)-(1-Hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.95 | 585.2 | Chiralpak IA B: 30% (1/1) MECN/EtOH 5 min run | 2.52 | 12.5 |
| 2.44.105R.I. | (2R,3R,4S,5R,6S)-6-(((R)-(4,4-Difluoro-1-hydroxycyclohexyl)(2-isopropylphenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.08 | 657.99 | Chiralpak IF B: 15% (1/1) MeCN/EtOH 5 min run | 3.84 | 0.32 |
| 2.44.105S.I. | (2R,3R,4S,5R,6S)-6-(((S)-(4,4-Difluoro-1-hydroxycyclohexyl)(2-isopropylphenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.10 | 658 | Chiralpak IF B: 15% (1/1) MeCN/EtOH 5 min run | 3.28 | 70.5 |
| 2.44.120R.I. | (2R,3R,4S,5R,6S)-6-(((R)-(4,4-Difluoro-1-hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.95 | 621.11 | Chiralpak IB B: 25% (1/1) MeCN/EtOH 5 min run | 1.46 | 0.21 |
| 2.44.106R.I. | (2R,3R,4S,5R,6S)-6-(((R)-(2-Cyclopropylphenyl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.06 | 656.1 | Chiralpak IB B: 25% (1/1) MeCN/EtOH 5 min run | 1.58 | 0.18 |
| 2.44.136.I. | (2R,3R,4S,5R,6S)-6-(((4,4-Difluoro-1-hydroxycyclohexyl)(1,4-dimethyl-1H-pyrazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.92 | 634.11 | | | 0.42 |
| 2.44.136R.I. | (2R,3R,4S,5R,6S)-6-(((R)-(4,4-Difluoro-1-hydroxycyclohexyl)(1,4-dimethyl-1H-pyrazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.92 | 634.08 | Chiralpak IG B: 35% (1/1) MeCN/EtOH 5 min run | 2.56 | 0.26 |
| 2.44.136S.I. | (2R,3R,4S,5R,6S)-6-(((S)-(4,4-Difluoro-1-hydroxycyclohexyl)(1,4-dimethyl-1H-pyrazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.92 | 634.1 | Chiralpak IG B: 35% (1/1) MeCN/EtOH 5 min run | 1.23 | 15.6 |

TABLE 10-continued

| Example | Name | $t_R$ | $[M + H]^+$ | HPLC conditions | $t_R$ chiral | $IC_{50}$ [uM] |
|---|---|---|---|---|---|---|
| 2.44.138.I. | (2R,3R,4S,5R,6S)-6-(((4,4-Difluoro-1-hydroxycyclohexyl)(1-ethyl-4-methyl-1H-1,2,3-triazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.90 | 649.14 | | | 0.30 |
| 2.44.138R.I. | (2R,3R,4S,5R,6S)-6-(((R)-(4,4-Difluoro-1-hydroxycyclohexyl)(1-ethyl-4-methyl-1H-1,2,3-triazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.91 | 649.09 | Chiralpak IH B: 25% (1/1) MeCN/EtOH 5 min run | 2.05 | 0.15 |
| 2.44.138S.I. | (2R,3R,4S,5R,6S)-6-(((S)-(4,4-Difluoro-1-hydroxycyclohexyl)(1-ethyl-4-methyl-1H-1,2,3-triazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.90 | 649.10 | Chiralpak IH B: 25% (1/1) MeCN/EtOH 5 min run | 1.46 | 13.2 |
| 2.44.139.I. | (2R,3R,4S,5R,6S)-6-(((4-Chloro-1-ethyl-1H-pyrazol-5-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.99 | 668.02 | | | 0.62 |
| 2.44.139R.I. | (2R,3R,4S,5R,6S)-6-(((R)-(4-Chloro-1-ethyl-1H-pyrazol-5-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.98 | 668.04 | Chirakpak ID B: 20% (1/1) MeCN/2-ProOH 5 min run | 3.063 | 0.32 |
| 2.44.139S.I. | (2R,3R,4S,5R,6S)-6-(((S)-(4-Chloro-1-ethyl-1H-pyrazol-5-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.99 | 668.05 | Chiralpak ID B: 20% (1/1) MeCN/2-ProOH 1/1 5 min run | 2.1 | 37.9 |
| 2.44.140R.I. | (2R,3R,4S,5R,6S)-6-(((R)-(4,4-Difluoro-1-hydroxycyclohexyl)(5-ethyl-4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.00 | 649.11 | Chiralpak IB B: 25% (1/1) MeCN/EtOH 5 min run | 1.37 | 0.12 |
| 2.41.120R.I. | (2R,3R,4S,5R,6S)-2-(Hydroxymethyl)-6-(((R)-(4-hydroxytetrahydro-2H-pyran-4-yl)(4-methylisoxazol-3-yl)methyl)thio)-5-methoxy-4-(4-(3,4,5-trifluorophenyl)-1H-1,2,3-triazol-1-yl)tetrahydro-2H-pyran-3-ol | 0.82 | 587.12 | Chiralpak IB B: 25% (1/1) MeCN/EtOH 5 min run | 1.81 | 0.19 |
| 2.66.120R.I. | 4-Hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(4-methylisoxazol-3-yl)methyl)tetrahydro-2H-thiopyran 1,1-dioxide | 0.81 | 635.15 | Chiralpak IG B: 35% (1/1) MeCN/EtOH 5 min run | 2.23 | 0.07 |
| 2.39.128R.I. | (2R,3R,4S,5R,6S)-6-(((R)-(5-Cyclopropyl-3-methylisoxazol-4-yl)(1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.98 | 626.09 | Chiralpak IB B: 25% (1/1) MeCN/EtOH 5 min run | 1.78 | 0.30 |
| 2.44.130R.I. | (2R,3R,4S,5R,6S)-6-(((R)-(5-Cyclopropyl-4-ethylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol [1,3-dideoxy-1-((4,4-difluoro-1-hydroxy-cyclohexan-1-yl)-(5-(-cyclopropyl)-4-(-ethyl)isoxazol-3-yl)methyl-(R)-thio)-2-O-methyl-3-[4-(3,4,5-trifluorophenyl)-1H-1,2,3-triazol-1-yl]-b-D-galactopyranoside] | 1.03 | 675.22 | Chiralpak IB B: 20% (1/1) MeCN/EtOH 5 min run | 2.12 | 0.06 |

TABLE 10-continued

| Example | Name | $t_R$ | $[M + H]^+$ | HPLC conditions | $t_R$ chiral | $IC_{50}$ [uM] |
|---|---|---|---|---|---|---|
| 2.44.131R.I. | (2R,3R,4S,5R,6S)-6-(((R)-(5-Cyclopropyl-4-isobutylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.11 | 703.27 | Chiralpak IH B: 20% (1/1) MeCN/EtOH 5 min run | 1.83 | 0.13 |
| 2.44.133.I. | (2R,3R,4S,5R,6S)-6-(((3-Chloropyrazin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.94 | 652.13 | | | 0.17 |
| 2.44.133R.I. | (2R,3R,4S,5R,6S)-6-(((R)-(3-Chloropyrazin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol [1,3-di-deoxy-1-((4,4-difluoro-1-hydroxy-cyclohexan-1-yl)-(3-(-chloro)pyrazin-2-yl)methyl-(R)-thio)-2-O-methyl-3-[4-(3,4,5-trifluorophenyl)-1H-1,2,3-triazol-1-yl]-b-D-galactopyranoside] | 0.94 | 652.15 | REGIS (R,R) Whelk-O1 35% EtOH 2.5 min | 1.42 | 0.04 |
| 2.44.133S.I. | (2R,3R,4S,5R,6S)-6-(((S)-(3-Chloropyrazin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.93 | 652.17 | REGIS (R,R) Whelk-O1 35% EtOH 2.5 min | 1.77 | 2.71 |

Example 2.44.141.I (2R,3R,4S,5R,6S)-6-(((4-Chloro-3-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol Example 2.44.141.I. is prepared from 1-((4-chloro-3-methylpyridin-2-yl)(mercapto)methyl)-4,4-difluorocyclohexan-1-ol (prepared in analogy to Intermediate 7) and Intermediate 10 in analogy to Example 2.40.119. as a beige solid. LC-MS (A): $t_R$=0.98 min; [M+H]$^+$: 665.16.

Example 2.44.141R.I (2R,3R,4S,5R,6S)-6-(((R)-(4-Chloro-3-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol Separation of the epimers of Example 2.44.141.I. (0.026 g) by chiral preparative HPLC (VII) yielded the title compound (0.010 g) as a white solid. Chiral analytical HPLC (N): $t_R$=1.9 min LC-MS (A): $t_R$=0.98 min; [M+H]$^+$: 665.1.

Example 2.44.141 S.I (2R,3R,4S,5R,6S)-6-(((S)-(4-Chloro-3-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol Separation of the epimers of Example 2.44.141.I. (0.026 g) by chiral preparative HPLC (VII) yielded the title compound (0.008 g) as a white solid. Chiral analytical HPLC (N): $t_R$=2.98 min LC-MS (A): $t_R$=0.97 min; [M+H]$^+$: 665.11.

Following examples are prepared from Intermediate 10 and the corresponding mercapto alcohols (prepared in analogy to Intermediate 7) in analogy to Example 2.44.141.I. LC-MS and Gal-3 inhibition data are listed in Table 11 below. The LC-MS conditions used were LC-MS (A). Chiral analytical HPLC (I) (conditions and retention time) and inhibition data of the epimers R and S of selected Examples are also listed.

TABLE 11

| Example | Name | $t_R$ | $[M + H]^+$ | HPLC conditions | $t_R$ chiral | $IC_{50}$ [uM] |
|---|---|---|---|---|---|---|
| 2.44.141.I. | (2R,3R,4S,5R,6S)-6-(((4-Chloro-3-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.98 | 665.16 | | | 0.15 |
| 2.44.141R.I. | (2R,3R,4S,5R,6S)-6-(((R)-(4-Chloro-3-methylpyridin-2-yl)(4,4-difluoro-1-hydroxycyclohexyl)methyl)thio)-2- | 0.98 | 665.1 | ChiralCel OZ-H B: 30% (1/1) | 1.88 | 0.07 |

TABLE 11-continued

| Example | Name | $t_R$ | $[M + H]^+$ | HPLC conditions | $t_R$ chiral | $IC_{50}$ [uM] |
|---|---|---|---|---|---|---|
| | (hydroxymethyl)-5-methoxy-4-(4-(3,4,5-trifluorophenyl)-1H-1,2,3-triazol-1-yl)tetrahydro-2H-pyran-3-ol | | | MeCN/EtOH 5 min run | | |
| 2.44.141S.I | (2R,3R,4S,5R,6S)-6-(((S)-(4-Chloro-3-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.97 | 665.11 | ChiralCel OZ-H B: 30% (1/1) MeCN/EtOH 5 min run | 2.98 | 3.5 |
| 2.44.142.I. | (2R,3R,4S,5R,6S)-6-(((4,4-Difluoro-1-hydroxycyclohexyl)(3-ethylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.82 | 645.42 | | | 0.05 |
| 2.44.142R.I. | (2R,3R,4S,5R,6S)-6-(((R)-(4,4-Difluoro-1-hydroxycyclohexyl)(3-ethylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol [1,3-di-deoxy-1-((4,4-difluoro-1-hydroxy-cyclohexan-1-yl)-(3-(-ethyl)pyridin-2-yl)methyl-(R)-thio)-2-O-methyl-3-[4-(3,4,5-trifluorophenyl)-1H-1,2,3-triazol-1-yl]-b-D-galactopyranoside] | 0.81 | 645.19 | Chiralpak IC B: 20% (1/1) MeCN/EtOH 5 min run | 2.32 | 0.03 |
| 2.44.142S.I. | (2R,3R,4S,5R,6S)-6-(((S)-(4,4-Difluoro-1-hydroxycyclohexyl)(3-ethylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.81 | 645.21 | Chiralpak IC B: 20% (1/1) MeCN/EtOH 5 min run | 3.32 | 8.11 |
| 2.44.143.I. | (2R,3R,4S,5R,6S)-6-(((3,4-Dichloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.02 | 685.07 | | | 0.14 |
| 2.44.143R.I. | (2R,3R,4S,5R,6S)-6-(((S)-(3,4-Dichloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.02 | 685.07 | Chiralpak ID B: 30% (1/1) MeCN/EtOH 5 min run | 1.23 | 0.07 |
| 2.44.143S.I. | (2R,3R,4S,5R,6S)-6-(((S)-(3,4-Dichloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.02 | 685.05 | Chiralpak ID B: 30% (1/1) MeCN/EtOH 5 min run | 1.65 | 9.97 |
| 2.44.144.I. | (2R,3R,4S,5R,6S)-6-(((3,6-Dichloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 1.03 | 685.07 | | | 0.25 |
| 2.43.126.I. | (2R,3R,4S,5R,6S)-6-(((4-Hydroxy-2,2-dimethyltetrahydro-2H-pyran-4-yl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.71 | 626.01 | | | 0.16 |
| 2.43.126RR.I. | (2R,3R,4S,5R,6S)-6-(((R)-((R)-4-Hydroxy-2,2-dimethyltetrahydro-2H-pyran-4-yl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.72 | 625.93 | Chiralpak IC B: 30% (1/1/0.1) MeCN/2-PrOH/DEA 4 min run | 1.7 | 0.73 |
| 2.43.126RS.I. | (2R,3R,4S,5R,6S)-6-(((R)-((S)-4-Hydroxy-2,2-dimethyltetrahydro-2H-pyran-4-yl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.73 | 626.04 | Chiralpak IC B: 30% (1/1/0.1) MeCN/2-PrOH/DEA 4 min run | 1.97 | 0.04 |

TABLE 11-continued

| Example | Name | $t_R$ | $[M + H]^+$ | HPLC conditions | $t_R$ chiral | $IC_{50}$ [uM] |
|---|---|---|---|---|---|---|
| 2.43.126SR.I. | (2R,3R,4S,5R,6S)-6-(((S)-((R)-4-Hydroxy-2,2-dimethyltetrahydro-2H-pyran-4-yl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.72 | 625.97 | Chiralpak IC B: 30% (1/1/0.1) MeCN/2-PrOH/DEA 4 min run | 2.6 | 3.5 |
| 2.43.126SS.I. | (2R,3R,4S,5R,6S)-6-(((S)-((S)-4-Hydroxy-2,2-dimethyltetrahydro-2H-pyran-4-yl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.72 | 625.96 | Chiralpak IC B: 30% (1/1/0.1) MeCN/2-PrOH/DEA 4 min run | 2.2 | 1.9 |
| 2.44.145.I. | ((2R,3R,4S,5R,6S)-6-(((5-Cyclopropyl-4-methylisoxazol-3-yl)(4,4-difluoro-1-hydroxycyclohexyl)methyl)thio)-2-(hydroxymethyl)-5-methoxy-4-(3,4,5-trifluorophenyl)-1H-1,2,3-triazol-1-yl)tetrahydro-2H-pyran-3-ol | 1.01 | 661.14 | | | 0.71 |
| 2.44.145R.I. | (2R,3R,4S,5R,6S)-6-(((R)-(5-Cyclopropyl-4-methylisoxazol-3-yl)(4,4-difluoro-1-hydroxycyclohexyl)methyl)thio)-2-(hydroxymethyl)-5-methoxy-4-(3,4,5-trifluorophenyl)-1H-1,2,3-triazol-1-yl)tetrahydro-2H-pyran-3-ol | 1.04 | 661.09 | Chiralpak IC B: 25% MeOH 3 min run | 1.95 | 0.25 |
| 2.44.145S.I. | (2R,3R,4S,5R,6S)-6-(((S)-(5-Cyclopropyl-4-methylisoxazol-3-yl)(4,4-difluoro-1-hydroxycyclohexyl)methyl)thio)-2-(hydroxymethyl)-5-methoxy-4-(3,4,5-trifluorophenyl)-1H-1,2,3-triazol-1-yl)tetrahydro-2H-pyran-3-ol | 1.03 | 661.09 | Chiralpak IC B: 25% MeOH 3 min run | 1.45 | 11.2 |
| 2.44.146.I. | (2R,3R,4S,5R,6S)-6-(((4,4-Difluoro-1-hydroxycyclohexyl)(4-ethyl-5-propylisoxazol-3-yl)methyl)thio)-2-(hydroxymethyl)-5-methoxy-4-(3,4,5-trifluorophenyl)-1H-1,2,3-triazol-1-yl)tetrahydro-2H-pyran-3-ol | 1.07 | 677.18 | | | 0.12 |
| 2.44.147.I. | (2R,3R,4S,5R,6S)-6-(((4,4-Difluoro-1-hydroxycyclohexyl)(3-methyl-4-(trifluoromethyl)pyridin-2-yl)methyl)thio)-2-(hydroxymethyl)-5-methoxy-4-(3,4,5-trifluorophenyl)-1H-1,2,3-triazol-1-yl)tetrahydro-2H-pyran-3-ol | 1.07 | 699.08 | | | 0.24 |
| 2.44.147R.I. | (2R,3R,4S,5R,6S)-6-(((R)-(4,4-Difluoro-1-hydroxycyclohexyl)(3-methyl-4-(trifluoromethyl)pyridin-2-yl)methyl)thio)-2-(hydroxymethyl)-5-methoxy-4-(3,4,5-trifluorophenyl)-1H-1,2,3-triazol-1-yl)tetrahydro-2H-pyran-3-ol | 1.05 | 699.29 | Chiralpak IB B: 15% EtOH/0.1% DEA 3.5 min run | 2.15 | 0.19 |
| 2.44.147S.I. | (2R,3R,4S,5R,6S)-6-(((S)-(4,4-Difluoro-1-hydroxycyclohexyl)(3-methyl-4-(trifluoromethyl)pyridin-2-yl)methyl)thio)-2-(hydroxymethyl)-5-methoxy-4-(3,4,5-trifluorophenyl)-1H-1,2,3-triazol-1-yl)tetrahydro-2H-pyran-3-ol | 1.05 | 699.28 | Chiralpak IB B: 15% EtOH/0.1% DEA 3.5 min run | 2.55 | 5.3 |
| 2.44.148R.I. | (2R,3R,4S,5R,6S)-6-(((R)-(3-Chloro-6-methylpyridin-2-yl)(4,4-difluoro-1-hydroxycyclohexyl)methyl)thio)-2-(hydroxymethyl)-5-methoxy-4-(3,4,5-trifluorophenyl)-1H-1,2,3-triazol-1-yl)tetrahydro-2H-pyran-3-ol | 1.05 | 665.06 | Chiralpak IC B: 20% (1/1) EtOH/MeCN 4 min run | 1.8 | 0.24 |
| 2.44.148S.I. | (2R,3R,4S,5R,6S)-6-(((S)-(3-Chloro-6-methylpyridin-2-yl)(4,4-difluoro-1-hydroxycyclohexyl)methyl)thio)-2-(hydroxymethyl)-5-methoxy-4-(3,4,5-trifluorophenyl)-1H-1,2,3-triazol-1-yl)tetrahydro-2H-pyran-3-ol | 1.05 | 665.03 | Chiralpak IC B: 20% (1/1) EtOH/MeCN 4 min run | 2.3 | 6.99 |
| 2.44.119.I. | (2R,3R,4S,5R,6S)-6-(((4,4-Difluoro-1-hydroxycyclohexyl)(3,5,6-trimethylpyrazin-2-yl)methyl)thio)-2-(hydroxymethyl)-5-methoxy-4-(3,4,5-trifluorophenyl)-1H-1,2,3-triazol-1-yl)tetrahydro-2H-pyran-3-ol | 0.98 | 660.12 | | | 0.26 |

TABLE 11-continued

| Example | Name | $t_R$ | $[M + H]^+$ | HPLC conditions | $t_R$ chiral | $IC_{50}$ [uM] |
|---|---|---|---|---|---|---|
| 2.44.119R.I. | (2R,3R,4S,5R,6S)-6-(((R)-(4,4-Difluoro-1-hydroxycyclohexyl)(3,5,6-trimethylpyrazin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.99 | 660.08 | Chiralcel OJ-H B: 50% EtOH/0.1% DEA 3 min run | 1.1 | 0.09 |
| 2.44.119S.I. | (2R,3R,4S,5R,6S)-6-(((S)-(4,4-Difluoro-1-hydroxycyclohexyl)(3,5,6-trimethylpyrazin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.98 | 660.11 | Chiralcel OJ-H B: 50% EtOH/0.1% DEA 3 min run | 2.0 | 5.11 |
| 2.44.149.I. | (2R,3R,4S,5R,6S)-6-(((4,4-Difluoro-1-hydroxycyclohexyl)(3,6-dimethylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol | 0.8 | 645.13 | | | 0.4 |
| 2.72.126.I | 9-((((2S,3R,4S,5R,6R)-5-Hydroxy-6-(hydroxymethyl)-3-methoxy-4-(4-(3,4,5-trifluorophenyl)-1H-1,2,3-triazol-1-yl)tetrahydro-2H-pyran-2-yl)thio)(3-methylpyridin-2-yl)methyl)-3-oxaspiro[5.5]undecan-9-ol | 0.74 | 665.18 | | | 0.13 |

Example 2.44.126.II (2R,3R,4S,5R,6S)-6-(((4,4-Difluoro-1-hydroxycyclohexyl)(3-methylpyridin-2-yl)methyl)thio)-5-ethoxy-2-(hydroxymethyl)-4-(4-(3,4,5-trifluorophenyl)-1H-1,2,3-triazol-1-yl)tetrahydro-2H-pyran-3-ol Example 2.44.126.II. is prepared from 1-((4-chloro-3-methylpyridin-2-yl)(mercapto)methyl)-4,4-difluorocyclohexan-1-ol (prepared in analogy to Intermediate 7) and Intermediate 11 according to the procedures described for Example 2.40.119. as a beige solid. LC-MS (A): $t_R$=0.81 min; [M+H]$^+$: 645.42.

LC-MS and Gal-3 inhibition data from Examples 2.44.126.II. are listed in Table 14 below. The LC-MS conditions used were LC-MS (A).

Example 2.51.112.I 1-(Cyclopropylsulfonyl)-4-((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidin-4-ol 1. 1-(Cyclopropylsulfonyl)-4-((((4aR,6S,7R,8S,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)thio)(2-(trifluoromethyl)phenyl)methyl)piperidin-4-ol To a solution of Intermediate 12 (0.06 g, 0.087 mmol) in DCM (3.0 mL) at rt are added cyclopropylsulfonyl chloride

TABLE 12

| Example | Name | $t_R$ | $[M + H]^+$ | HPLC conditions | $t_R$ chiral | $IC_{50}$ [uM] |
|---|---|---|---|---|---|---|
| 2.44.126.II. | (2R,3R,4S,5R,6S)-6-(((4,4-Difluoro-1-hydroxycyclohexyl)(3-methylpyridin-2-yl)methyl)thio)-5-ethoxy-2-(hydroxymethyl)-4-(4-(3,4,5-trifluorophenyl)-1H-1,2,3-triazol-1-yl)tetrahydro-2H-pyran-3-ol | 0.81 | 645.42 | | | 0.16 |
| 2.44.126R.II. | (2R,3R,4S,5R,6S)-6-(((R)-(4,4-Difluoro-1-hydroxycyclohexyl)(3-methylpyridin-2-yl)methyl)thio)-5-ethoxy-2-(hydroxymethyl)-4-(4-(3,4,5-trifluorophenyl)-1H-1,2,3-triazol-1-yl)tetrahydro-2H-pyran-3-ol | 0.81 | 645.13 | Chiralpak IC B: 20% EtOH/0.1% DEA 4 min run | 1.59 | 0.11 |
| 2.44.126S.II. | (2R,3R,4S,5R,6S)-6-(((S)-(4,4-Difluoro-1-hydroxycyclohexyl)(3-methylpyridin-2-yl)methyl)thio)-5-ethoxy-2-(hydroxymethyl)-4-(4-(3,4,5-trifluorophenyl)-1H-1,2,3-triazol-1-yl)tetrahydro-2H-pyran-3-ol | 0.82 | 645.12 | Chiralpak IC B: 20% EtOH/0.1% DEA 4 min run | 2.03 | 0.98 |

(0.01 mL, 0.105 mmol, 1.2 eq) and DIPEA (33.9 uL, 0.26 mmol, 3.0 eq). The reaction mixture is stirred at rt for 15 h, partitioned between DCM and water, the layers are separated and the aqueous layer is extracted with DCM (3×). The combined organic layer is dried over MgSO4, filtered and solvent removed in vacuo to give a brown oil, that is purified by prep HPLC/MS (I) to yield the title compound (0.011 g, 16%) as a white solid. LC-MS (A): $t_R$=1.11 min; $[M+H]^+$: 793.22.

2. 1-(Cyclopropylsulfonyl)-4-(((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidin-4-ol (2.51.112.I.)

To a mixture of 1-(cyclopropylsulfonyl)-4-(((((4aR,6S,7R,8S,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)thio)(2-(trifluoromethyl)phenyl)methyl)piperidin-4-ol (0.011 g, 0.014 mmol) in water is added AcOH (0.5 mL) and the solution is stirred at 60° C. for 2 h, then at rt over 15 h. A mixture water/MeCN 1/1 (1.0 mL) and NH4OH are added (until pH 5-6), while cooling (0° C.) and the solution is purified by prep HPLC/MS (I) to obtain a white solid (0.006 g). LC-MS (A): $t_R$=0.98 min; $[M+H]^+$: 753.11.

Example 2.48.112.I 1-(4-Hydroxy-4-(((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidin-1-yl)ethan-1-one Example 2.48.112.I. is obtained as a side-product during the synthesis of Example 2.51.112.I. Step 1. and deprotected in analogy to Step 2. of the same Example as a white solid. LC-MS (A): $t_R$=0.92 min; $[M+H]^+$: 691.12.

Example 2.49.112.I (N-Cyclopropyl-4-hydroxy-4-(((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidine-1-carboxamide Example 2.49.112.I. is obtained from Intermediate 12 and isocyanato cyclopropane in analogy to Example 2.51.112.I. as a white solid. LC-MS (A): $t_R$=0.91 min; $[M+H]^+$: 732.2.

LC-MS and Gal-3 inhibition data from Examples 2.51.112.I. to Example 2.49.112.I. are listed in Table 13 below. The LC-MS conditions used were LC-MS (A).

TABLE 13

| Example | Name | $t_R$ | $[M + H]^+$ | $IC_{50}$ [uM] |
| --- | --- | --- | --- | --- |
| 2.51.112.I. | 1-(Cyclopropylsulfonyl)-4-(((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidin-4-ol | 0.98 | 753.11 | 0.08 |
| 2.48.112.I. | 1-(4-Hydroxy-4-(((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidin-1-yl)ethan-1-one | 0.92 | 691.12 | 0.19 |
| 2.49.112.I. | (N-Cyclopropyl-4-hydroxy-4-(((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(2-(trifluoromethyl)phenyl)methyl)piperidine-1-carboxamide | 0.91 | 732.2 | 0.21 |

Example 16.44.126.I (2R,3R,4S,5R,6S)-6-(((4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol

1. 4,4-Difluoro-1-(mercapto(3-methylpyridin-2-yl)methyl)cyclohexan-1-ol 4,4-Difluoro-1-(mercapto(3-methylpyridin-2-yl)methyl)cyclohexan-1-ol is prepared from S-(tetrahydro-2H-pyran-2-yl) ethanethioate, 2-(bromomethyl)-3-methylpyridine and 4,4-difluorocyclohexan-1-one in analogy to Intermediate 7 as a yellow oil. LC-MS (A): $t_R$=0.62 min; [M+H]$^+$: 273.91

2. (2R,3R,4S,5R,6S)-2-(Acetoxymethyl)-4-azido-6-(((4,4-difluoro-1-hydroxycyclohexyl)(3-methylpyridin-2-yl)methyl)thio)tetrahydro-2H-pyran-3,5-diyl diacetate (2R,3R,4S,5R,6S)-2-(Acetoxymethyl)-4-azido-6-(((4,4-difluoro-1-hydroxycyclohexyl)(3-methylpyridin-2-yl)methyl)thio)tetrahydro-2H-pyran-3,5-diyl diacetate is prepared from 4,4-difluoro-1-(mercapto(3-methylpyridin-2-yl)methyl)cyclohexan-1-ol and Intermediate 2 in analogy to Intermediate 9 as a white powder. LC-MS (A): $t_R$=0.81 min; [M+H]$^+$: 587.20.

3. (2S,3R,4S,5R,6R)-4-Azido-2-(((4,4-difluoro-1-hydroxycyclohexyl)(3-methylpyridin-2-yl)methyl)thio)-6-(hydroxymethyl)tetrahydro-2H-pyran-3,5-diol To a suspension of (2R,3R,4S,5R,6S)-2-(acetoxymethyl)-4-azido-6-(((4,4-difluoro-1-hydroxycyclohexyl)(3-methylpyridin-2-yl)methyl)thio)tetrahydro-2H-pyran-3,5-diyl diacetate (1.04 g, 1.77 mmol) in MeOH at rt (21.0 mL) is added NaOMe (0.14 g, 2.66 mmol, 1.5 eq). The mixture is stirred at rt for 15 h, neutralized with DOWEX 50WX2, filtered and solvent removed in vacuo to give the title compound as an orange oil (0.87 g, >99%), that is used without further purification. LC-MS (A): $t_R$=0.48 min; [M+H]$^+$: 461.12.

4. (4aR,6S,7R,8R,8aR)-8-Azido-6-(((4,4-difluoro-1-hydroxycyclohexyl)(3-methylpyridin-2-yl)methyl)thio)-2,2-dimethylhexahydropyrano[3,2-d][1,3]dioxin-7-ol A solution of (2S,3R,4S,5R,6R)-4-azido-2-(((4,4-difluoro-1-hydroxycyclohexyl)(3-methylpyridin-2-yl)methyl)thio)-6-(hydroxymethyl)tetrahydro-2H-pyran-3,5-diol (0.75 g, 1.62 mmol) in THF (11.5 mL) and acetone (11.5 mL) is treated with 2,2-dimethoxypropane (2.03 mL, 16.2 mmol, 10.0 eq) and p-TsOH H$_2$O (0.04 g, 0.18 mmol, 0.1 eq) and stirred at 50° C. for 9 h. The reaction mixture is concentrated under reduced pressure, diluted with EA, washed with aq. sat. NaHCO$_3$, dried over MgSO$_4$, filtered and solvent removed in vacuo to give a white solid (0.72 g, 89%), that is used without further purification. LC-MS (A): $t_R$=0.65-0.68 min: [M+H]$^+$: 501.16

5. 1-((((4aR,6S,7R,8S,8aR)-8-Azido-7-methoxy-2,2-dimethylhexahydropyrano[3,2-d][1,3]dioxin-6-yl)thio)(3-methylpyridin-2-yl)methyl)-4,4-difluorocyclohexan-1-ol To a solution of (4aR,6S,7R,8R,8aR)-8-azido-6-(((4,4-difluoro-1-hydroxycyclohexyl)(3-methylpyridin-2-yl)methyl)thio)-2,2-dimethylhexahydropyrano[3,2-d][1,3]dioxin-7-ol (0.57 g, 1.14 mmol) in DMF (12.0 mL) at rt is added MeI (0.43 mL, 6.87 mmol, 6.0 eq). After 5 min CsCO$_3$ (1.23 g, 3.78 mmol, 3.3 eq) is added and the reaction mixture is stirred at rt for 15 h, then partitioned between water and EA. The layers are separated and the aq. layer is extracted with EA (3×). The combined organic layer is washed with brine, dried over MgSO$_4$, filtered and solvent removed in vacuo to give a brown oil, that is purified by combi flash (ISCO system, product added dry on isolute, 12 g column, Hept/EA 100/0 to 20/80, Rf(Hept/EA 1/1)=0.33 & 0.42) to yield the title compound as a yellow oil (0.59 g, >99%). LC-MS (A): $t_R$=0.76-0.78 min; [M+H]$^+$: 515.18

6. 1-((((4aR,6S,7R,8S,8aR)-8-(4-(3,4-Difluorophenyl)-1H-1,2,3-triazol-1-yl)-7-methoxy-2,2-dimethylhexahydropyrano[3,2-d][1,3]dioxin-6-yl)thio)(3-methylpyridin-2-yl)methyl)-4,4-difluorocyclohexan-1-ol To a solution of 1-((((4aR,6S,7R,8S,8aR)-8-azido-7-methoxy-2,2-dimethylhexahydropyrano[3,2-d][1,3]dioxin-6-yl)thio)(3-methylpyridin-2-yl)methyl)-4,4-difluorocyclohexan-1-ol (0.058 g, 0.11 mmol) in DMF (1.0 mL) at rt are added 4-ethynyl-1,2-difluorobenzene (0.0202 mL, 0.16 mmol, 1.5 eq), CuI (0.07 g, 0.01 mmol, 0.1 eq)) and DIPEA (0.05 mL, 0.32 mmol, 3.0 eq). The reaction mixture is stirred at rt for 3 h, diluted with EA. The org. layer is washed with aq. sat. NH$_4$Cl, brine, dried over MgSO$_4$, filtered and solvent concentrated in vacuo to afford a beige solid. The crude material is purified by preparative prepHPLC/MS (I) to yield the title compound as a white solid (0.05 g, 77%). LC-MS (A): $t_R$=0.92 min; [M+H]$^+$: 653.21

7. (2R,3R,4S,5R,6S)-6-(((4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol (16.44.126.I.)

To a mixture of 1-((((4aR,6S,7R,8S,8aR)-8-(4-(3,4-difluorophenyl)-1H-1,2,3-triazol-1-yl)-7-methoxy-2,2-dimethylhexahydropyrano[3,2-d][1,3]dioxin-6-yl)thio)(3-methylpyridin-2-yl)methyl)-4,4-difluorocyclohexan-1-ol (0.05 g, 0.08 mmol) in water (2.0 mL) is added AcOH (2.0 mL), the solution is heated at 80° C. for 15 h. The reaction mixture is cooled (00), quenched with (H$_2$O/MeCN 1/1, 1.0 mL) and aq. NH$_4$OH is added (until pH 5-6) at 0° C. The resulting solution is purified by preparative HPLC/MS(I) to give the title compound as a white solid (0.03 g, 64%). LC-MS (A): $t_R$=0.75 min; [M+H]$^+$: 613.36.

Example 16.44.126R.I (2R,3R,4S,5R,6S)-6-(((R)-(4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol Separation of the epimers of Example 16.44.126.I. (0.032 g) by chiral preparative HPLC (VIII) yielded the title compound (0.009 g) as a white solid. Chiral analytical HPLC (O): $t_R$=1.4 min. LC-MS (A): $t_R$=0.75 min: [M+H]$^+$: 613.13.

Example 16.44.126S.I (2R,3R,4S,5R,6S)-6-(((S)-(4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol Separation of the epimers of Example 16.44.126.I. (0.032 g) by chiral preparative HPLC (VIII) yielded the title compound (0.008 g) as a white solid. Chiral analytical HPLC (O): $t_R$=2.0 min. LC-MS (A): $t_R$=0.75 min; [M+H]$^+$: 613.13.

Following examples are prepared starting from 1-((((4aR,6S,7R,8S,8aR)-8-azido-7-methoxy-2,2-dimethylhexahydropyrano[3,2-d][1,3]dioxin-6-yl)thio)(3-methylpyridin-2-yl)methyl)-4,4-difluorocyclohexan-1-ol Example 16.44.126.I. Step 5. and the corresponding alkynes in analogy to Example 16.44.126.I. Step 6-7. LC-MS and Gal-3 inhibition data are listed in Table 14 below. The LC-MS conditions used were LC-MS (A). Chiral analytical HPLC (I) (conditions and retention time) and inhibition data of the epimers R and S of selected Examples are also listed.

TABLE 14

| Example | Name | $t_R$ | [M + H]$^+$ | HPLC conditions | $t_R$ chiral | IC$_{50}$ [uM] |
|---|---|---|---|---|---|---|
| 16.44.126.I. | (2R,3R,4S,5R,6S)-6-(((4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol | 0.75 | 613.36 | | | 0.09 |
| 16.44.126R.I. | (2R,3R,4S,5R,6S)-6-(((R)-(4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol | 0.75 | 613.13 | ChiralCel OZ-H B: 40% (1/1) MeCN/EtOH 5 min run | 1.42 | 0.08 |
| 16.44.126S.I. | (2R,3R,4S,5R,6S)-6-(((S)-(4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol | 0.75 | 613.13 | ChiralCel OZ-H B: 40(1/1) MeCN/EtOH 5 min run | 2.01 | 1.87 |
| 21.44.126.I. | (2R,3R,4S,5R,6S)-6-(((4,4-Difluoro-1-hydroxycyclohexyl)(3-methylpyridin-2-yl)methyl)thio)-2-(hydroxymethyl)-5-methoxy-4-(4-(2,3,4-trifluorophenyl)-1H-1,2,3-triazol-1-yl)tetrahydro-2H-pyran-3-ol | 0.76 | 631.24 | | | 0.06 |
| 22.44.126.I. | (2R,3R,4S,5R,6S)-4-(4-(4-Chloro-2,3-difluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol | 0.79 | 647.16 | | | 007 |
| 23.44.126.I. | (2R,3R,4S,5R,6S)-6-(((4,4-Difluoro-1-hydroxycyclohexyl)(3-methylpyridin-2-yl)methyl)thio)-4-(4-(2,3-difluoro-4-methylphenyl)-1H-1,2,3-triazol-1-yl)-2-(hydroxymethyl)-5-methoxytetrahydro-2H-pyran-3-ol | 0.77 | 627.22 | | | 0.05 |
| 18.44.126.I. | (2R,3R,4S,5R,6S)-4-(4-(4-Bromo-3,5-difluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol | 0.79 | 691.08 | | | 0.12 |
| 17.44.126.I. | (2R,3R,4S,5R,6S)-4-(4-(3,4-Dichloro-5-fluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol | 0.82 | 663.1 | | | 0.14 |
| 12.44.126.I. | (2R,3R,4S,5R,6S)-4-(4-(4-Bromo-3-fluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol | 0.78 | 675.08 | | | 0.19 |
| 11.44.126.I. | (2R,3R,4S,5R,6S)-4-(4-(4-Chloro-3,5-difluorophenyl)-1H-1,2,3-triazol-1-yl)-6-(((4,4-difluoro-1-hydroxycyclohexyl)(3-methylpyridin-2-yl)methyl)thio)-2-(hydroxymethyl)-5-methoxytetrahydro-2H-pyran-3-ol | 0.8 | 647.14 | | | 0.09 |
| 3.44.126R.I. | (2R,3R,4S,5R,6S)-6-(((R)-(4,4-Difluoro-1-hydroxycyclohexyl)(3-methylpyridin-2-yl)methyl)thio)-4-(4-(3,5-difluoro-4-methylphenyl)-1H-1,2,3-triazol-1-yl)-2- | 0.79 | 627.15 | Chiralpak IB B: 20% MeOH, 0.1% DEA | 1.98 | 0.04 |

TABLE 14-continued

| Example | Name | $t_R$ | $[M + H]^+$ | HPLC conditions | $t_R$ chiral | $IC_{50}$ [uM] |
|---|---|---|---|---|---|---|
| 3.44.126S.I. | (hydroxymethyl)-5-methoxytetrahydro-2H-pyran-3-ol (2R,3R,4S,5R,6S)-6-(((S)-(4,4-Difluoro-1-hydroxycyclohexyl)(3-methylpyridin-2-yl)methyl)thio)-4-(4-(3,5-difluoro-4-methylphenyl)-1H-1,2,3-triazol-1-yl)-2-(hydroxymethyl)-5-methoxytetrahydro-2H-pyran-3-ol | 0.8 | 627.14 | 5 min run Chiralpak IB B: 20% MeOH, 0.1% DEA 5 min run | 2.23 | 1.16 |
| 24.44.126.I. | (2R,3R,4S,5R,6S)-6-(((4,4-Difluoro-1-hydroxycyclohexyl)(3-methylpyridin-2-yl)methyl)thio)-4-(4-(6-fluoro-5-methylpyridin-3-yl)-1H-1,2,3-triazol-1-yl)-2-(hydroxymethyl)-5-methoxytetrahydro-2H-pyran-3-ol | 0.69 | 609.99 | | | 0.33 |

Galectin-1 inhibition data are listed in Table 15 below. Inhibition data of the epimers R and S of selected Examples are also listed.

TABLE 15

| Example | $IC_{50}$ [uM] | Example | $IC_{50}$ [uM] | Example | $IC_{50}$ [uM] | Example | $IC_{50}$ [uM] |
|---|---|---|---|---|---|---|---|
| 2.30.100.OMe | 56.3 | 2.31.110. | 0.4 | 2.31.120R. | 1.8 | 2.37.102. | 5.36 |
| 2.54.100. | 61.2 | 2.31.110R. | 0.28 | 2.31.120S. | 61.3 | 2.38.102. | 2.9 |
| 1.30.101. | 5.77 | 2.31.110S. | 16.7 | 2.31.121. | 5.03 | 2.38.102R. | 1.8 |
| 2.30.105. | 1.73 | 2.31.111R. | 3.19 | 2.31.122. | 2.14 | 2.38.102S. | 17 |
| 2.31.102. | 2.14 | 2.31.111S. | 30.9 | 2.31.122R | 0.67 | 2.39.128. | 1.11 |
| 2.31.102R. | 1.42 | 2.31.112. | 5.23 | 2.31.122S. | 11.2 | 2.39.128R. | 1.03 |
| 2.31.102S. | 6.98 | 2.31.112R. | 2.61 | 2.31.123. | 1.74 | 2.39.128S. | 23.2 |
| 2.31.100. | 3.71 | 2.31.112S. | 26.4 | 2.31.123R. | 1.19 | 2.39.102. | 1.6 |
| 2.31.103. | 1.23 | 2.31.113. | 3.75 | 2.31.123S. | 29.4 | 2.39.102R. | 1.14 |
| 2.31.104. | 0.6 | 2.31.114. | 2.27 | 2.31.124. | 5.15 | 2.39.102S. | 24 |
| 2.31.105. | 0.3 | 2.31.114R. | 7.24 | 2.32.120R. | 2.83 | 2.40.102. | 0.73 |
| 2.31.105R. | 0.16 | 2.31.114S. | 40.9 | 2.32.120S. | 77.4 | 2.41.102. | 1.61 |
| 2.31.105S. | 65.1 | 2.31.115. | 1.39 | 2.60.112. | 3.5 | 2.41.102R. | 0.21 |
| 2.31.106. | 0.34 | 2.31.115R. | 0.58 | 2.61.112. | 7.88 | 2.41.102S. | 65.4 |
| 2.31.106R. | 0.21 | 2.31.115S. | 47.9 | 2.62.112. | 11.7 | 2.42.102. | 18.5 |
| 2.31.106S. | 65 | 2.31.116. | 3.78 | 2.33.112. | 1.8 | 2.42.102R. | 6.4 |
| 2.31.107. | 0.24 | 2.31.117. | 4.95 | 2.33.112R. | 0.67 | 2.42.102S. | >100 |
| 2.31.107R. | 0.3 | 2.31.118R. | 0.64 | 2.33.112S. | 21.7 | 2.43.102. | 1.9 |
| 2.31.107S. | 56.6 | 2.31.118S. | 8.2 | 2.34.102. | 11.0 | 2.43.102RS. | 0.8 |
| 2.31.108. | 21.2 | 2.31.119. | 1.75 | 2.35.102. | 6.22 | 2.43.102RR. | 8.8 |
| 2.31.108R. | 0.39 | 2.31.119R. | 1.15 | 2.36.102. | 13.2 | 2.43.102SS. | 69.5 |
| 2.31.108S. | 25.8 | 2.31.119S. | 18.35 | 2.36.102R. | 3.5 | 2.43.102SR. | 55 |
| 2.31.109. | 3.23 | 2.31.120. | 3.0 | 2.36.102S. | 54.2 | 2.43.112RS. | 0.4 |
| 2.43.112RR. | 6.8 | 2.44.113. | 2.35 | 2.44.126. | 0.06 | 2.66.126R. | 0.17 |
| 2.43.112SR. | 10.9 | 2.44.113R. | 1.73 | 2.44.126R. | 0.3 | 2.66.126S. | 16.5 |
| 2.43.112SS. | 19.4 | 2.44.113S. | 56.8 | 2.44.126S. | 26.5 | 2.41.126. | 0.8 |
| 2.35.125. | 1.46 | 2.44.106R. | 0.02 | 2.44.129. | 0.35 | 2.41.126R. | 0.7 |
| 2.35.125R. | 0.81 | 2.44.106S. | 1.9 | 2.44.129R. | 0.2 | 2.41.126S. | 70.4 |
| 2.35.125S. | 21.8 | 2.41.112. | 0.9 | 2.44.129S. | 6.3 | 2.45.112. | 0.46 |
| 2.39.125R. | 0.28 | 2.41.112R. | 0.9 | 2.44.130. | 0.13 | 2.46.112. | 0.27 |
| 2.39.125S. | 21.8 | 2.41.112S. | 59.4 | 2.44.130R. | 0.16 | 2.47.112R. | 0.12 |
| 2.39.119R. | 0.73 | 2.41.125. | 5.7 | 2.44.130S. | 5.65 | 2.47.112S. | 17.5 |
| 2.39.119S. | 18.9 | 2.41.125R. | 0.13 | 2.44.131. | 0.22 | 2.48.112. | 0.75 |
| 2.39.120R. | 0.61 | 2.41.125S. | 7.47 | 2.44.131R. | 0.09 | 2.49.112R. | 0.16 |
| 2.39.120S. | 70 | 2.41.119. | 20 | 2.44.131S. | 13.7 | 2.49.112S. | 12.1 |
| 2.44.120R. | 0.38 | 2.41.119R. | 0.49 | 2.44.132. | 0.16 | 2.50.112R. | 0.37 |
| 2.44.120S. | 22.6 | 2.41.119S. | 19.9 | 2.44.132R. | 0.05 | 2.50.112S. | 15.8 |
| 2.44.105. | 0.08 | 2.40.112. | 0.42 | 2.44.132S. | 4.7 | 2.57.112. | 0.58 |
| 2.44.105R. | 0.04 | 2.40.112R. | 0.15 | 2.44.133. | 0.45 | 2.57.112R. | 1.2 |
| 2.44.105S. | 0.52 | 2.40.112S. | 21.7 | 2.44.133R. | 0.16 | 2.57.112S. | 76.5 |
| 2.44.119R. | 0.23 | 2.40.125. | 0.53 | 2.44.133S. | 15.8 | 2.58.112. | 1.47 |
| 2.44.119S. | 7.21 | 2.40.125R. | 0.04 | 2.44.134. | 0.14 | 2.59.112. | 1.28 |
| 2.44.125R. | 0.2 | 2.40.125S. | 11.2 | 2.44.134R. | 0.05 | 3.31.112. | 4.9 |
| 2.44.125S. | 3.41 | 2.40.119. | 0.27 | 2.44.134S. | 2.7 | 3.31.112S. | 2.84 |
| 2.44.111R. | 1.06 | 2.40.119R. | 0.11 | 2.44.135R. | 0.22 | 3.31.112S. | 54.2 |
| 2.44.111S. | 47.5 | 2.40.119S. | 10.8 | 2.44.135S. | 5.43 | 4.31.112. | 2.27 |
| 2.44.112. | 0.95 | 2.38.125. | 0.76 | 2.66.120. | 0.33 | 5.31.112. | 3.58 |
| 2.44.112R. | 0.77 | 2.38.125R. | 0.48 | 2.66.120R. | 0.07 | 2.44.126R.I. | 0.68 |
| 2.44.112S. | 17.6 | 2.38.125S. | 15.1 | 2.66.120S. | 24.1 | 2.44.125R.I. | 0.26 |
| 2.39.125R.I. | 0.46 | 2.44.139S.I. | >100 | 2.43.125SS.I. | 12.6 | 21.44.126I. | 0.38 |

TABLE 15-continued

| Example | IC$_{50}$ [uM] | Example | IC$_{50}$ [uM] | Example | IC$_{50}$ [uM] | Example | IC$_{50}$ [uM] |
|---|---|---|---|---|---|---|---|
| 2.44.137.I. | 4.36 | 2.44.140R.I. | 0.7 | 2.44.145.I. | 1.26 | 22.44.126.I. | 0.92 |
| 2.44.137R.I. | 0.72 | 2.41.120R.I. | 0.5 | 2.44.145R.I. | 1.2 | 23.44.126.I. | 0.55 |
| 2.43.112RS.I. | 1.3 | 2.66.120R.I. | 0.58 | 2.44.145S.I. | 31 | 18.44.126.I. | 3.47 |
| 2.66.126R.I. | 0.09 | 2.39.128R.I. | 2.36 | 2.44.146.I. | 0.17 | 17.44.126.I. | 1.68 |
| 2.41.126R.I. | 0.8 | 2.44.130R.I. | 0.16 | 2.44.147.I. | 1.24 | 12.44.126.I. | 3.24 |
| 2.43.102RS.I. | 1.9 | 2.44.131R.I. | 0.1 | 2.44.147R.I. | 0.76 | 11.44.126.I. | 2.43 |
| 2.44.132R.I. | 0.1 | 2.44.133.I. | 1.22 | 2.44.147S.I. | 31.8 | 3.44.126R.I. | 2.43 |
| 2.44.134R.I. | 0.11 | 2.44.133R.I. | 0.66 | 2.44.148R.I. | 3.04 | 3.44.126S.I. | 20 |
| 2.44.135R.I. | 0.2 | 2.44.133S.I. | 7.54 | 2.44.148S.I. | 31 | 24.44.126.I | 0.16 |
| 2.44.129R.I. | 0.3 | 2.44.141.I. | 0.86 | 2.44.119.I. | 1.3 | 2.44.135. | 0.45 |
| 2.39.120R.I. | 0.56 | 2.44.141R.I. | 0.35 | 2.44.119R.I. | 0.45 | 2.39.120S.I. | 27.3 |
| 2.44.105R.I. | 0.15 | 2.44.141S.I. | 10.5 | 2.44.119S.I. | 28.6 | | |
| 2.44.105S.I. | 53.3 | 2.44.142.I. | 0.19 | 2.44.149.I. | 2.8 | | |
| 2.44.120R.I. | 0.61 | 2.44.142R.I. | 0.1 | 2.72.126.I. | 0.73 | | |
| 2.44.106R.I. | 0.21 | 2.44.142S.I. | 8.31 | 2.44.126.II. | 1.32 | | |
| 2.44.136.I. | 2.53 | 2.44.143.I. | 0.85 | 2.44.126R.II. | 0.87 | | |
| 2.44.136R.I. | 1.9 | 2.44.143R.I. | 0.86 | 2.44.126S.II. | 24.3 | | |
| 2.44.136S.I. | >100 | 2.44.143S.I. | 9.77 | 2.51.112.I. | 0.35 | | |
| 2.44.138.I. | 0.84 | 2.44.144.I. | 4.16 | 2.48.112.I. | 0.4 | | |
| 2.44.138R.I. | 0.4 | 2.43.125.I. | 2.2 | 2.49.112.I. | 0.49 | | |
| 2.44.138S.I. | >100 | 2.43.125RR.I. | 4.63 | 16.44.126.I. | 0.73 | | |
| 2.44.139.I. | 3.9 | 2.43.125RS.I. | 0.7 | 16.44.126R.I. | 0.57 | | |
| 2.44.139R.I. | 0.54 | 2.43.125SR.I. | 27.1 | 16.44.126S.I. | 54.2 | | |

Biological Assay

Evaluation of Compound Inhibitory Activity (IC$_{50}$)

The inhibitory activity of compounds is determined in competitive binding assays. This spectrophotometric assay measures the binding of biotinylated human Gal-3 (hGal-3) or human Gal-1 (hGal-1), respectively, to a microplate-adsorbed glycoprotein, asialofetuin (ASF) (Proc Natl Acad Sci USA. 2013 Mar. 26; 110(13):5052-7.).

Briefly, compounds are serially diluted in DMSO (working dilutions). ASF-coated 384 well plates are supplemented with 22.8 µL/well of biotinylated hGal-3 or hGal-1 in assay buffer (i.e. 300-1000 ng/mL biotinylated hGal-3 or hGal-1) to which 1.2 µL of compound working dilutions are added and mixed.

Plates are incubated for 3 hours at 4° C., then washed with cold assay buffer (3×50 uL), incubated for 1 hour with 25 µL/well of a streptavidin-peroxidase solution (diluted in assay buffer to 80 ng/mL) at 4° C., followed by further washing steps with assay buffer (3×50 uL). Finally, 25 µL/well of ABTS substrate is added. OD (410 nm) is recorded after 30 to 45 min and IC$_{50}$ values are calculated.

The calculated IC$_{50}$ values may fluctuate depending on the daily assay performance. Fluctuations of this kind are known to those skilled in the art. IC$_{50}$ values from several measurements are given as mean values.

The invention claimed is:

1. A compound of Formula (I)

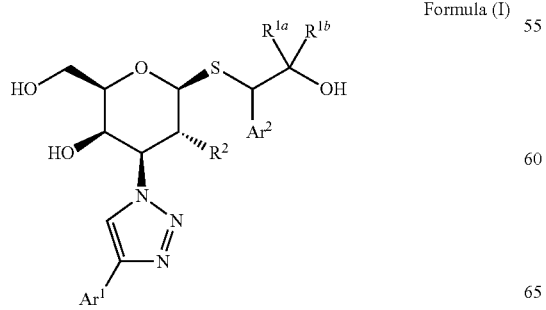

Formula (I)

wherein

Ar$^1$ represents
  aryl which is mono-, di-, tri-, tetra-, or penta-substituted, wherein the substituents are independently selected from halogen, methyl, cyano, and methoxy; or
  5- or 6-membered heteroaryl, wherein said 5- or 6-membered heteroaryl independently is unsubstituted, mono- or di-substituted, wherein the substituents are independently selected from halogen, methyl, cyano, and methoxy;

Ar$^2$ represents
  phenyl or 5- or 6-membered heteroaryl, wherein said phenyl or 5- or 6-membered heteroaryl independently is unsubstituted, mono-, di-, or tri-substituted wherein the substituents independently are $C_{1-6}$-alkyl, $C_{3-6}$-cycloalkyl, $C_{1-3}$-fluoroalkyl, $C_{1-3}$-fluoroalkoxy, halogen, hydroxy-$C_{1-3}$-alkyl, or phenyl; or naphthyl;

R$^{1a}$ represents hydrogen; and R$^{1b}$ represents
  —$C_{2-4}$-alkyl; or
  —$C_{0-1}$-alkylene-Ar$^{1b}$, wherein Ar$^{1b}$ represents phenyl or 5- or 6-membered heteroaryl, wherein said phenyl or 5- or 6-membered heteroaryl independently is unsubstituted, mono- or di-substituted with methyl;

or R$^{1a}$ and R$^{1b}$ both represent hydrogen, methyl, ethyl, or n-propyl;

or R$^{1a}$ and R$^{1b}$ together with the carbon atom to which they are attached form a 3- to 6-membered ring selected from
  $C_{3-6}$-cycloalkylene, wherein said $C_{3-6}$-cycloalkylene independently is unsubstituted, mono-, or di-substituted, wherein the substituents independently are methyl or fluoro;
  tetrahydro-2H-pyran-4,4-diyl, which is unsubstituted, di-, or tetra-substituted with methyl;
  tetrahydro-2H-thiopyran-1,1-dioxide-4,4-diyl; or
  piperidine-4,4-diyl, pyrrolidine-3,3-diyl, or azetidine-3,3-diyl wherein the nitrogen of said piperidine, pyrrolidine or azetidine independently is unsubstituted, or substituted with —$C_{1-3}$-alkyl, —$C_{0-2}$-alkylene-$C_{3-6}$-cycloalkyl, or -L-R$^{N1}$ wherein -L- represents —CO—, —SO$_2$—, *—CO—NH—, *—CO—O—, or *—SO$_2$—NH—, and R$^{N1}$ represents —C$_{1-3}$-alkyl or —C$_{0-2}$-alkylene-C$_{3-6}$-cycloalkyl;

wherein in the above groups the asterisks indicate the bond which is connected to the rest of the molecule; or R$^{1a}$ and R$^{1b}$ together with the carbon atom to which they are attached form a spiro-bicyclic ring system of the structure (S$^{1AB}$)

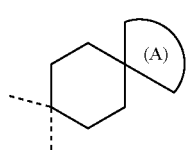

(S$^{1AB}$)

wherein ring (A) represents a 3- to 6-membered non-aromatic carbocyclic ring, wherein said 3- to 6-membered non-aromatic carbocyclic ring optionally contains one ring oxygen atom and wherein said 3- to 6-membered non-aromatic carbocyclic ring is unsubstituted or di-substituted with fluoro; and R$^2$ represents hydroxy or C$_{1-3}$-alkoxy;

or a pharmaceutically acceptable salt thereof.

2. A compound according to claim 1 wherein said compound is a compound of Formula (I$_R$),

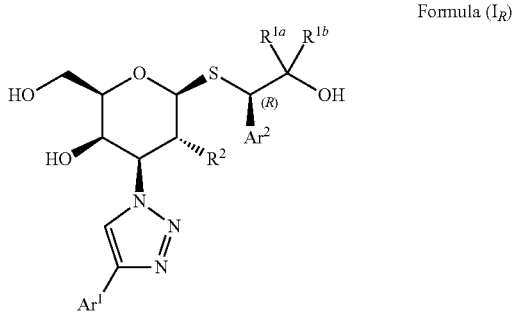

Formula (I$_R$)

wherein the carbon atom to which the group Ar$^2$ is attached is in the absolute configuration as drawn in Formula (I$_R$);

or a pharmaceutically acceptable salt thereof.

3. A compound according to claim 1; wherein Ar$^1$ represents phenyl which is mono-, di- or tri-substituted, wherein the substituents are independently selected from halogen, methyl, cyano, and methoxy;

wherein at least one of said substituents is attached in a meta- or in para-position of said phenyl;

or a pharmaceutically acceptable salt thereof.

4. A compound according to claim 3; wherein at least one of said substituents is attached in para-position of said phenyl and the substituent is selected from halogen, methyl, cyano, and methoxy;

or a pharmaceutically acceptable salt thereof.

5. A compound according to claim 3; wherein at least one of said substituents is attached in a meta-position of said phenyl and the substituent is halogen;

or a pharmaceutically acceptable salt thereof.

6. A compound according to claim 1; wherein Ar$^1$ represents a phenyl group of the structure

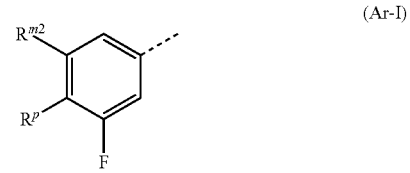

(Ar-I)

wherein

R$^{m2}$ represents halogen; and

R$^p$ represents hydrogen, halogen, methyl, cyano, or methoxy;

or a pharmaceutically acceptable salt thereof.

7. A compound according to claim 1; wherein Ar$^2$ represents phenyl which is mono-, di-, or tri-substituted; wherein
one substituent is attached in ortho-position with regard to the point of attachment of Ar$^2$ to the rest of the molecule; wherein said substituent is C$_{1-6}$-alkyl, C$_{3-6}$-cycloalkyl, C$_{1-3}$-fluoroalkyl, C$_{1-3}$-fluoroalkoxy, halogen, hydroxy-C$_{1-3}$-alkyl, or phenyl;

and the other substituent(s), if present, is/are attached in meta- and/or para-position with regard to the point of attachment of Ar$^2$ to the rest of the molecule; wherein the substituent(s) independently are C$_{1-6}$-alkyl, C$_{3-6}$-cycloalkyl, C$_{1-3}$-fluoroalkyl, or halogen; or 5- or 6-membered heteroaryl, wherein said 5- or 6-membered heteroaryl independently is mono-, di-, or tri-substituted; wherein
one substituent is attached in ortho-position with regard to the point of attachment of Ar$^2$ to the rest of the molecule; wherein said substituent is C$_{1-6}$-alkyl, C$_{3-6}$-cycloalkyl, or C$_{1-3}$-fluoroalkyl;

and the other substituent(s), if present, is/are independently C$_{1-6}$-alkyl, C$_{3-6}$-cycloalkyl, C$_{1-3}$-fluoroalkyl, or halogen;

or a pharmaceutically acceptable salt thereof.

8. A compound according to claim 1; wherein Ar$^2$ represents

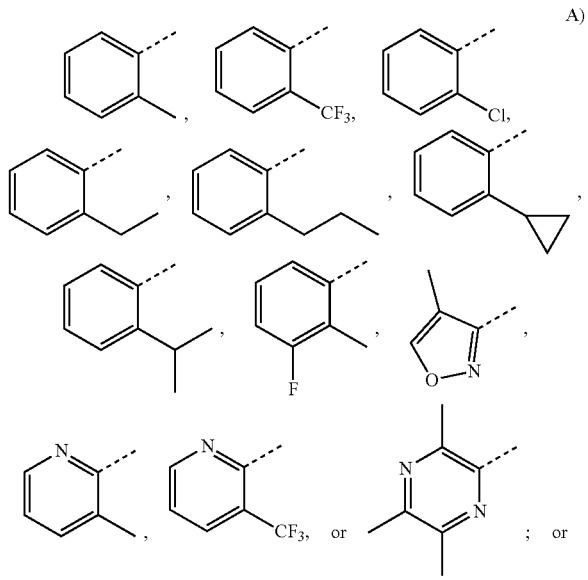

A)

-continued

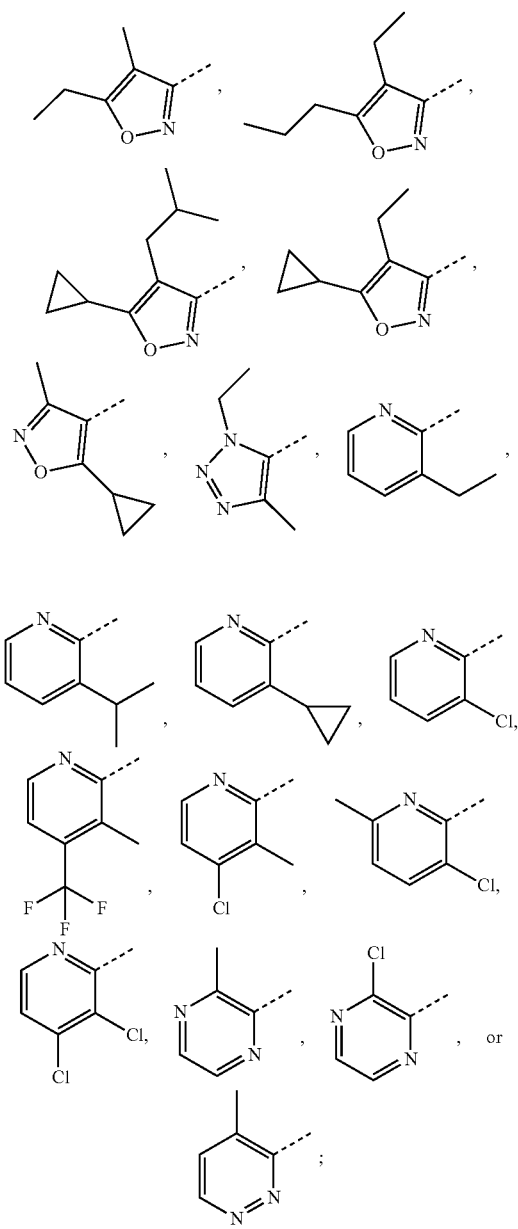

or a pharmaceutically acceptable salt thereof.

9. A compound according to claim 1; wherein
R$^{1a}$ represents hydrogen; and R$^{1b}$ represents
—C$_{2-4}$-alkyl; or
phenyl which is unsubstituted, mono- or di-substituted with methyl;
or R$^{1a}$ and R$^{1b}$ both represent methyl, ethyl, or n-propyl;
or R$^{1a}$ and R$^{1b}$ together with the carbon atom to which they are attached form a 3- to 6-membered ring selected from
C$_{4-6}$-cycloalkylene, wherein said C$_{4-6}$-cycloalkylene independently is unsubstituted, mono-, or di-substituted, wherein the substituents independently are methyl or fluoro;
tetrahydro-2H-pyran-4,4-diyl; 2,2-dimethyltetrahydro-2H-pyran-4,4-diyl, or 2,2,6,6-tetramethyltetrahydro-2H-pyran-4,4-diyl;
tetrahydro-2H-thiopyran-1,1-dioxide-4,4-diyl;
piperidine-4,4-diyl, wherein the nitrogen of said piperidine is unsubstituted, or substituted with —C$_{1-3}$-alkyl, —CO—C$_{1-3}$-alkyl, —CO—O-C$_{1-3}$-alkyl, —CO-NH-cyclopropyl, —SO$_2$—C$_{1-3}$-alkyl, —SO$_2$-cyclopropyl, or —SO$_2$—NH—C$_{1-3}$-alkyl; or
azetidine-3,3-diyl, wherein the nitrogen of said azetidine is unsubstituted, or substituted with —SO$_2$-C$_{1-3}$-alkyl, —CO—O-C$_{1-3}$-alkyl, or —CO—NH-cyclopropyl; or
R$^{1a}$ and R$^{1b}$ together with the carbon atom to which they are attached form a spiro-bicyclic ring system of the structure:

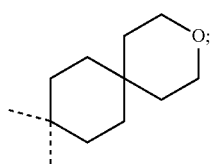

or a pharmaceutically acceptable salt thereof.

10. A compound according to claim 1; wherein R$^2$ represents methoxy;
or a pharmaceutically acceptable salt thereof.

11. A pharmaceutical composition comprising a compound according to claim 1, or a pharmaceutically acceptable salt thereof, and a pharmaceutically acceptable carrier.

12. A method for the treatment of an indication mediated by galectin-3 selected from fibrosis of organs; neuropathic pain; insulin resistance disorders, and cancer wherein the cancer is treated in combination with immunotherapy, comprising administering to a subject in a need thereof an effective amount of a compound according to claim 1, or of a pharmaceutically acceptable salt thereof.

13. A compound, wherein said compound is:
(2S,3R,4S,5R,6R)-2-(((R)-2-Hydroxy-1-phenylethyl)thio)-6-(hydroxymethyl)-4-(4-(3,4,5-trifluorophenyl)-1H-1,2,3-triazol-1-yl)tetrahydro-2H-pyran-3,5-diol;
(2S,3R,4S,5R,6R)-2-(((R)-1-(2-Bromophenyl)-2-hydroxyethyl)thio)-6-(hydroxymethyl)-4-(4-(3,4,5-trifluorophenyl)-1H-1,2,3-triazol-1-yl)tetrahydro-2H-pyran-3,5-diol;
(2S,3R,4S,5R,6R)-2-(((R)-2-Hydroxy-1-(2-isopropylphenyl)ethyl)thio)-6-(hydroxymethyl)-4-(4-(3,4,5-trifluorophenyl)-1H-1,2,3-triazol-1-yl)tetrahydro-2H-pyran-3,5-diol;
(2S,3R,4S,5R,6R)-2-(((R)-2-Hydroxy-2-methyl-1-(o-tolyl) propyl)thio)-6-(hydroxymethyl)-4-(4-(3,4,5-trifluorophenyl)-1H-1,2,3-triazol-1-yl)tetrahydro-2H-pyran-3,5-diol;
(2S,3R,4S,5R,6R)-2-(((R)-1-(2-Ethylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;
(2S,3R,4S,5R,6R)-2-(((R)-2-Hydroxy-2-methyl-1-(2-propylphenyl) propyl)thio)-6-(hydroxymethyl)-4-(4-(3,4,5-trifluorophenyl)-1H-1,2,3-triazol-1-yl)tetrahydro-2H-pyran-3,5-diol;
(2S,3R,4S,5R,6R)-2-(((R)-2-Hydroxy-1-(2-isobutylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-pentylphenyl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-([1,1'-Biphenyl]-2-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2-Chlorophenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-(trifluoromethyl)phenyl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2,3-Dichlorophenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(3-Fluoro-2-methylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(naphthalen-1-yl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-methylpyridin-3-yl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(4-methylpyridin-3-yl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(3,5,6-trimethylpyrazin-2-yl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(4-methylisoxazol-3-yl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(3,5-Dimethylisoxazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2,5-Dimethylthiazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(4-methylthiophen-3-yl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Ethyl-2-hydroxy-1-(3-methylisoxazol-4-yl)butyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2R)-2-Hydroxy-1-(2-(trifluoromethyl)phenyl) butyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2S)-2-Hydroxy-1-(2-(trifluoromethyl)phenyl) butyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3,3-Difluoro-1-hydroxycyclobutyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(3R,4R,5R,6R)-2-((R)-2-(1-Hydroxycyclobutyl)-2-(o-tolyl)ethyl)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxy-3,3-dimethylcyclobutyl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-(1-Hydroxy-3-methylcyclobutyl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-((2R,3R)-1-Hydroxy-2,3-dimethylcyclobutyl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-((2R,3S)-1-Hydroxy-2,3-dimethylcyclobutyl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-((2S,3R)-1-Hydroxy-2,3-dimethylcyclobutyl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R)-((2S,3S)-1-Hydroxy-2,3-dimethylcyclobutyl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclopentyl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxytetrahydro-2H-pyran-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-2,2,6,6-tetramethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-((R)-4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-((S)-4-Hydroxy-2,2-dimethyltetrahydro-2H-pyran-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3,3-Difluoro-1-hydroxycyclobutyl)(3-(trifluoromethyl) pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(3-(trifluoromethyl) pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(4-methylisoxazol-3-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(2-isopropylphenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-(trifluoromethyl) pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(2-Chlorophenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxytetrahydro-2H-pyran-4-yl)(3-(trifluoromethyl)pyridin-2-yl)methyl)thio)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxytetrahydro-2H-pyran-4-yl)(3,5,6-trimethylpyrazin-2-yl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(3-(trifluoromethyl) pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4-Hydroxy-1-methylpiperidin-4-yl)(3,5,6-trimethylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(1-Hydroxycyclopentyl)(3-(trifluoromethyl) pyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-2-(Hydroxymethyl)-6-(((R)-(4-hydroxypiperidin-4-yl)(2-(trifluoromethyl)phenyl)methyl)thio)-4-(4-(3,4,5-trifluorophenyl)-1H-1,2,3-triazol-1-yl)tetrahydro-2H-pyran-3,5-diol;

4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio) (2-(trifluoromethyl)phenyl)methyl)-4-hydroxy-N-methylpiperidine-1-sulfonamide;

(2S,3R,4S,5R,6R)-2-(((R)-(4-Hydroxy-1-(methylsulfonyl) piperidin-4-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

1-(4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio) (2-(trifluoromethyl)phenyl)methyl)-4-hydroxypiperidin-1-yl)ethan-1-one;

N-Cyclopropyl-4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio) (2-(trifluoromethyl)phenyl)methyl)-4-hydroxypiperidine-1-carboxamide;

Methyl 4-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio) (2-(trifluoromethyl)phenyl)methyl)-4-hydroxypiperidine-1-carboxylate;

(2S,3R,4S,5R,6R)-4-(4-(3,5-Difluoro-4-methylphenyl)-1H-1,2,3-triazol-1-yl)-2-(((R)-2-hydroxy-2-methyl-1-(2-(trifluoromethyl)phenyl) propyl)thio)-6-(hydroxymethyl)tetrahydro-2H-pyran-3,5-diol;

(2S,3R,4S,5R,6R)-2-(((R)-2-Hydroxy-2-methyl-1-(2-(trifluoromethyl)phenyl) propyl)thio)-6-(hydroxymethyl)-4-(4-(naphthalen-2-yl)-1H-1,2,3-triazol-1-yl)tetrahydro-2H-pyran-3,5-diol;

4-(1-(2S,3R,4S,5R,6R)-3,5-Dihydroxy-2-(((R)-2-hydroxy-2-methyl-1-(2-(trifluoromethyl)phenyl) propyl)thio)-6-(hydroxymethyl)tetrahydro-2H-pyran-4-yl)-1H-1,2,3-triazol-4-yl)-2-fluorobenzonitrile;

(2R,3R,4S,5R,6S)-2-(Hydroxymethyl)-6-(((R)-4-hydroxytetrahydro-2H-pyran-4-yl) (o-tolyl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-1-(2-isopropylphenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2-Cyclopropylphenyl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-1-(2-(2-hydroxyethyl)phenyl)-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-2-Hydroxy-2-methyl-1-(2-(trifluoromethyl) pyridin-3-yl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-1-(2,5-Dimethyloxazol-4-yl)-2-hydroxy-2-methylpropyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2R)-2-Hydroxy-2-phenyl-1-(2-(trifluoromethyl)phenyl)ethyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2S)-2-Hydroxy-2-phenyl-1-(2-(trifluoromethyl)phenyl)ethyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2R)-2-Hydroxy-2-(o-tolyl)-1-(2-(trifluoromethyl)phenyl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((1R,2S)-2-Hydroxy-2-(o-tolyl)-1-(2-(trifluoromethyl)phenyl) propyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(5-Cyclopropyl-3-methylisoxazol-4-yl)(1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-((R)-4-Hydroxy-2,2-dimethyltetrahydro-2H-pyran-4-yl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-((S)-4-Hydroxy-2,2-dimethyltetrahydro-2H-pyran-4-yl) (o-tolyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(2,3-Dichlorophenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(2-Cyclopropylphenyl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-methylpyrazin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(5-Cyclopropyl-4-ethylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(5-Cyclopropyl-4-isobutylisoxazol-3-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(3-isopropylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3-Chloropyrazin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3-Cyclopropylpyridin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-(4,4-Difluoro-1-hydroxycyclohexyl)(4-methylpyridazin-3-yl)methyl)thio)-6-(hydroxymethyl)-4-(4-(3,4,5-trifluorophenyl)-1H-1,2,3-triazol-1-yl)tetrahydro-2H-pyran-3,5-diol;

4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio) (4-methylisoxazol-3-yl)methyl)-4-hydroxytetrahydro-2H-thiopyran 1,1-dioxide;

4-((R)-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio) (3-methylpyridin-2-yl)methyl)-4-hydroxytetrahydro-2H-thiopyran 1,1-dioxide;

(2R,3R,4S,5R,6S)-2-(Hydroxymethyl)-6-(((R)-(4-hydroxytetrahydro-2H-pyran-4-yl)(3-methylpyridin-2-yl)methyl)thio)-4-(4-(3,4,5-trifluorophenyl)-1H-1,2,3-triazol-1-yl)tetrahydro-2H-pyran-3,5-diol;

(2S,3R,4S,5R,6R)-2-(((R)-(3-Hydroxy-1-(methylsulfonyl) azetidin-3-yl)(2-(trifluoromethyl)phenyl)methyl)thio)-6-(hydroxymethyl)-4-(4-(3,4,5-trifluorophenyl)-1H-1,2,3-triazol-1-yl)tetrahydro-2H-pyran-3,5-diol;

Methyl 3-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio) (2-(trifluoromethyl)phenyl)methyl)-3-hydroxyazetidine-1-carboxylate;

N-Cyclopropyl-3-((R)-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio) (2-(trifluoromethyl)phenyl)methyl)-3-hydroxyazetidine-1-carboxamide;

(2R,3R,4S,5R,6S)-6-(((R)-(4,4-Difluoro-1-hydroxycyclohexyl)(3-methylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-(trifluoromethyl) pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(1-Hydroxycyclohexyl)(3-(trifluoromethyl) pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

2R,3R,4S,5R,6S)-6-(((R)-(3-Chloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-((R)-4-Hydroxy-2,2-dimethyltetrahydro-2H-pyran-4-yl)(2-(trifluoromethyl)phenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-((S)-4-Hydroxy-2,2-dimethyltetrahydro-2H-pyran-4-yl)(2-(trifluoromethyl)phenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

4-Hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) (3-methylpyridin-2-yl)methyl)tetrahydro-2H-thiopyran 1,1-dioxide;

(2R,3R,4S,5R,6S)-2-(Hydroxymethyl)-6-(((R)-(4-hydroxytetrahydro-2H-pyran-4-yl)(3-methylpyridin-2-yl)methyl)thio)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-((R)-4-Hydroxy-2,2-dimethyltetrahydro-2H-pyran-4-yl) (o-tolyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-((S)-4-Hydroxy-2,2-dimethyl-tetrahydro-2H-pyran-4-yl) (o-tolyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-isopropylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(3-Cyclopropylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(4-methylpyridazin-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-methylpyrazin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(1-Hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(2-isopropylphenyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(2-Cyclopropylphenyl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(1,4-dimethyl-1H-pyrazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(1-ethyl-4-methyl-1H-1,2,3-triazol-5-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4-Chloro-1-ethyl-1H-pyrazol-5-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(5-ethyl-4-methylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-2-(Hydroxymethyl)-6-(((R)-(4-hydroxytetrahydro-2H-pyran-4-yl)(4-methylisoxazol-3-yl)methyl)thio)-5-methoxy-4-(4-(3,4,5-trifluorophenyl)-1H-1,2,3-triazol-1-yl)tetrahydro-2H-pyran-3-ol;

4-Hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)(4-methylisoxazol-3-yl)methyl)tetrahydro-2H-thiopyran 1,1-dioxide;

(2R,3R,4S,5R,6S)-6-(((R)-(5-Cyclopropyl-3-methylisoxazol-4-yl)(1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(5-Cyclopropyl-4-ethylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(5-Cyclopropyl-4-isobutylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(3-Chloropyrazin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4-Chloro-3-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-ethylpyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(3,4-Dichloropyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2S,3R,4S,5R,6R)-2-(((R)-(3,6-Dichloropyridin-2-yl)(4,4-difluoro-1-hydroxycyclohexyl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-((R)-4-Hydroxy-2,2-dimethyl-tetrahydro-2H-pyran-4-yl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2S,3R,4S,5R,6R)-2-(((R)-((S)-4-Hydroxy-2,2-dimethyl-tetrahydro-2H-pyran-4-yl)(3-methylpyridin-2-yl)methyl)thio)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6S)-6-(((R)-(5-Cyclopropyl-4-methylisoxazol-3-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-((((R)-4,4-Difluoro-1-hydroxycyclohexyl)(4-ethyl-5-propylisoxazol-3-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3-methyl-4-(trifluoromethyl) pyridin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

2R,3R,4S,5R,6S)-6-(((R)-(3-Chloro-6-methylpyridin-2-yl)(4,4-difluoro-1-hydroxycyclohexyl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3,5,6-trimethylpyrazin-2-yl)methyl)thio)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6S)-6-(((R)-(4,4-Difluoro-1-hydroxycyclohexyl)(3,6-dimethylpyridin-2-yl)methyl)thio)-2-

(hydroxymethyl)-5-methoxy-4-(4-(3,4,5-trifluorophenyl)-1H-1,2,3-triazol-1-yl)tetrahydro-2H-pyran-3-ol;
9-((R)-(((2S,3R,4S,5R,6R)-5-Hydroxy-6-(hydroxymethyl)-3-methoxy-4-(4-(3,4,5-trifluorophenyl)-1H-1,2,3-triazol-1-yl)tetrahydro-2H-pyran-2-yl)thio) (3-methylpyridin-2-yl)methyl)-3-oxaspiro[5.5]undecan-9-ol;
(2R,3R,4S,5R,6S)-6-(((R)-(4,4-Difluoro-1-hydroxycyclohexyl)(3-methylpyridin-2-yl)methyl)thio)-5-ethoxy-2-(hydroxymethyl)-4-(4-(3,4,5-trifluorophenyl)-1H-1,2,3-triazol-1-yl)tetrahydro-2H-pyran-3-ol;
1-(Cyclopropylsulfonyl)-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) (2-(trifluoromethyl)phenyl)methyl) piperidin-4-ol;
1-(4-Hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) (2-(trifluoromethyl)phenyl)methyl) piperidin-1-yl) ethan-1-one;
N-Cyclopropyl-4-hydroxy-4-((R)-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) (2-(trifluoromethyl)phenyl)methyl) piperidine-1-carboxamide;
(2R,3R,4S,5R,6S)-6-(((R)-(4,4-Difluoro-1-hydroxycyclohexyl)(3-methylpyridin-2-yl)methyl)thio)-4-(4-(3,4-difluorophenyl)-1H-1,2,3-triazol-1-yl)-2-(hydroxymethyl)-5-methoxytetrahydro-2H-pyran-3-ol;
(2R,3R,4S,5R,6S)-6-(((R)-(4,4-Difluoro-1-hydroxycyclohexyl)(3-methylpyridin-2-yl)methyl)thio)-2-(hydroxymethyl)-5-methoxy-4-(4-(2,3,4-trifluorophenyl)-1H-1,2,3-triazol-1-yl)tetrahydro-2H-pyran-3-ol;
((2R,3R,4S,5R,6S)-4-(4-(4-Chloro-2,3-difluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;
(2R,3R,4S,5R,6S)-6-(((R)-(4,4-Difluoro-1-hydroxycyclohexyl)(3-methylpyridin-2-yl)methyl)thio)-4-(4-(2,3-difluoro-4-methylphenyl)-1H-1,2,3-triazol-1-yl)-2-(hydroxymethyl)-5-methoxytetrahydro-2H-pyran-3-ol;
(2R,3R,4S,5R,6S)-4-(4-(4-Bromo-3,5-difluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;
(2R,3R,4S,5R,6S)-4-(4-(3,4-Dichloro-5-fluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;
(2R,3R,4S,5R,6S)-4-(4-(4-Bromo-3-fluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;
(2R,3R,4S,5R,6S)-4-(4-(4-Chloro-3,5-difluorophenyl)-1H-1,2,3-triazol-1-yl)-6-(((R)-(4,4-difluoro-1-hydroxycyclohexyl)(3-methylpyridin-2-yl)methyl)thio)-2-(hydroxymethyl)-5-methoxytetrahydro-2H-pyran-3-ol;
(2R,3R,4S,5R,6S)-6-(((R)-(4,4-Difluoro-1-hydroxycyclohexyl)(3-methylpyridin-2-yl)methyl)thio)-4-(4-(3,5-difluoro-4-methylphenyl)-1H-1,2,3-triazol-1-yl)-2-(hydroxymethyl)-5-methoxytetrahydro-2H-pyran-3-ol; or
(2R,3R,4S,5R,6S)-6-(((R)-(4,4-Difluoro-1-hydroxycyclohexyl)(3-methylpyridin-2-yl)methyl)thio)-4-(4-(6-fluoro-5-methylpyridin-3-yl)-1H-1,2,3-triazol-1-yl)-2-(hydroxymethyl)-5-methoxytetrahydro-2H-pyran-3-ol;
or a pharmaceutically acceptable salt thereof.

14. A pharmaceutical composition comprising a compound according to claim 13, or a pharmaceutically acceptable salt thereof, and a pharmaceutically acceptable carrier.

15. A method for the treatment of an indication mediated by galectin-3 selected from fibrosis of organs; neuropathic pain; insulin resistance disorders, and cancer wherein the cancer is treated in combination with immunotherapy, comprising administering to a subject in a need thereof an effective amount of a compound according to claim 13, or of a pharmaceutically acceptable salt thereof.

\* \* \* \* \*